(12) United States Patent
Jensen

(10) Patent No.: US 8,324,353 B2
(45) Date of Patent: *Dec. 4, 2012

(54) CHIMERIC IMMUNORECEPTOR USEFUL IN TREATING HUMAN GLIOMAS

(75) Inventor: Michael Jensen, Sierra Madre, CA (US)

(73) Assignee: City of Hope, Durate, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/046,518

(22) Filed: Mar. 11, 2011

(65) Prior Publication Data

US 2011/0223129 A1    Sep. 15, 2011

Related U.S. Application Data

(63) Continuation of application No. 12/314,195, filed on Dec. 5, 2008, now abandoned, which is a continuation-in-part of application No. 11/274,344, filed on Nov. 16, 2005, now Pat. No. 7,514,537, which is a continuation-in-part of application No. 10/134,645, filed on Apr. 30, 2002, now abandoned.

(60) Provisional application No. 60/286,981, filed on Apr. 30, 2001, provisional application No. 61/091,915, filed on Aug. 26, 2008.

(51) Int. Cl.
  *C07K 16/46*   (2006.01)
  *C07K 19/00*   (2006.01)
  *C12N 5/0783*   (2010.01)
  *C12N 5/22*   (2006.01)
  *C12N 15/63*   (2006.01)

(52) U.S. Cl. .................. 530/387.3; 424/93.21; 435/69.7; 435/320.1; 435/372.3; 530/350

(58) Field of Classification Search .......................... None
See application file for complete search history.

(56) References Cited

U.S. PATENT DOCUMENTS 5,359,046 A   10/1994   Capon et al.
(Continued)

FOREIGN PATENT DOCUMENTS

WO   WO 00/23573 A2   4/2000
(Continued)

OTHER PUBLICATIONS

"Protein Expression", Chapter 16 in Current Protocols in Molecular Biology (2007), published by John Wiley & Sons, pp. 16.0.1-16.25. 24; 329 pages total.*

(Continued)

*Primary Examiner* — Zachary Howard
(74) *Attorney, Agent, or Firm* — Rothwell, Figg, Ernst & Manbeck, P.C.

(57) ABSTRACT

The present invention relates to chimeric transmembrane immunoreceptors, named "zetakines," comprised of an extracellular domain comprising a soluble receptor ligand linked to a support region capable of tethering the extracellular domain to a cell surface, a transmembrane region and an intracellular signalling domain. Zetakines, when expressed on the surface of T lymphocytes, direct T cell activity to those specific cells expressing a receptor for which the soluble receptor ligand is specific. Zetakine chimeric immunoreceptors represent a novel extension of antibody-based immunoreceptors for redirecting the antigen specificity of T cells, with application to treatment of a variety of cancers, particularly via the autocrin/paracrine cytokine systems utilized by human maligancy. In a preferred embodiment is a glioma-specific immunoreceptor comprising the extracellular targeting domain of the IL-13Rα2-specific IL-13 mutant IL-13 (E13Y) linked to the Fc region of IgG, the transmembrane domain of human CD4, and the human CD3 zeta chain.

5 Claims, 44 Drawing Sheets

U.S. PATENT DOCUMENTS 6,410,319 B1  6/2002  Raubitschek et al.
7,514,537 B2  4/2009  Jensen

FOREIGN PATENT DOCUMENTS

WO    2008095141 A2   8/2008

OTHER PUBLICATIONS

Altenschmidt et al., "Cytolysis of Tumor Cells Expressing in the NEU/ERBB-2, ERBB-3, and ERBB-4 Receptors by Genetically Targeted Naive T Lymphocytes" Clinical Cancer Research, The American Association for Cancer Research, 2(6): 1001-1008, 1996.
Ashkenazi et al., Methods: A Companion to Methods in Enzymology: 8:104-115, 1995.
Bonnerot et al., Immunology Letters 47:1-4, 1997.
Campbell et al., Theriology 47(1):63-72, 1997.
Debinski et al., "Human Glioma Cells Overexpress Receptors for Interleukin 13 and are Extremely Sensitive to a Novel Chimeric Protein Composed of Interleukin 13 and Pseudomonas Exotoxin" Clinical Cancer Res. 1:1253-1258, 1995.
Debinski et al., "Novel Anti-Brain Tumor Cytotoxins Specific for Cancer Cells," Nature Biotechnology 16:449-453, 1998.
Debinski et al., "Receptor for Interleukin 13 is a Marker and Therapeutic Target for Human High-Grade Gliomas," Clinical Cancer Res. 5:985-990, 1999.
Debinski et al., "Receptor for Interleukin 13 is Abundantly and Specifically Over-Expressed in Patients with Glioblastoma Multiforme" 15:481-486, 1999.
Debinski et al., "Retargeting 13 for Radioimmunodetection and Radioimmunotherapy of Human High-Grade Gliomas" Clinical Cancer Res. 5:481-486, 1999.
Debinski et al., Clinical Cancer Res. 5:3143-3147, 1999.
Debinski et al., "Novel Way to Increase Targeting Specificity to a Human Glioblastoma-Associated Receptor for Interleukin 13" Int. J. Cancer 76:547-551, 1998.
Debinski "Expression of a Restrictive Receptor for Interleukin 13 is associated with Glial Transformation" J. Neuro-Oncology 48:103-111, 2000.
Ehtesham et al. Cancer Control. 11(3):192-207, 2004.
Jensen et al., "CD20 is a Molecular Target for scFvFc:zeta Receptor Redirected T Cells: Implications for Cellular Immunotherapy of CD20* Malignancy" Biol. Blood Marrow Transplant 4:75-83, 1998.
Joshi et al., "Interleukin-13 Receptor α Chain: A Novel Tumor-Associated Transmembrane Protein in Primary Explants of Human Malignant Gliomas" Cancer Res. 60:1168-1172, 2000.
Kahlon et al., "Specific Recognition and Killing of Glioblastoma Multiforme by Interleukin 13-Zetalcine Redirected Cytolytic T Cells" Cancer Res. 64(24):9160-9166, 2004.
Kahlon et al., "Redirecting T lymphocyte antigen specificity via engineered zetakine immonoreceptors: development of a prototype construct specific for the tumor-restricted IL-13alpha2 receptor" Molecular Therapy 3(5):S374, AB, 2001.
Kahlon et al., "The IL-13 zetakine chimeric immunoreceptor: a novel approach to genetically engineer T cells for glioma immunotherapy," Neuro-Oncology, vol. 3, No. 4, Oct. 2001, pp. 315-316, Washington, D.C.
Lazovic et al., Clin. Cancer Res. 14(2):3832-3839, 2008.
Liu et al., "Interleukin-13 Sensitivity and Receptor Phenotypes of Human Glial Cell Lines: Non-Neoplastic Glia and Low-Grade Astrocytoma Differ from Malignant Glioma" Cancer Immunol. Immunother 49:319-324, 2000.
Minty et al., "Interleukin-13 is a New Human Lymphokinie Regulating Inflammatory and Immune Responses" Nature 362:248-240, 1993.
Mintz et al., "Cancer Genetics/Epigenetics and the X Chromosome" Possible New Links for Malignant Glioma Pathogenesis and Immune-Based Therapies Crit. Rev. Oncog 11(1):77-95, 2000.
Moeller et al., "A Functional Role for CD28 Costimulation in Tumor Recognition by Single-Chain Receptor Modified T Cells" Cancer Gene Therapy 11(5):371-379, 2004.
Murata et al., "Structure of IL-13 Receptor: Analysis of Subunit Composition in Cancer and Immune Cells" Biochemical and Biophysical Research Communications 238:90-94, 1997.
Niederman et al., "Antitumor Activity of Cytotoxic T Lymphocyte Engineered to Target Vascular Endothelial Growth Factor Receptors" Proceedings of the National Academy of Sciences of USA, National Academy of Science 99(19):7009-7014, 2002.
Obiri et al., "The IL-13 Receptor Structure Differs on Various Cell Types and May Share More than One Component With IL-4 Receptor" J. Immun. 158:756-764, 1997.
Stastny et al., "Medulloblastomas Expressing IL13Rα2 are Targets for IL13-zetakine+ Cytolytic T Cells," J. Pediatr Hematol Oncol 29:669-677, 2007.
Thompson et al., "Mutants of Interleukin-13 with Altered Reactivity Toward Interleukin-13 Receptors" J. Biol. Chem. 274(42):29944-29950, 1999.
Xu et al., "Targeting and Therapy of Carcinoembryonic Antigen-Expressing Tumors in Transgenic Mice with an Antibody-Interleukin 2 Fusion Protein" Cancer Research 60:4475-4484, 2000.
Yamasaki et al., "Specific Adoptive Immunotherapy of Malignant Glioma with Long-Term Cytotoxic T Lymphocyte Line Expanded in T-Cell Growth Factor" Experimental Study and Future Prospects, Neurosurg 7:37-54, 1984.

* cited by examiner

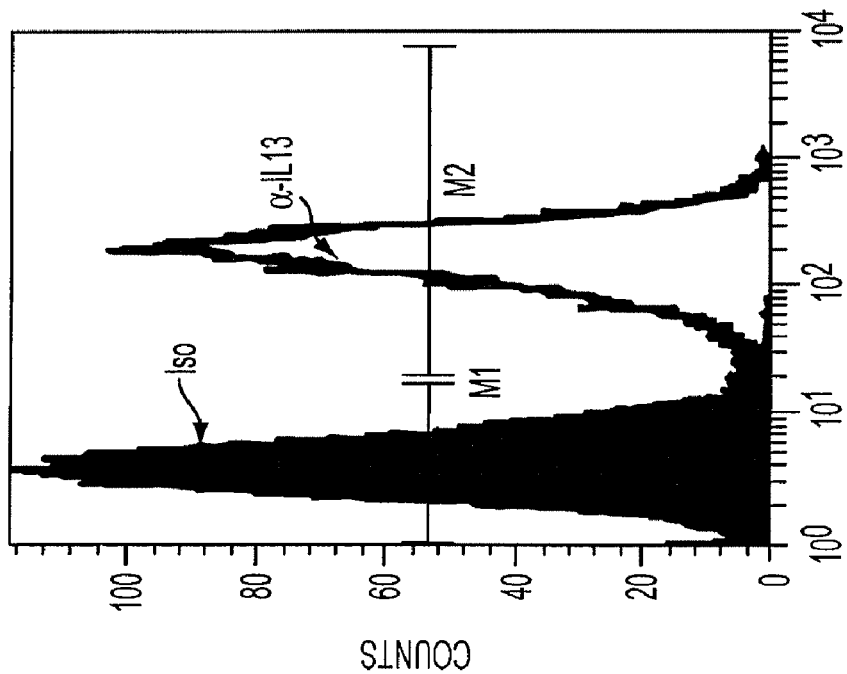
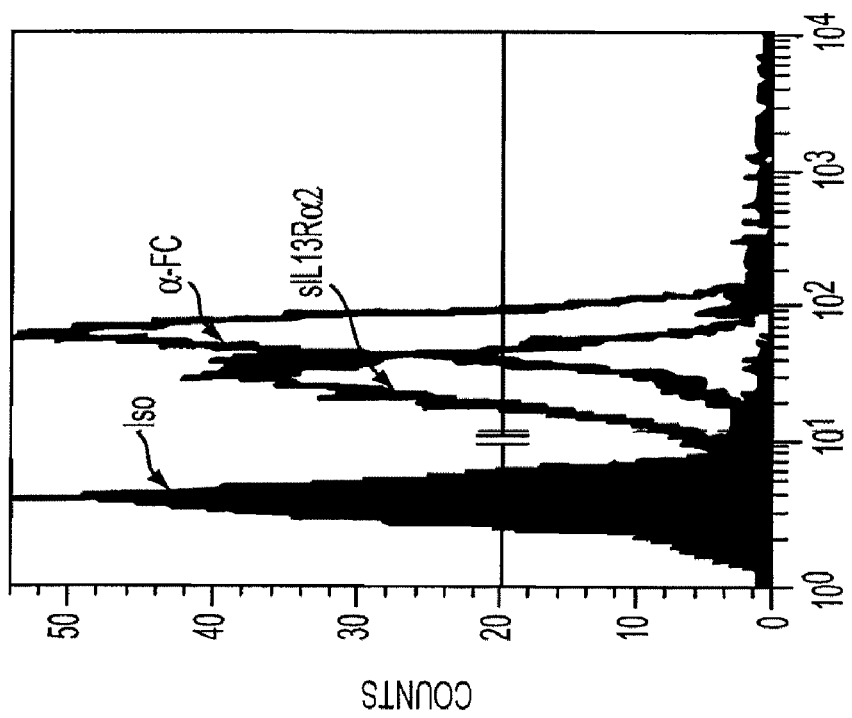
FIG. 2A
FIG. 2B

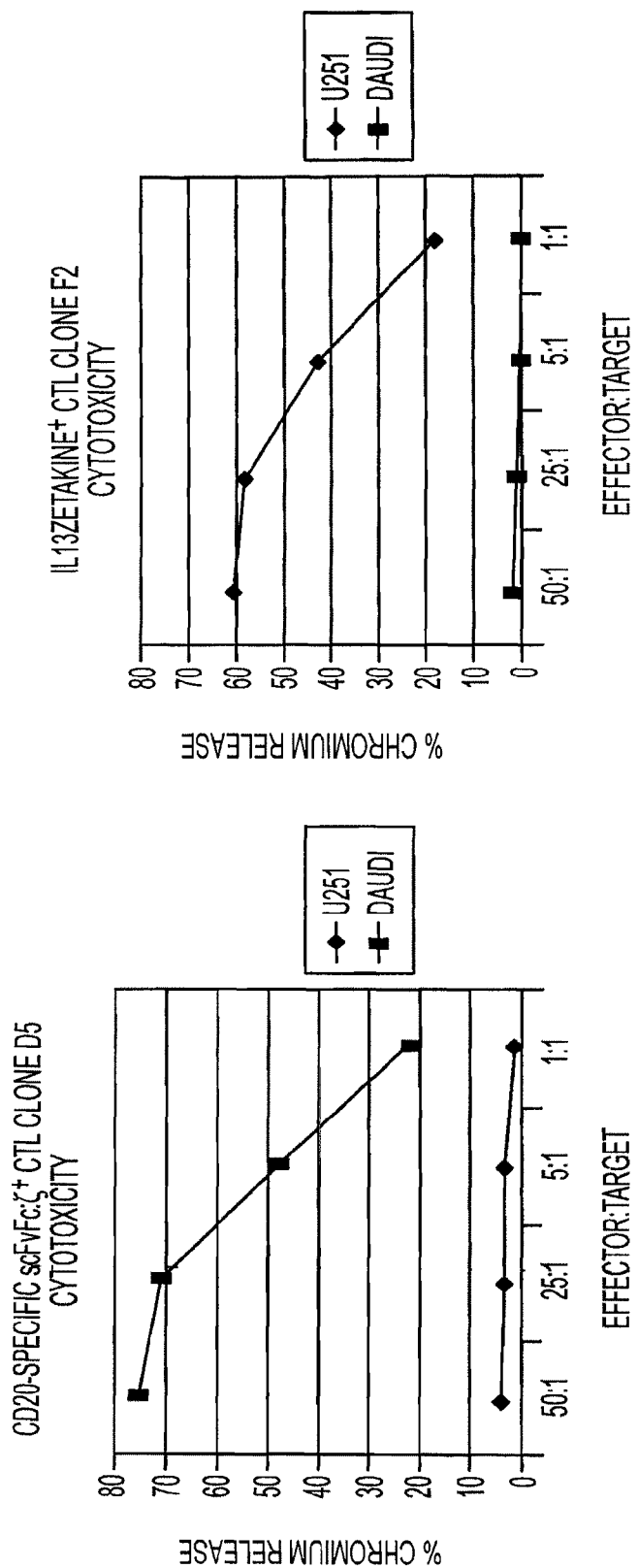

Plasmid DNA Vector Sequence

```
     (hEF1p→)
1    TCGAAGGATC TGCGATCGCT CCGGTGCCCG TCAGTGGGCA GAGCGCACAT CGCCCACAGT
     AGCTTCCTAG ACGCTAGCGA GGCCACGGGC AGTCACCCGT CTCGCGTGTA GCGGGTGTCA

61   CCCCGAGAAG TTGGGGGGAG GGGTCGGCAA TTGAACCGGT GCCTAGAGAA GGTGGCGCGG
     GGGGCTCTTC AACCCCCCTC CCCAGCCGTT AACTTGGCCA CGGATCTCTT CCACCGCGCC

121  GGTAAACTGG GAAAGTGATG TCGTGTACTG GCTCCGCCTT TTTCCCGAGG GTGGGGGAGA
     CCATTTGACC CTTTCACTAC AGCACATGAC CGAGGCGGAA AAAGGGCTCC CACCCCCTCT

181  ACCGTATATA AGTGCAGTAG TCGCCGTGAA CGTTCTTTTT CGCAACGGGT TTGCCGCCAG
     TGGCATATAT TCACGTCATC AGCGGCACTT GCAAGAAAAA GCGTTGCCCA AACGGCGGTC

241  AACACAGCTG AAGCTTCGAG GGGCTCGCAT CTCTCCTTCA CGCGCCCGCC GCCCTACCTG
     TTGTGTCGAC TTCGAAGCTC CCCGAGCGTA GAGAGGAAGT GCGCGGGCGG CGGGATGGAC

301  AGGCCGCCAT CCACGCCGGT TGAGTCGCGT TCTGCCGCCT CCCGCCTGTG GTGCCTCCTG
     TCCGGCGGTA GGTGCGGCCA ACTCAGCGCA AGACGGCGGA GGGCGGACAC CACGGAGGAC

361  AACTGCGTCC GCCGTCTAGG TAAGTTTAAA GCTCAGGTCG AGACCGGGCC TTTGTCCGGC
     TTGACGCAGG CGGCAGATCC ATTCAAATTT CGAGTCCAGC TCTGGCCCGG AAACAGGCCG

421  GCTCCCTTGG AGCCTACCTA GACTCAGCCG GCTCTCCACG CTTTGCCTGA CCCTGCTTGC
     CGAGGGAACC TCGGATGGAT CTGAGTCGGC CGAGAGGTGC GAAACGGACT GGGACGAACG

481  TCAACTCTAC GTCTTTGTTT CGTTTTCTGT TCTGCGCCGT TACAGATCCA AGCTGTGACC
     AGTTGAGATG CAGAAACAAA GCAAAAGACA AGACGCGGCA ATGTCTAGGT TCGACACTGG

541  GGCGCCTACG TAAGTGATAT CTACTAGATT TATCAAAAAG AGTGTTGACT TGTGAGCGCT
     CCGCGGATGC ATTCACTATA GATGATCTAA ATAGTTTTTC TCACAACTGA ACACTCGCGA

601  CACAATTGAT ACTTAGATTC ATCGAGAGGG ACACGTCGAC TACTAACCTT CTTCTCTTTC
     GTGTTAACTA TGAATCTAAG TAGCTCTCCC TGTGCAGCTG ATGATTGGAA GAAGAGAAAG (IL13zetakine→)
                                            M  L  L    L  V  T  S    L  L  L
661  CTACAGCTGA GATCACCCTA GAGCCGCCAC CATGCTTCTC CTGGTGACAA GCCTTCTGCT
     GATGTCGACT CTAGTGGGAT CTCGGCGGTG GTACGAAGAG GACCACTGTT CGGAAGACGA ·  C  E  L    P  H  P  A    F  L  L    I  P  G    P  V  P  P    S  T  A
721  CTGTGAGTTA CCACACCCAG CATTCCTCCT GATCCCAGGC CCTGTGCCTC CCTCTACAGC
     GACACTCAAT GGTGTGGGTC GTAAGGAGGA CTAGGGTCCG GGACACGGAG GGAGATGTCG
```

FIG. 12A

```
       · L  R  Y    L  I  E  E  L  V  N    I  T  Q    N  Q  K  A    P  L  C
 781   CCTCAGGTAC CTCATTGAGG AGCTGGTCAA CATCACCCAG AACCAGAAGG CTCCGCTCTG
       GGAGTCCATG GAGTAACTCC TCGACCAGTT GTAGTGGGTC TTGGTCTTCC GAGGCGAGAC

· N  G  S    M  V  W  S  I  N  L    T  A  G    M  Y  C  A    A  L  E
 841   CAATGGCAGC ATGGTATGGA GCATCAACCT GACAGCTGGC ATGTACTGTG CAGCCCTGGA
       GTTACCGTCG TACCATACCT CGTAGTTGGA CTGTCGACCG TACATGACAC GTCGGGACCT

· S  L  I    N  V  S  G  C  S  A    I  E  K    T  Q  R  M    L  S  G
 901   ATCCCTGATC AACGTGTCAG GCTGCAGTGC CATCGAGAAG ACCCAGAGGA TGCTGAGCGG
       TAGGGACTAG TTGCACAGTC CGACGTCACG GTAGCTCTTC TGGGTCTCCT ACGACTCGCC

· F  C  P    H  K  V  S  A  G  Q    F  S  S    L  H  V  R    D  T  K
 961   ATTCTGCCCG CACAAGGTCT CAGCTGGGCA GTTTTCCAGC TTGCATGTCC GAGACACCAA
       TAAGACGGGC GTGTTCCAGA GTCGACCCGT CAAAAGGTCG AACGTACAGG CTCTGTGGTT

· I  E  V    A  Q  F  V  K  D  L    L  H    L  K  K  L    F  R  E
1021   AATCGAGGTG GCCCAGTTTG TAAAGGACCT GCTCTTACAT TTAAAGAAAC TTTTTCGCGA
       TTAGCTCCAC CGGGTCAAAC ATTTCCTGGA CGAGAATGTA AATTTCTTTG AAAAAGCGCT

· G  R  F    N  E  S  K    Y  G  P    P  C  P    P  C  P  A    P  E  F
1081   GGGACGGTTC AACGAGTCCA AATATGGTCC CCCATGCCCA CCATGCCCAG CACCTGAGTT
       CCCTGCCAAG TTGCTCAGGT TTATACCAGG GGGTACGGGT GGTACGGGTC GTGGACTCAA

· L  G  G    P  S  V  F    L  F  P    P  K  P    K  D  T  L    M  I  S
1141   CCTGGGGGGA CCATCAGTCT TCCTGTTCCC CCCAAAACCC AAGGACACTC TCATGATCTC
       GGACCCCCCT GGTAGTCAGA AGGACAAGGG GGGTTTTGGG TTCCTGTGAG AGTACTAGAG

· R  T  P    E  V  T  C    V  V  V    D  V  S    Q  E  D  P    E  V  Q
1201   CCGGACCCCT GAGGTCACGT GCGTGGTGGT GGACGTGAGC CAGGAAGACC CCGAGGTCCA
       GGCCTGGGGA CTCCAGTGCA CGCACCACCA CCTGCACTCG GTCCTTCTGG GGCTCCAGGT

· F  N  W    Y  V  D  G    V  E  V    H  N  A    K  T  K  P    R  E  E
1261   GTTCAACTGG TACGTGGATG GCGTGGAGGT GCATAATGCC AAGACAAAGC CGCGGGAGGA
       CAAGTTGACC ATGCACCTAC CGCACCTCCA CGTATTACGG TTCTGTTTCG GCGCCCTCCT

· Q  F  N    S  T  Y  R    V  V  S    V  L  T    V  L  H  Q    D  W  L
1321   GCAGTTCAAC AGCACGTACC GTGTGGTCAG CGTCCTCACC GTCCTGCACC AGGACTGGCT
       CGTCAAGTTG TCGTGCATGG CACACCAGTC GCAGGAGTGG CAGGACGTGG TCCTGACCGA

· N  G  K    E  Y  K  C    K  V  S    N  K  G    L  P  S  S    I  E  K
1381   GAACGGCAAG GAGTACAAGT GCAAGGTCTC CAACAAAGGC CTCCCGTCCT CCATCGAGAA
       CTTGCCGTTC CTCATGTTCA CGTTCCAGAG GTTGTTTCCG GAGGGCAGGA GGTAGCTCTT
```

FIG. 12B

```
       · T  I  S   K  A  K  G   Q  P  R   E  P  Q   V  Y  T   L  P  P  S
1441   AACCATCTCC AAAGCCAAAG GGCAGCCCCG AGAGCCACAG GTGTACACCC TGCCCCCATC
       TTGGTAGAGG TTTCGGTTTC CCGTCGGGGC TCTCGGTGTC CACATGTGGG ACGGGGGTAG

· Q  E  E   M  T  K  N   Q  V  S   L  T  C   L  V  K  G   F  Y  P
1501   CCAGGAGGAG ATGACCAAGA ACCAGGTCAG CCTGACCTGC CTGGTCAAAG GCTTCTACCC
       GGTCCTCCTC TACTGGTTCT TGGTCCAGTC GGACTGGACG GACCAGTTTC CGAAGATGGG

· S  D  I   A  V  E  W   E  S  N   G  Q  P   E  N  N  Y   K  T  T
1561   CAGCGACATC GCCGTGGAGT GGGAGAGCAA TGGGCAGCCG GAGAACAACT ACAAGACCAC
       GTCGCTGTAG CGGCACCTCA CCCTCTCGTT ACCCGTCGGC CTCTTGTTGA TGTTCTGGTG

· P  P  V   L  D  S  D   G  S  F   F  L  Y   S  R  L  T   V  D  K
1621   GCCTCCCGTG CTGGACTCCG ACGGCTCCTT CTTCCTCTAC AGCAGGCTAA CCGTGGACAA
       CGGAGGGCAC GACCTGAGGC TGCCGAGGAA GAAGGAGATG TCGTCCGATT GGCACCTGTT

· S  R  W   Q  E  G  N   V  F  S   C  S  V   M  H  E  A   L  H  N
1681   GAGCAGGTGG CAGGAGGGGA ATGTCTTCTC ATGCTCCGTG ATGCATGAGG CTCTGCACAA
       CTCGTCCACC GTCCTCCCCT TACAGAAGAG TACGAGGCAC TACGTACTCC GAGACGTGTT

· H  Y  T   Q  K  S  L   S  L  S   L  G  K   M  A  L  I   V  L  G
1741   CCACTACACA CAGAAGAGCC TCTCCCTGTC CCTAGGTAAA ATGGCCCTGA TTGTGCTGGG
       GGTGATGTGT GTCTTCTCGG AGAGGGACAG GGATCCATTT TACCGGGACT AACACGACCC

· G  V  A   G  L  L  L   F  I  G   L  G  I   F  F  R  V   K  F  S
1801   GGGCGTCGCC GGCCTCCTGC TTTTCATTGG GCTAGGCATC TTCTTCAGAG TGAAGTTCAG
       CCCGCAGCGG CCGGAGGACG AAAAGTAACC CGATCCGTAG AAGAAGTCTC ACTTCAAGTC

· R  S  A   D  A  P  A   Y  Q  Q   G  Q  N   Q  L  Y  N   E  L  N
1861   CAGGAGCGCA GACGCCCCCG CGTACCAGCA GGGCCAGAAC CAGCTCTATA ACGAGCTCAA
       GTCCTCGCGT CTGCGGGGGC GCATGGTCGT CCCGGTCTTG GTCGAGATAT TGCTCGAGTT

· L  G  R   R  E  E  Y   D  V  L   D  K  R   R  G  R  D   P  E  M
1921   TCTAGGACGA AGAGAGGAGT ACGATGTTTT GGACAAGAGA CGTGGCCGGG ACCCTGAGAT
       AGATCCTGCT TCTCTCCTCA TGCTACAAAA CCTGTTCTCT GCACCGGCCC TGGGACTCTA

· G  G  K   P  R  R  K   N  P  Q   E  G  L   Y  N  E  L   Q  K  D
1981   GGGGGGAAAG CCGAGAAGGA AGAACCCTCA GGAAGGCCTG TACAATGAAC TGCAGAAAGA
       CCCCCCTTTC GGCTCTTCCT TCTTGGGAGT CCTTCCGGAC ATGTTACTTG ACGTCTTTCT

· K  M  A   E  A  Y  S   E  I  G   M  K  G   E  R  R  R   G  K  G
2041   TAAGATGGCG GAGGCCTACA GTGAGATTGG GATGAAAGGC GAGCGCCGGA GGGGCAAGGG
       ATTCTACCGC CTCCGGATGT CACTCTAACC CTACTTTCCG CTCGCGGCCT CCCCGTTCCC

· H  D  G   L  Y  Q  G   L  S  T   A  T  K   D  T  Y  D   A  L  H
2101   GCACGATGGC CTTTACCAGG GTCTCAGTAC AGCCACCAAG GACACCTACG ACGCCCTTCA
       CGTGCTACCG GAAATGGTCC CAGAGTCATG TCGGTGGTTC CTGTGGATGC TGCGGGAAGT
```

FIG. 12C

```
                  · M   Q   A   L   P   P   R   *
2161    CATGCAGGCC CTGCCCCCTC GCTGAGCGGC CGGCGAAGGA GGCCTAGATC TATCGATTGT
        GTACGTCCGG GACGGGGGAG CGACTCGCCG GCCGCTTCCT CCGGATCTAG ATAGCTAACA (late SV40pAN▶)
2221    ACAGCTAGCT CGACATGATA AGATACATTG ATGAGTTTGG ACAAACCACA ACTAGAATGC
        TGTCGATCGA GCTGTACTAT TCTATGTAAC TACTCAAACC TGTTTGGTGT TGATCTTACG 2281    AGTGAAAAAA ATGCTTTATT TGTGAAATTT GTGATGCTAT TGCTTTATTT GTGAAATTTG
        TCACTTTTTT TACGAAATAA ACACTTTAAA CACTACGATA ACGAAATAAA CACTTTAAAC 2341    TGATGCTATT GCTTTATTTG TAACCATTAT AAGCTGCAAT AAACAAGTTA ACAACAACAA
        ACTACGATAA CGAAATAAAC ATTGGTAATA TTCGACGTTA TTTGTTCAAT TGTTGTTGTT 2401    TTGCATTCAT TTTATGTTTC AGGTTCAGGG GGAGGTGTGG GAGGTTTTTT AAAGCAAGTA
        AACGTAAGTA AAATACAAAG TCCAAGTCCC CCTCCACACC CTCCAAAAAA TTTCGTTCAT (ori ColE1▶)
2461    AAACCTCTAC AAATGTGGTA GATCCATTTA AATGTTAGCG AAGAACATGT GAGCAAAAGG
        TTTGGAGATG TTTACACCAT CTAGGTAAAT TTACAATCGC TTCTTGTACA CTCGTTTTCC 2521    CCAGCAAAAG GCCAGGAACC GTAAAAAGGC CGCGTTGCTG GCGTTTTTCC ATAGGCTCCG
        GGTCGTTTTC CGGTCCTTGG CATTTTTCCG GCGCAACGAC CGCAAAAAGG TATCCGAGGC 2581    CCCCCCTGAC GAGCATCACA AAAATCGACG CTCAAGTCAG AGGTGGCGAA ACCCGACAGG
        GGGGGGACTG CTCGTAGTGT TTTTAGCTGC GAGTTCAGTC TCCACCGCTT TGGGCTGTCC 2641    ACTATAAAGA TACCAGGCGT TTCCCCCTGG AAGCTCCCTC GTGCGCTCTC CTGTTCCGAC
        TGATATTTCT ATGGTCCGCA AAGGGGGACC TTCGAGGGAG CACGCGAGAG GACAAGGCTG 2701    CCTGCCGCTT ACCGGATACC TGTCCGCCTT TCTCCCTTCG GGAAGCGTGG CGCTTTCTCA
        GGACGGCGAA TGGCCTATGG ACAGGCGGAA AGAGGGAAGC CCTTCGCACC GCGAAAGAGT 2761    ATGCTCACGC TGTAGGTATC TCAGTTCGGT GTAGGTCGTT CGCTCCAAGC TGGGCTGTGT
        TACGAGTGCG ACATCCATAG AGTCAAGCCA CATCCAGCAA GCGAGGTTCG ACCCGACACA 2821    GCACGAACCC CCCGTTCAGC CCGACCGCTG CGCCTTATCC GGTAACTATC GTCTTGAGTC
        CGTGCTTGGG GGGCAAGTCG GGCTGGCGAC GCGGAATAGG CCATTGATAG CAGAACTCAG 2881    CAACCCGGTA AGACACGACT TATCGCCACT GGCAGCAGCC ACTGGTAACA GGATTAGCAG
        GTTGGGCCAT TCTGTGCTGA ATAGCGGTGA CCGTCGTCGG TGACCATTGT CCTAATCGTC 2941    AGCGAGGTAT GTAGGCGGTG CTACAGAGTT CTTGAAGTGG TGGCCTAACT ACGGCTACAC
        TCGCTCCATA CATCCGCCAC GATGTCTCAA GAACTTCACC ACCGGATTGA TGCCGATGTG
```

FIG. 12D

```
3001    TAGAAGAACA GTATTTGGTA TCTGCGCTCT GCTGAAGCCA GTTACCTTCG GAAAAAGAGT
        ATCTTCTTGT CATAAACCAT AGACGCGAGA CGACTTCGGT CAATGGAAGC CTTTTTCTCA

3061    TGGTAGCTCT TGATCCGGCA AACAAACCAC CGCTGGTAGC GGTGGTTTTT TTGTTTGCAA
        ACCATCGAGA ACTAGGCCGT TTGTTTGGTG GCGACCATCG CCACCAAAAA AACAAACGTT

3121    GCAGCAGATT ACGCGCAGAA AAAAGGATC TCAAGAAGAT CCTTTGATCT TTTCTACGGG
        CGTCGTCTAA TGCGCGTCTT TTTTTCCTAG AGTTCTTCTA GGAAACTAGA AAAGATGCCC

PacI
3181    GTCTGACGCT CAGTGGAACG AAAACTCACG TTAAGGGATT TTGGTCATGG CTAGTTAATT
        CAGACTGCGA GTCACCTTGC TTTTGAGTGC AATTCCCTAA AACCAGTACC GATCAATTAA

PacI
              (SpAn)
3241    AAGCTGCAAT AAACAATCAT TATTTTCATT GGATCTGTGT GTTGGTTTTT TGTGTGGGCT
        TTCGACGTTA TTTGTTAGTA ATAAAAGTAA CCTAGACACA CAACCAAAAA ACACACCCGA

3301    TGGGGGAGGG GGAGGCCAGA ATGACTCCAA GAGCTACAGG AAGGCAGGTC AGAGACCCCA
        ACCCCCTCCC CCTCCGGTCT TACTGAGGTT CTCGATGTCC TTCCGTCCAG TCTCTGGGGT

3361    CTGGACAAAC AGTGGCTGGA CTCTGCACCA TAACACACAA TCAACAGGGG AGTGAGCTGG
        GACCTGTTTG TCACCGACCT GAGACGTGGT ATTGTGTGTT AGTTGTCCCC TCACTCGACC (h CMV-1Aprom→)
3421    ATCGAGCTAG AGTCCGTTAC ATAACTTACG GTAAATGGCC CGCCTGGCTG ACCGCCCAAC
        TAGCTCGATC TCAGGCAATG TATTGAATGC CATTTACCGG GCGGACCGAC TGGCGGGTTG 3481    GACCCCCGCC CATTGACGTC AATAATGACG TATGTTCCCA TAGTAACGCC AATAGGGACT
        CTGGGGGCGG GTAACTGCAG TTATTACTGC ATACAAGGGT ATCATTGCGG TTATCCCTGA 3541    TTCCATTGAC GTCAATGGGT GGAGTATTTA CGGTAAACTG CCCACTTGGC AGTACATCAA
        AAGGTAACTG CAGTTACCCA CCTCATAAAT GCCATTTGAC GGGTGAACCG TCATGTAGTT 3601    GTGTATCATA TGCCAAGTAC GCCCCCTATT GACGTCAATG ACGGTAAATG GCCCGCCTGG
        CACATAGTAT ACGGTTCATG CGGGGGATAA CTGCAGTTAC TGCCATTTAC CGGGCGGACC 3661    CATTATGCCC AGTACATGAC CTTATGGGAC TTTCCTACTT GGCAGTACAT CTACGTATTA
        GTAATACGGG TCATGTACTG GAATACCCTG AAAGGATGAA CCGTCATGTA GATGCATAAT 3721    GTCATCGCTA TTACCATGGT GATGCGGTTT TGGCAGTACA TCAATGGGCG TGGATAGCGG
        CAGTAGCGAT AATGGTACCA CTACGCCAAA ACCGTCATGT AGTTACCCGC ACCTATCGCC 3781    TTTGACTCAC GGGGATTTCC AAGTCTCCAC CCCATTGACG TCAATGGGAG TTTGTTTTGG
        AAACTGAGTG CCCCTAAAGG TTCAGAGGTG GGGTAACTGC AGTTACCCTC AAACAAAACC
```

FIG. 12E

```
3841  CACCAAAATC AACGGGACTT TCCAAAATGT CGTAACAACT CCGCCCCATT GACGCAAATG
      GTGGTTTTAG TTGCCCTGAA AGGTTTTACA GCATTGTTGA GGCGGGGTAA CTGCGTTTAC

3901  GGCGGTAGGC GTGTACGGTG GGAGGTCTAT ATAAGCAGAG CTCGTTTAGT GAACCGTCAG
      CCGCCATCCG CACATGCCAC CCTCCAGATA TATTCGTCTC GAGCAAATCA CTTGGCAGTC

3961  ATCGCCTGGA GACGCCATCC ACGCTGTTTT GACCTCCATA GAAGACACCG GGACCGATCC
      TAGCGGACCT CTGCGGTAGG TGCGACAAAA CTGGAGGTAT CTTCTGTGGC CCTGGCTAGG

4021  AGCCTCCGCG GCCGGGAACG GTGCATTGGA ACGCGGATTC CCCGTGCCAA GAGTGACGTA
      TCGGAGGCGC CGGCCCTTGC CACGTAACCT TGCGCCTAAG GGGCACGGTT CTCACTGCAT

4081  AGTACCGCCT ATAGAGTCTA TAGGCCCACC TAGTTGTGAC CGGCGCCTAG TGTTGACAAT
      TCATGGCGGA TATCTCAGAT ATCCGGGTGG ATCAACACTG GCCGCGGATC ACAACTGTTA

4141  TAATCATCGG CATAGTATAT CGGCATAGTA TAATACGACT CACTATAGGA GGGCCACCAT
      ATTAGTAGCC GTATCATATA GCCGTATCAT ATTATGCTGA GTGATATCCT CCCGGTGGTA (HyTK→)
                                                                 M
4201  GTCGACTACT AACCTTCTTC TCTTTCCTAC AGCTGAGATC ACCGGTAGGA GGGCCATCAT
      CAGCTGATGA TTGGAAGAAG AGAAAGGATG TCGACTCTAG TGGCCATCCT CCCGGTAGTA

· K  K  P  E  L  T  A  T  S  V  A  K  F  L  I  E  K  F  D  S
4261  GAAAAAGCCT GAACTCACCG CGACGTCTGT CGCGAAGTTT CTGATCGAAA AGTTCGACAG
      CTTTTTCGGA CTTGAGTGGC GCTGCAGACA GCGCTTCAAA GACTAGCTTT TCAAGCTGTC

· V  S  D  L  M  Q  L  S  E  G  E  E  S  R  A  F  S  F  D  V
4321  CGTCTCCGAC CTGATGCAGC TCTCGGAGGG CGAAGAATCT CGTGCTTTCA GCTTCGATGT
      GCAGAGGCTG GACTACGTCG AGAGCCTCCC GCTTCTTAGA GCACGAAAGT CGAAGCTACA

· G  G  R  G  Y  V  L  R  V  N  S  C  A  D  G  F  Y  K  D  R
4381  AGGAGGGCGT GGATATGTCC TGCGGGTAAA TAGCTGCGCC GATGGTTTCT ACAAAGATCG
      TCCTCCCGCA CCTATACAGG ACGCCCATTT ATCGACGCGG CTACCAAAGA TGTTTCTAGC

· Y  V  Y  R  H  F  A  S  A  A  L  P  I  P  E  V  L  D  I  G
4441  TTATGTTTAT CGGCACTTTG CATCGGCCGC GCTCCCGATT CCGGAAGTGC TTGACATTGG
      AATACAAATA GCCGTGAAAC GTAGCCGGCG CGAGGGCTAA GGCCTTCACG AACTGTAACC

· E  F  S  E  S  L  T  Y  C  I  S  R  R  A  Q  G  V  T  L  Q
4501  GGAATTCAGC GAGAGCCTGA CCTATTGCAT CTCCCGCCGT GCACAGGGTG TCACGTTGCA
      CCTTAAGTCG CTCTCGGACT GGATAACGTA GAGGGCGGCA CGTGTCCCAC AGTGCAACGT

· D  L  P  E  T  E  L  P  A  V  L  Q  P  V  A  E  L  M  D  A
4561  AGACCTGCCT GAAACCGAAC TGCCCGCTGT TCTGCAACCC GTCGCGGAGC TCATGGATGC
      TCTGGACGGA CTTTGGCTTG ACGGGCGACA AGACGTTGGG CAGCGCCTCG AGTACCTACG
```

FIG. 12F

```
              · I  A  A     A  D  L  S     Q  T  S     G  F  G     P  F  G     P  Q  G  I
      4621    GATCGCTGCG GCCGATCTTA GCCAGACGAG CGGGTTCGGC CCATTCGGAC CGCAAGGAAT
              CTAGCGACGC CGGCTAGAAT CGGTCTGCTC GCCCAAGCCG GGTAAGCCTG GCGTTCCTTA

· G  Q  Y     T  T  W  R     D  F  I     C  A  I     A  D  P     H  V  Y  H
      4681    CGGTCAATAC ACTACATGGC GTGATTTCAT ATGCGCGATT GCTGATCCCC ATGTGTATCA
              GCCAGTTATG TGATGTACCG CACTAAAGTA TACGCGCTAA CGACTAGGGG TACACATAGT

· W  Q  T     V  M  D  D     T  V  S     A  S  V     A  Q  A     L  D  E  L
      4741    CTGGCAAACT GTGATGGACG ACACCGTCAG TGCGTCCGTC GCGCAGGCTC TCGATGAGCT
              GACCGTTTGA CACTACCTGC TGTGGCAGTC ACGCAGGCAG CGCGTCCGAG AGCTACTCGA

· M  L  W     A  E  D  C     P  E  V     R  H  L     V  H  A     D  F  G  S
      4801    GATGCTTTGG GCCGAGGACT GCCCCGAAGT CCGGCACCTC GTGCACGCGG ATTTCGGCTC
              CTACGAAACC CGGCTCCTGA CGGGGCTTCA GGCCGTGGAG CACGTGCGCC TAAAGCCGAG

· N  N  V     L  T  D  N     G  R  I     T  A  V     I  D  W     S  E  A  M
      4861    CAACAATGTC CTGACGGACA ATGGCCGCAT AACAGCGGTC ATTGACTGGA GCGAGGCGAT
              GTTGTTACAG GACTGCCTGT TACCGGCGTA TTGTCGCCAG TAACTGACCT CGCTCCGCTA

· F  G  D     S  Q  Y  E     V  A  N     I  F  F     W  R  P     W  L  A  C
      4921    GTTCGGGGAT TCCCAATACG AGGTCGCCAA CATCTTCTTC TGGAGGCCGT GGTTGGCTTG
              CAAGCCCCTA AGGGTTATGC TCCAGCGGTT GTAGAAGAAG ACCTCCGGCA CCAACCGAAC

· M  E  Q     Q  T  R  Y     F  E  R     R  H  P     E  L  A     G  S  P  R
      4981    TATGGAGCAG CAGACGCGCT ACTTCGAGCG GAGGCATCCG GAGCTTGCAG GATCGCCGCG
              ATACCTCGTC GTCTGCGCGA TGAAGCTCGC CTCCGTAGGC CTCGAACGTC CTAGCGGCGC

· L  R  A     Y  M  L  R     I  G  L     D  Q  L     Y  Q  S     L  V  D  G
      5041    GCTCCGGGCG TATATGCTCC GCATTGGTCT TGACCAACTC TATCAGAGCT TGGTTGACGG
              CGAGGCCCGC ATATACGAGG CGTAACCAGA ACTGGTTGAG ATAGTCTCGA ACCAACTGCC

· N  F  D     D  A  A  W     A  Q  G     R  C  D     A  I  V     R  S  G  A
      5101    CAATTTCGAT GATGCAGCTT GGGCGCAGGG TCGATGCGAC GCAATCGTCC GATCCGGAGC
              GTTAAAGCTA CTACGTCGAA CCCGCGTCCC AGCTACGCTG CGTTAGCAGG CTAGGCCTCG

· G  T  V     G  R  T  Q     I  A  R     R  S  A     A  V  W     T  D  G  C
      5161    CGGGACTGTC GGGCGTACAC AAATCGCCCG CAGAAGCGCG GCCGTCTGGA CCGATGGCTG
              GCCCTGACAG CCCGCATGTG TTTAGCGGGC GTCTTCGCGC CGGCAGACCT GGCTACCGAC

· V  E  V     A  S  A  F     D  Q  A     A  R  S     R  G  H     S  N  R  R
      5221    TGTAGAAGTC GCGTCTGCGT TCGACCAGGC TGCGCGTTCT CGCGGCCATA GCAACCGACG
              ACATCTTCAG CGCAGACGCA AGCTGGTCCG ACGCGCAAGA GCGCCGGTAT CGTTGGCTGC

· T  A  L     R  P  R  R     Q  Q  E     A  T  E     V  R  P     E  Q  K  M
      5281    TACGGCGTTG CGCCCTCGCC GGCAGCAAGA AGCCACGGAA GTCCGCCCGG AGCAGAAAAT
              ATGCCGCAAC GCGGGAGCGG CCGTCGTTCT TCGGTGCCTT CAGGCGGGCC TCGTCTTTTA
```

FIG. 12G

```
              · P   T   L    L   R   V   Y    I   D   G    P   H   G    M   G   K   T   T   T   T
       5341   GCCCACGCTA   CTGCGGGTTT   ATATAGACGG   TCCCCACGGG   ATGGGGAAAA   CCACCACCAC
              CGGGTGCGAT   GACGCCCAAA   TATATCTGCC   AGGGGTGCCC   TACCCCTTTT   GGTGGTGGTG

· Q   L   L    V   A   L   G    S   R   D    D   I   V    Y   V   P   E   P   M   T
       5401   GCAACTGCTG   GTGGCCCTGG   GTTCGCGCGA   CGATATCGTC   TACGTACCCG   AGCCGATGAC
              CGTTGACGAC   CACCGGGACC   CAAGCGCGCT   GCTATAGCAG   ATGCATGGGC   TCGGCTACTG

· Y   W   R    V   L   G   A    S   E   T    I   A   N    I   Y   T   T   Q   H   R
       5461   TTACTGGCGG   GTGCTGGGGG   CTTCCGAGAC   AATCGCGAAC   ATCTACACCA   CACAACACCG
              AATGACCGCC   CACCGACCCC   GAAGGCTCTG   TTAGCGCTTG   TAGATGTGGT   GTGTTGTGGC

· L   D   Q    G   E   I   S    A   G   D    A   A   V    V   M   T   S   A   Q   I
       5521   CCTCGACCAG   GGTGAGATAT   CGGCCGGGGA   CGCGGCGGTG   GTAATGACAA   GCGCCCAGAT
              GGAGCTGGTC   CCACTCTATA   GCCGGCCCCT   GCGCCGCCAC   CATTACTGTT   CGCGGGTCTA

· T   M   G    M   P   Y   A    V   T   D    A   V   L    A   P   H   I   G   G   E
       5581   AACAATGGGC   ATGCCTTATG   CCGTGACCGA   CGCCGTTCTG   GCTCCTCATA   TCGGGGGGGA
              TTGTTACCCG   TACGGAATAC   GGCACTGGCT   GCGGCAAGAC   CGAGGAGTAT   AGCCCCCCCT

· A   G   S    S   H   A   P    P   P   A    L   T   L    I   F   D   R   H   P   I
       5641   GGCTGGGAGC   TCACATGCCC   CGCCCCCGGC   CCTCACCCTC   ATCTTCGACC   GCCATCCCAT
              CCGACCCTCG   AGTGTACGGG   GCGGGGGCCG   GGAGTGGGAG   TAGAAGCTGG   CGGTAGGGTA

· A   A   L    C   Y   P   A    A   R   Y    L   M   G    S   M   T   P   Q   A
       5701   CGCCGCCCTC   CTGTGCTACC   CGGCCGCGCG   GTACCTTATG   GGCAGCATGA   CCCCCCAGGC
              GCGGCGGGAG   GACACGATGG   GCCGGCGCGC   CATGGAATAC   CCGTCGTACT   GGGGGGTCCG

· V   L   A    F   V   A   L    I   P   P    T   L   P    G   T   N   I   V   L   G
       5761   CGTGCTGGCG   TTCGTGGCCC   TCATCCCGCC   GACCTTGCCC   GGCACCAACA   TCGTGCTTGG
              GCACGACCGC   AAGCACCGGG   AGTAGGGCGG   CTGGAACGGG   CCGTGGTTGT   AGCACGAACC

· A   L   P    E   D   R   H    I   D   R    L   A   K    R   Q   R   P   G   E   R
       5821   GGCCCTTCCG   GAGGACAGAC   ACATCGACCG   CCTGGCCAAA   CGCCAGCGCC   CCGGCGAGCG
              CCGGGAAGGC   CTCCTGTCTG   TGTAGCTGGC   GGACCGGTTT   GCGGTCGCGG   GGCCGCTCGC

· L   D   L    A   M   L   A    A   I   R    R   V   Y    G   L   L   A   N   T   V
       5881   GCTGGACCTG   GCTATGCTGG   CTGCGATTCG   CCGCGTTTAC   GGGCTACTTG   CCAATACGGT
              CGACCTGGAC   CGATACGACC   GACGCTAAGC   GGCGCAAATG   CCCGATGAAC   GGTTATGCCA

· R   Y   L    Q   C   G   G    S   W   R    E   D   W    G   Q   L   S   G   T   A
       5941   GCGGTATCTG   CAGTGCGGCG   GGTCGTGGCG   GGAGGACTGG   GGACAGCTTT   CGGGGACGGC
              CGCCATAGAC   GTCACGCCGC   CCAGCACCGC   CCTCCTGACC   CCTGTCGAAA   GCCCCTGCCG

· V   P   P    Q   G   A   E    P   Q   S    N   A   G    P   R   P   H   I   G   D
       6001   CGTGCCGCCC   CAGGGTGCCG   AGCCCCAGAG   CAACGCGGGC   CCACGACCCC   ATATCGGGGA
              GCACGGCGGG   GTCCCACGGC   TCGGGGTCTC   GTTGCGCCCG   GGTGCTGGGG   TATAGCCCCT
```

FIG. 12H

```
              · T  L  F    T  L  F  R    A  P  E       L  L  A    P  N  G  D  L  Y  N
       6061   CACGTTATTT   ACCCTGTTTC    GGGCCCCCGA    GTTGCTGGCC  CCCAACGGCG  ACCTGTATAA
              GTGCAATAAA   TGGGACAAAG    CCCGGGGGCT    CAACGACCGG  GGGTTGCCGC  TGGACATATT

· V  F  A    W  A  L  D    V  L  A       K  R  L    R  S  M  H  V  F  I
       6121   CGTGTTTGCC   TGGGCCTTGG    ACGTCTTGGC    CAAACGCCTC  CGTTCCATGC  ACGTCTTTAT
              GCACAAACGG   ACCCGGAACC    TGCAGAACCG    GTTTGCGGAG  GCAAGGTACG  TGCAGAAATA

· L  D  Y    D  Q  S    P  A  G  C       R  D  A    L  L  Q  L  T  S  G
       6181   CCTGGATTAC   GACCAATCGC    CCGCCGGCTG    CCGGGACGCC  CTGCTGCAAC  TTACCTCCGG
              GGACCTAATG   CTGGTTAGCG    GGCGGCCGAC    GGCCCTGCGG  GACGACGTTG  AATGGAGGCC

· M  V  Q    T  H  V  T    T  P  G       S  I  P    T  I  C  D  L  A  R
       6241   GATGGTCCAG   ACCCACGTCA    CCACCCCCGG    CTCCATACCG  ACGATATGCG  ACCTGGCGCG
              CTACCAGGTC   TGGGTGCAGT    GGTGGGGGCC    GAGGTATGGC  TGCTATACGC  TGGACCGCGC

· T  F  A    R  E  M  G    E  A  N       * (bGh pA→)
       6301   CACGTTTGCC   CGGGAGATGG    GGGAGGCTAA    CTGAGTCGAG  AATTCGCTAG  AGGGCCCTAT
              GTGCAAACGG   GCCCTCTACC    CCCTCCGATT    GACTCAGCTC  TTAAGCGATC  TCCCGGGATA

6361   TCTATAGTGT   CACCTAAATG    CTAGAGCTCG    CTGATCAGCC  TCGACTGTGC  CTTCTAGTTG
              AGATATCACA   GTGGATTTAC    GATCTCGAGC    GACTAGTCGG  AGCTGACACG  GAAGATCAAC

6421   CCAGCCATCT   GTTGTTTGCC    CCTCCCCCGT    GCCTTCCTTG  ACCCTGGAAG  GTGCCACTCC
              GGTCGGTAGA   CAACAAACGG    GGAGGGGGCA    CGGAAGGAAC  TGGGACCTTC  CACGGTGAGG

6481   CACTGTCCTT   TCCTAATAAA    ATGAGGAAAT    TGCATCGCAT  TGTCTGAGTA  GGTGTCATTC
              GTGACAGGAA   AGGATTATTT    TACTCCTTTA    ACGTAGCGTA  ACAGACTCAT  CCACAGTAAG

6541   TATTCTGGGG   GGTGGGGTGG    GGCAGGACAG    CAAGGGGGAG  GATTGGGAAG  ACAATAGCAG
              ATAAGACCCC   CCACCCCACC    CCGTCCTGTC    GTTCCCCCTC  CTAACCCTTC  TGTTATCGTC

6601   GCATGCGCAG   GGCCCAATTG    CTCGAGCGGC    CGCAATAAAA  TATCTTTATT  TTCATTACAT
              CGTACGCGTC   CCGGGTTAAC    GAGCTCGCCG    GCGTTATTTT  ATAGAAATAA  AAGTAATGTA

6661   CTGTGTGTTG   GTTTTTTGTG    TGAATCGTAA    CTAACATACG  CTCTCCATCA  AAACAAAACG
              GACACACAAC   CAAAAAACAC    ACTTAGCATT    GATTGTATGC  GAGAGGTAGT  TTTGTTTTGC

6721   AAACAAAACA   AACTAGCAAA    ATAGGCTGTC    CCCAGTGCAA  GTGCAGGTGC  CAGAACATTT
              TTTGTTTTGT   TTGATCGTTT    TATCCGACAG    GGGTCACGTT  CACGTCCACG  GTCTTGTAAA

6781   CTCTA
              GAGAT
```

FIG. 12I

```
        (hEF1p→)
  1   TCGAAGGATC TGCGATCGCT CCGGTGCCCG TCAGTGGGCA GAGCGCACAT CGCCCACAGT
      AGCTTCCTAG ACGCTAGCGA GGCCACGGGC AGTCACCCGT CTCGCGTGTA GCGGGTGTCA

61   CCCCGAGAAG TTGGGGGGAG GGGTCGGCAA TTGAACCGGT GCCTAGAGAA GGTGGCGCGG
      GGGGCTCTTC AACCCCCCTC CCCAGCCGTT AACTTGGCCA CGGATCTCTT CCACCGCGCC

121   GGTAAACTGG GAAAGTGATG TCGTGTACTG GCTCCGCCTT TTTCCCGAGG GTGGGGGAGA
      CCATTTGACC CTTTCACTAC AGCACATGAC CGAGGCGGAA AAAGGGCTCC CACCCCCTCT

181   ACCGTATATA AGTGCAGTAG TCGCCGTGAA CGTTCTTTTT CGCAACGGGT TTGCCGCCAG
      TGGCATATAT TCACGTCATC AGCGGCACTT GCAAGAAAAA GCGTTGCCCA AACGGCGGTC

241   AACACAGCTG AAGCTTCGAG GGGCTCGCAT CTCTCCTTCA CGCGCCCGCC GCCCTACCTG
      TTGTGTCGAC TTCGAAGCTC CCCGAGCGTA GAGAGGAAGT GCGCGGGCGG CGGGATGGAC

301   AGGCCGCCAT CCACGCCGGT TGAGTCGCGT TCTGCCGCCT CCCGCCTGTG GTGCCTCCTG
      TCCGGCGGTA GGTGCGGCCA ACTCAGCGCA AGACGGCGGA GGGCGGACAC CACGGAGGAC

361   AACTGCGTCC GCCGTCTAGG TAAGTTTAAA GCTCAGGTCG AGACCGGGCC TTTGTCCGGC
      TTGACGCAGG CGGCAGATCC ATTCAAATTT CGAGTCCAGC TCTGGCCCGG AAACAGGCCG

421   GCTCCCTTGG AGCCTACCTA GACTCAGCCG GCTCTCCACG CTTTGCCTGA CCCTGCTTGC
      CGAGGGAACC TCGGATGGAT CTGAGTCGGC CGAGAGGTGC GAAACGGACT GGGACGAACG

481   TCAACTCTAC GTCTTTGTTT CGTTTTCTGT TCTGCGCCGT TACAGATCCA AGCTGTGACC
      AGTTGAGATG CAGAAACAAA GCAAAAGACA AGACGCGGCA ATGTCTAGGT TCGACACTGG

541   GGCGCCTACG TAAGTGATAT CTACTAGATT TATCAAAAAG AGTGTTGACT TGTGAGCGCT
      CCGCGGATGC ATTCACTATA GATGATCTAA ATAGTTTTTC TCACAACTGA ACACTCGCGA

601   CACAATTGAT ACGGATTCAT CGAGAGGGAC ACGTCGACTA CTAACCTTCT TCTCTTTCCT
      GTGTTAACTA TGCCTAAGTA GCTCTCCCTG TGCAGCTGAT GATTGGAAGA AGAGAAAGGA (IL13zetakine→)
                             M   L   L   V   T   S   L   L   L   C ·
661   ACAGCTGAGA TCACCCTAGA GCCGCCACCA TGCTTCTCCT GGTGACAAGC CTTCTGCTCT
      TGTCGACTCT AGTGGGATCT CGGCGGTGGT ACGAAGAGGA CCACTGTTCG GAAGACGAGA ·  E   L   P   H   P   A   F   L   L   I   P   G   P   V   P   P   S   T   A   L·
721   GTGAGTTACC ACACCCAGCA TTCCTCCTGA TCCCAGGCCC TGTGCCTCCC TCTACAGCCC
      CACTCAATGG TGTGGGTCGT AAGGAGGACT AGGGTCCGGG ACACGGAGGG AGATGTCGGG
```

FIG. 13A

```
           · R  Y  L    I  E  E    L  V  N  I    T  Q  N    Q  K  A    P  L  C  N ·
 781   TCAGGTACCT CATTGAGGAG CTGGTCAACA TCACCCAGAA CCAGAAGGCT CCGCTCTGCA
       AGTCCATGGA GTAACTCCTC GACCAGTTGT AGTGGGTCTT GGTCTTCCGA GGCGAGACGT

· G  S  M    V  W  S    I  N  L  T    A  G  M    Y  C  A    A  L  E  S ·
 841   ATGGCAGCAT GGTATGGAGC ATCAACCTGA CAGCTGGCAT GTACTGTGCA GCCCTGGAAT
       TACCGTCGTA CCATACCTCG TAGTTGGACT GTCGACCGTA CATGACACGT CGGGACCTTA

· L  I  N    V  S  G    C  S  A  I    E  K  T    Q  R  M    L  S  G  F ·
 901   CCCTGATCAA CGTGTCAGGC TGCAGTGCCA TCGAGAAGAC CCAGAGGATG CTGAGCGGAT
       GGGACTAGTT GCACAGTCCG ACGTCACGGT AGCTCTTCTG GGTCTCCTAC GACTCGCCTA

· C  P  H    K  V  S    A  G  Q  F    S  S  L    H  V  R    D  T  K  I ·
 961   TCTGCCCGCA CAAGGTCTCA GCTGGGCAGT TTTCCAGCTT GCATGTCCGA GACACCAAAA
       AGACGGGCGT GTTCCAGAGT CGACCCGTCA AAAGGTCGAA CGTACAGGCT CTGTGGTTTT

· E  V  A    Q  F  V    K  D  L  L    L  H  L    K  K  L    F  R  E  G ·
1021   TCGAGGTGGC CCAGTTTGTA AAGGACCTGC TCTTACATTT AAAGAAACTT TTTCGCGAGG
       AGCTCCACCG GGTCAAACAT TTCCTGGACG AGAATGTAAA TTTCTTTGAA AAAGCGCTCC

· R  F  N    E  S  K    Y  G  P  P    C  P  P    C  P  A    P  E  F  L ·
1081   GACGGTTCAA CGAGTCCAAA TATGGTCCCC CATGCCCACC ATGCCCAGCA CCTGAGTTCC
       CTGCCAAGTT GCTCAGGTTT ATACCAGGGG GTACGGGTGG TACGGGTCGT GGACTCAAGG

· G  G  P    S  V  F    L  F  P  P    K  P  K    D  T  L    M  I  S  R ·
1141   TGGGGGGACC ATCAGTCTTC CTGTTCCCCC CAAAACCCAA GGACACTCTC ATGATCTCCC
       ACCCCCCTGG TAGTCAGAAG GACAAGGGGG GTTTTGGGTT CCTGTGAGAG TACTAGAGGG

· T  P  E    V  T  C    V  V  V  D    V  S  Q    E  D  P    E  V  Q  F ·
1201   GGACCCCTGA GGTCACGTGC GTGGTGGTGG ACGTGAGCCA GGAAGACCCC GAGGTCCAGT
       CCTGGGGACT CCAGTGCACG CACCACCACC TGCACTCGGT CCTTCTGGGG CTCCAGGTCA

· N  W  Y    V  D  G    V  E  V  H    N  A  K    T  K  P    R  E  E  Q ·
1261   TCAACTGGTA CGTGGATGGC GTGGAGGTGC ATAATGCCAA GACAAAGCCG CGGGAGGAGC
       AGTTGACCAT GCACCTACCG CACCTCCACG TATTACGGTT CTGTTTCGGC GCCCTCCTCG

· F  N  S    T  Y  R    V  V  S  V    L  T  V    L  H  Q    D  W  L  N ·
1321   AGTTCAACAG CACGTACCGT GTGGTCAGCG TCCTCACCGT CCTGCACCAG GACTGGCTGA
       TCAAGTTGTC GTGCATGGCA CACCAGTCGC AGGAGTGGCA GGACGTGGTC CTGACCGACT

· G  K  E    Y  K  C    K  V  S  N    K  G  L    P  S  S    I  E  K  T ·
1381   ACGGCAAGGA GTACAAGTGC AAGGTCTCCA ACAAAGGCCT CCCGTCCTCC ATCGAGAAAA
       TGCCGTTCCT CATGTTCACG TTCCAGAGGT TGTTTCCGGA GGGCAGGAGG TAGCTCTTTT
```

FIG. 13B

```
         ·I  S  K    A  K  G    Q  P  R  E    P  Q  V    Y  T  L    P  P  S  Q·
  1441   CCATCTCCAA AGCCAAAGGG CAGCCCCGAG AGCCACAGGT GTACACCCTG CCCCCATCCC
         GGTAGAGGTT TCGGTTTCCC GTCGGGGCTC TCGGTGTCCA CATGTGGGAC GGGGGTAGGG

·E  E  M    T  K  N    Q  V  S  L    T  C  L    V  K  G    F  Y  P  S·
  1501   AGGAGGAGAT GACCAAGAAC CAGGTCAGCC TGACCTGCCT GGTCAAAGGC TTCTACCCCA
         TCCTCCTCTA CTGGTTCTTG GTCCAGTCGG ACTGGACGGA CCAGTTTCCG AAGATGGGGT

·D  I  A    V  E  W    E  S  N  G    Q  P  E    N  N  Y    K  T  T  P·
  1561   GCGACATCGC CGTGGAGTGG GAGAGCAATG GGCAGCCGGA GAACAACTAC AAGACCACGC
         CGCTGTAGCG GCACCTCACC CTCTCGTTAC CCGTCGGCCT CTTGTTGATG TTCTGGTGCG

·P  V  L    D  S  D    G  S  F  F    L  Y  S    R  L  T    V  D  K  S·
  1621   CTCCCGTGCT GGACTCCGAC GGCTCCTTCT TCCTCTACAG CAGGCTAACC GTGGACAAGA
         GAGGGCACGA CCTGAGGCTG CCGAGGAAGA AGGAGATGTC GTCCGATTGG CACCTGTTCT

·R  W  Q    E  G  N    V  F  S  C    S  V  M    H  E  A    L  H  N  H·
  1681   GCAGGTGGCA GGAGGGGAAT GTCTTCTCAT GCTCCGTGAT GCATGAGGCT CTGCACAACC
         CGTCCACCGT CCTCCCCTTA CAGAAGAGTA CGAGGCACTA CGTACTCCGA GACGTGTTGG

·Y  T  Q    K  S  L    S  L  S  L    G  K  M    A  L  I    V  L  G  G·
  1741   ACTACACACA GAAGAGCCTC TCCCTGTCCC TAGGTAAAAT GGCCCTGATT GTGCTGGGGG
         TGATGTGTGT CTTCTCGGAG AGGGACAGGG ATCCATTTTA CCGGGACTAA CACGACCCCC

·V  A  G    L  L  L    F  I  G  L    G  I  F    F  R  V    K  F  S  R·
  1801   GCGTCGCCGG CCTCCTGCTT TTCATTGGGC TAGGCATCTT CTTCAGAGTG AAGTTCAGCA
         CGCAGCGGCC GGAGGACGAA AAGTAACCCG ATCCGTAGAA GAAGTCTCAC TTCAAGTCGT

·S  A  D    A  P  A    Y  Q  Q  G    Q  N  Q    L  Y  N    E  L  N  L·
  1861   GGAGCGCAGA CGCCCCCGCG TACCAGCAGG GCCAGAACCA GCTCTATAAC GAGCTCAATC
         CCTCGCGTCT GCGGGGGCGC ATGGTCGTCC CGGTCTTGGT CGAGATATTG CTCGAGTTAG

·G  R  R    E  E  Y    D  V  L  D    K  R  R    G  R  D    P  E  M  G·
  1921   TAGGACGAAG AGAGGAGTAC GATGTTTTGG ACAAGAGACG TGGCCGGGAC CCTGAGATGG
         ATCCTGCTTC TCTCCTCATG CTACAAAACC TGTTCTCTGC ACCGGCCCTG GGACTCTACC

·G  K  P    R  R  K    N  P  Q  E    G  L  Y    N  E  L    Q  K  D  K·
  1981   GGGGAAAGCC GAGAAGGAAG AACCCTCAGG AAGGCCTGTA CAATGAACTG CAGAAAGATA
         CCCCTTTCGG CTCTTCCTTC TTGGGAGTCC TTCCGGACAT GTTACTTGAC GTCTTTCTAT

·M  A  E    A  Y  S    E  I  G  M    K  G  E    R  R  R    G  K  G  H·
  2041   AGATGGCGGA GGCCTACAGT GAGATTGGGA TGAAAGGCGA GCGCCGGAGG GGCAAGGGGC
         TCTACCGCCT CCGGATGTCA CTCTAACCCT ACTTTCCGCT CGCGGCCTCC CCGTTCCCCG

·D  G  L    Y  Q  G    L  S  T  A    T  K  D    T  Y  D    A  L  H  M·
  2101   ACGATGGCCT TTACCAGGGT CTCAGTACAG CCACCAAGGA CACCTACGAC GCCCTTCACA
         TGCTACCGGA AATGGTCCCA GAGTCATGTC GGTGGTTCCT GTGGATGCTG CGGGAAGTGT
```

FIG. 13C

```
           .  Q   A   L   P   P   R   *
2161    TGCAGGCCCT GCCCCCTCGC TGAGCGGCCG GCGAAGGAGG CCTAGATCTA TCGATTGTAC
        ACGTCCGGGA CGGGGGAGCG ACTCGCCGGC CGCTTCCTCC GGATCTAGAT AGCTAACATG (Late SV40pAn→)
2221    AGCTAGCTCG ACATGATAAG ATACATTGAT GAGTTTGGAC AAACCACAAC TAGAATGCAG
        TCGATCGAGC TGTACTATTC TATGTAACTA CTCAAACCTG TTTGGTGTTG ATCTTACGTC 2281    TGAAAAAAAT GCTTTATTTG TGAAATTTGT GATGCTATTG CTTTATTTGT GAAATTTGTG
        ACTTTTTTTA CGAAATAAAC ACTTTAAACA CTACGATAAC GAAATAAACA CTTTAAACAC 2341    ATGCTATTGC TTTATTTGTA ACCATTATAA GCTGCAATAA ACAAGTTAAC AACAACAATT
        TACGATAACG AAATAAACAT TGGTAATATT CGACGTTATT TGTTCAATTG TTGTTGTTAA 2401    GCATTCATTT TATGTTTCAG GTTCAGGGGG AGGTGTGGGA GGTTTTTTAA AGCAAGTAAA
        CGTAAGTAAA ATACAAAGTC CAAGTCCCCC TCCACACCCT CCAAAAAATT TCGTTCATTT (Ori ColE1→)
2461    ACCTCTACAA ATGTGGTAGA TCCATTTAAA TGTTAGCGAA GAACATGTGA GCAAAAGGCC
        TGGAGATGTT TACACCATCT AGGTAAATTT ACAATCGCTT CTTGTACACT CGTTTTCCGG 2521    AGCAAAAGGC CAGGAACCGT AAAAAGGCCG CGTTGCTGGC GTTTTTCCAT AGGCTCCGCC
        TCGTTTTCCG GTCCTTGGCA TTTTTCCGGC GCAACGACCG CAAAAAGGTA TCCGAGGCGG 2581    CCCCTGACGA GCATCACAAA AATCGACGCT CAAGTCAGAG GTGGCGAAAC CCGACAGGAC
        GGGGACTGCT CGTAGTGTTT TTAGCTGCGA GTTCAGTCTC CACCGCTTTG GGCTGTCCTG 2641    TATAAAGATA CCAGGCGTTT CCCCCTGGAA GCTCCCTCGT GCGCTCTCCT GTTCCGACCC
        ATATTTCTAT GGTCCGCAAA GGGGGACCTT CGAGGGAGCA CGCGAGAGGA CAAGGCTGGG 2701    TGCCGCTTAC CGGATACCTG TCCGCCTTTC TCCCTTCGGG AAGCGTGGCG CTTTCTCAAT
        ACGGCGAATG GCCTATGGAC AGGCGGAAAG AGGGAAGCCC TTCGCACCGC GAAAGAGTTA 2761    GCTCACGCTG TAGGTATCTC AGTTCGGTGT AGGTCGTTCG CTCCAAGCTG GGCTGTGTGC
        CGAGTGCGAC ATCCATAGAG TCAAGCCACA TCCAGCAAGC GAGGTTCGAC CCGACACACG 2821    ACGAACCCCC CGTTCAGCCC GACCGCTGCG CCTTATCCGG TAACTATCGT CTTGAGTCCA
        TGCTTGGGGG GCAAGTCGGG CTGGCGACGC GGAATAGGCC ATTGATAGCA GAACTCAGGT 2881    ACCCGGTAAG ACACGACTTA TCGCCACTGG CAGCAGCCAC TGGTAACAGG ATTAGCAGAG
        TGGGCCATTC TGTGCTGAAT AGCGGTGACC GTCGTCGGTG ACCATTGTCC TAATCGTCTC 2941    CGAGGTATGT AGGCGGTGCT ACAGAGTTCT TGAAGTGGTG GCCTAACTAC GGCTACACTA
        GCTCCATACA TCCGCCACGA TGTCTCAAGA ACTTCACCAC CGGATTGATG CCGATGTGAT
```

FIG. 13D

```
3001  GAAGAACAGT ATTTGGTATC TGCGCTCTGC TGAAGCCAGT TACCTTCGGA AAAAGAGTTG
      CTTCTTGTCA TAAACCATAG ACGCGAGACG ACTTCGGTCA ATGGAAGCCT TTTTCTCAAC

3061  GTAGCTCTTG ATCCGGCAAA CAAACCACCG CTGGTAGCGG TGGTTTTTTT GTTTGCAAGC
      CATCGAGAAC TAGGCCGTTT GTTTGGTGGC GACCATCGCC ACCAAAAAAA CAAACGTTCG

3121  AGCAGATTAC GCGCAGAAAA AAAGGATCTC AAGAAGATCC TTTGATCTTT TCTACGGGGT
      TCGTCTAATG CGCGTCTTTT TTTCCTAGAG TTCTTCTAGG AAACTAGAAA AGATGCCCCA
                                                                   PacI
                                                                  ~~~~~~~~
3181  CTGACGCTCA GTGGAACGAA AACTCACGTT AAGGGATTTT GGTCATGGCT AGTTAATTAA
      GACTGCGAGT CACCTTGCTT TTGAGTGCAA TTCCCTAAAA CCAGTACCGA TCAATTAATT
      (SpAn→)
3241  GCTGCAATAA ACAATCATTA TTTTCATTGG ATCTGTGTGT TGGTTTTTTG TGTGGGCTTG
      CGACGTTATT TGTTAGTAAT AAAAGTAACC TAGACACACA ACCAAAAAAC ACACCCGAAC

3301  GGGGAGGGGG AGGCCAGAAT GACTCCAAGA GCTACAGGAA GGCAGGTCAG AGACCCCACT
      CCCCTCCCCC TCCGGTCTTA CTGAGGTTCT CGATGTCCTT CCGTCCAGTC TCTGGGGTGA

3361  GGACAAACAG TGGCTGGACT CTGCACCATA ACACACAATC AACAGGGGAG TGAGCTGGAT
      CCTGTTTGTC ACCGACCTGA GACGTGGTAT TGTGTGTTAG TTGTCCCCTC ACTCGACCTA
      (h CMV-1Aprom→)
3421  CGAGCTAGAG TCCGTTACAT AACTTACGGT AAATGGCCCG CCTGGCTGAC CGCCCAACGA
      GCTCGATCTC AGGCAATGTA TTGAATGCCA TTTACCGGGC GGACCGACTG GCGGGTTGCT 3481  CCCCCGCCCA TTGACGTCAA TAATGACGTA TGTTCCCATA GTAACGCCAA TAGGGACTTT
      GGGGGCGGGT AACTGCAGTT ATTACTGCAT ACAAGGGTAT CATTGCGGTT ATCCCTGAAA 3541  CCATTGACGT CAATGGGTGG AGTATTTACG GTAAACTGCC CACTTGGCAG TACATCAAGT
      GGTAACTGCA GTTACCCACC TCATAAATGC CATTTGACGG GTGAACCGTC ATGTAGTTCA 3601  GTATCATATG CCAAGTACGC CCCCTATTGA CGTCAATGAC GGTAAATGGC CCGCCTGGCA
      CATAGTATAC GGTTCATGCG GGGGATAACT GCAGTTACTG CCATTTACCG GGCGGACCGT 3661  TTATGCCCAG TACATGACCT TATGGGACTT TCCTACTTGG CAGTACATCT ACGTATTAGT
      AATACGGGTC ATGTACTGGA ATACCCTGAA AGGATGAACC GTCATGTAGA TGCATAATCA 3721  CATCGCTATT ACCATGGTGA TGCGGTTTTG GCAGTACATC AATGGGCGTG GATAGCGGTT
      GTAGCGATAA TGGTACCACT ACGCCAAAAC CGTCATGTAG TTACCCGCAC CTATCGCCAA 3781  TGACTCACGG GGATTTCCAA GTCTCCACCC CATTGACGTC AATGGGAGTT TGTTTTGGCA
      ACTGAGTGCC CCTAAAGGTT CAGAGGTGGG GTAACTGCAG TTACCCTCAA ACAAAACCGT
```

FIG. 13E

```
3841    CCAAAATCAA CGGGACTTTC CAAAATGTCG TAACAACTCC GCCCCATTGA CGCAAATGGG
        GGTTTTAGTT GCCCTGAAAG GTTTTACAGC ATTGTTGAGG CGGGGTAACT GCGTTTACCC

3901    CGGTAGGCGT GTACGGTGGG AGGTCTATAT AAGCAGAGCT CGTTTAGTGA ACCGTCAGAT
        GCCATCCGCA CATGCCACCC TCCAGATATA TTCGTCTCGA GCAAATCACT TGGCAGTCTA

3961    CGCCTGGAGA CGCCATCCAC GCTGTTTTGA CCTCCATAGA AGACACCGGG ACCGATCCAG
        GCGGACCTCT GCGGTAGGTG CGACAAAACT GGAGGTATCT TCTGTGGCCC TGGCTAGGTC

4021    CCTCCGCGGC CGGGAACGGT GCATTGGAAC GCGGATTCCC CGTGCCAAGA GTGACGTAAG
        GGAGGCGCCG GCCCTTGCCA CGTAACCTTG CGCCTAAGGG GCACGGTTCT CACTGCATTC

4081    TACCGCCTAT AGAGTCTATA GGCCCACCTA GTTGTGACCG GCGCCTAGTG TTGACAATTA
        ATGGCGGATA TCTCAGATAT CCGGGTGGAT CAACACTGGC CGCGGATCAC AACTGTTAAT

4141    ATCATCGGCA TAGTATAATA CGACTCACTA TAGGAGGGCC ACCATGTCGA CTACTAACCT
        TAGTAGCCGT ATCATATTAT GCTGAGTGAT ATCCTCCCGG TGGTACAGCT GATGATTGGA (HyTK→)
                                                      M  K  K  P  E  L ·
4201    TCTTCTCTTT CCTACAGCTG AGATCACCGG TAGGAGGGCC ATCATGAAAA AGCCTGAACT
        AGAAGAGAAA GGATGTCGAC TCTAGTGGCC ATCCTCCCGG TAGTACTTTT TCGGACTTGA

· T  A  T  S  V  A  K  F  L  I  E  K  F  D  S  V  S  D  L  M ·
4261    CACCGCGACG TCTGTCGCGA AGTTTCTGAT CGAAAAGTTC GACAGCGTCT CCGACCTGAT
        GTGGCGCTGC AGACAGCGCT TCAAAGACTA GCTTTTCAAG CTGTCGCAGA GGCTGGACTA

· Q  L  S  E  G  E  E  S  R  A  F  S  F  D  V  G  G  R  G  Y ·
4321    GCAGCTCTCG GAGGGCGAAG AATCTCGTGC TTTCAGCTTC GATGTAGGAG GGCGTGGATA
        CGTCGAGAGC CTCCCGCTTC TTAGAGCACG AAAGTCGAAG CTACATCCTC CCGCACCTAT

· V  L  R  V  N  S  C  A  D  G  F  Y  K  D  R  Y  V  Y  R  H ·
4381    TGTCCTGCGG GTAAATAGCT GCGCCGATGG TTTCTACAAA GATCGTTATG TTTATCGGCA
        ACAGGACGCC CATTTATCGA CGCGGCTACC AAAGATGTTT CTAGCAATAC AAATAGCCGT

· F  A  S  A  A  L  P  I  P  E  V  L  D  I  G  E  F  S  E  S ·
4441    CTTTGCATCG GCCGCGCTCC CGATTCCGGA AGTGCTTGAC ATTGGGGAAT TCAGCGAGAG
        GAAACGTAGC CGGCGCGAGG GCTAAGGCCT TCACGAACTG TAACCCCTTA AGTCGCTCTC

· L  T  Y  C  I  S  R  R  A  Q  G  V  T  L  Q  D  L  P  E  T ·
4501    CCTGACCTAT TGCATCTCCC GCCGTGCACA GGGTGTCACG TTGCAAGACC TGCCTGAAAC
        GGACTGGATA ACGTAGAGGG CGGCACGTGT CCCACAGTGC AACGTTCTGG ACGGACTTTG

· E  L  P  A  V  L  Q  P  V  A  E  L  M  D  A  I  A  A  A  D ·
4561    CGAACTGCCC GCTGTTCTGC AACCCGTCGC GGAGCTCATG GATGCGATCG CTGCGGCCGA
        GCTTGACGGG CGACAAGACG TTGGGCAGCG CCTCGAGTAC CTACGCTAGC GACGCCGGCT
```

FIG. 13F

```
           · L   S   Q     T   S   G   F     G P   F     G   P   Q     G   I   G   Q     Y T   T ·
    4621   TCTTAGCCAG ACGAGCGGGT TCGGCCCATT CGGACCGCAA GGAATCGGTC AATACACTAC
           AGAATCGGTC TGCTCGCCCA AGCCGGGTAA GCCTGGCGTT CCTTAGCCAG TTATGTGATG

· W   R   D     F   I   C   A     I   A   D     P   H   V     Y   H   W   Q     T   V   M ·
    4681   ATGGCGTGAT TTCATATGCG CGATTGCTGA TCCCCATGTG TATCACTGGC AAACTGTGAT
           TACCGCACTA AAGTATACGC GCTAACGACT AGGGGTACAC ATAGTGACCG TTTGACACTA

· D   D   T     V   S   A   S     V   A   Q     A   L   D     E   L   M   L     W   A   E ·
    4741   GGACGACACC GTCAGTGCGT CCGTCGCGCA GGCTCTCGAT GAGCTGATGC TTTGGGCCGA
           CCTGCTGTGG CAGTCACGCA GGCAGCGCGT CCGAGAGCTA CTCGACTACG AAACCCGGCT

· D   C   P     E   V   R   H     L   V   H     A   D   F     G   S   N   N     V   L   T ·
    4801   GGACTGCCCC GAAGTCCGGC ACCTCGTGCA CGCGGATTTC GGCTCCAACA ATGTCCTGAC
           CCTGACGGGG CTTCAGGCCG TGGAGCACGT GCGCCTAAAG CCGAGGTTGT TACAGGACTG

· D   N   G     R   I   T   A     V   I   D     W   S   E     A   M   F   G     D   S   Q ·
    4861   GGACAATGGC CGCATAACAG CGGTCATTGA CTGGAGCGAG GCGATGTTCG GGGATTCCCA
           CCTGTTACCG GCGTATTGTC GCCAGTAACT GACCTCGCTC CGCTACAAGC CCCTAAGGGT

· Y   E   V     A   N   I   F     F   W   R     P   W   L     A   C   M   E     Q   Q   T ·
    4921   ATACGAGGTC GCCAACATCT TCTTCTGGAG GCCGTGGTTG GCTTGTATGG AGCAGCAGAC
           TATGCTCCAG CGGTTGTAGA AGAAGACCTC CGGCACCAAC CGAACATACC TCGTCGTCTG

· R   Y   F     E   R   R   H     P   E   L     A   G   S     P   R   L   R     A   Y   M ·
    4981   GCGCTACTTC GAGCGGAGGC ATCCGGAGCT TGCAGGATCG CCGCGGCTCC GGGCGTATAT
           CGCGATGAAG CTCGCCTCCG TAGGCCTCGA ACGTCCTAGC GGCGCCGAGG CCCGCATATA

· L   R   I     G   L   D   Q     L   Y   Q     S   L   V     D   G   N   F     D   D   A ·
    5041   GCTCCGCATT GGTCTTGACC AACTCTATCA GAGCTTGGTT GACGGCAATT TCGATGATGC
           CGAGGCGTAA CCAGAACTGG TTGAGATAGT CTCGAACCAA CTGCCGTTAA AGCTACTACG

· A   W   A     Q   G   R   C     D   A   I     V   R   S     G   A   G   T     V   G   R ·
    5101   AGCTTGGGCG CAGGGTCGAT GCGACGCAAT CGTCCGATCC GGAGCCGGGA CTGTCGGGCG
           TCGAACCCGC GTCCCAGCTA CGCTGCGTTA GCAGGCTAGG CCTCGGCCCT GACAGCCCGC

· T   Q   I     A   R   R   S     A   A   V     W   T   D     G   C   V   E     V   A   S ·
    5161   TACACAAATC GCCCGCAGAA GCGCGGCCGT CTGGACCGAT GGCTGTGTAG AAGTCGCGTC
           ATGTGTTTAG CGGGCGTCTT CGCGCCGGCA GACCTGGCTA CCGACACATC TTCAGCGCAG

· A   F   D     Q   A   A   R     S   R   G     H   S   N     R   R   T   A     L   R   P ·
    5221   TGCGTTCGAC CAGGCTGCGC GTTCTCGCGG CCATAGCAAC CGACGTACGG CGTTGCGCCC
           ACGCAAGCTG GTCCGACGCG CAAGAGCGCC GGTATCGTTG GCTGCATGCC GCAACGCGGG

· R   R   Q     Q   E   A   T     E   V   R     P   E   Q     K   M   P   T     L   L   R ·
    5281   TCGCCGGCAG CAAGAAGCCA CGGAAGTCCG CCCGGAGCAG AAAATGCCCA CGCTACTGCG
           AGCGGCCGTC GTTCTTCGGT GCCTTCAGGC GGGCCTCGTC TTTTACGGGT GCGATGACGC
```

FIG. 13G

```
              · V   Y   I   D   G   P   H   G   M   G   K   T   T   T   T   Q   L   L   V   A ·
      5341    GGTTTATATA GACGGTCCCC ACGGGATGGG GAAAACCACC ACCACGCAAC TGCTGGTGGC
              CCAAATATAT CTGCCAGGGG TGCCCTACCC CTTTTGGTGG TGGTGCGTTG ACGACCACCG

· L   G   S   R   D   D   I   V   Y   V   P   E   P   M   T   Y   W   R   V   L ·
      5401    CCTGGGTTCG CGCGACGATA TCGTCTACGT ACCCGAGCCG ATGACTTACT GGCGGGTGCT
              GGACCCAAGC GCGCTGCTAT AGCAGATGCA TGGGCTCGGC TACTGAATGA CCGCCCACGA

· G   A   S   E   T   I   A   N   I   Y   T   T   Q   H   R   L   D   Q   G   E ·
      5461    GGGGGCTTCC GAGACAATCG CGAACATCTA CACCACACAA CACCGCCTCG ACCAGGGTGA
              CCCCCGAAGG CTCTGTTAGC GCTTGTAGAT GTGGTGTGTT GTGGCGGAGC TGGTCCCACT

· I   S   A   G   D   A   A   V   V   M   T   S   A   Q   I   T   M   G   M   P ·
      5521    GATATCGGCC GGGGACGCGG CGGTGGTAAT GACAAGCGCC CAGATAACAA TGGGCATGCC
              CTATAGCCGG CCCCTGCGCC GCCACCATTA CTGTTCGCGG GTCTATTGTT ACCCGTACGG

· Y   A   V   T   D   A   V   L   A   P   H   I   G   G   E   A   G   S   S   H ·
      5581    TTATGCCGTG ACCGACGCCG TTCTGGCTCC TCATATCGGG GGGGAGGCTG GGAGCTCACA
              AATACGGCAC TGGCTGCGGC AAGACCGAGG AGTATAGCCC CCCCTCCGAC CCTCGAGTGT

· A   P   P   P   A   L   T   L   I   F   D   R   H   P   I   A   A   L   L   C ·
      5641    TGCCCCGCCC CCGGCCCTCA CCCTCATCTT CGACCGCCAT CCCATCGCCG CCCTCCTGTG
              ACGGGGCGGG GGCCGGGAGT GGGAGTAGAA GCTGGCGGTA GGGTAGCGGC GGGAGGACAC

· Y   P   A   A   R   Y   L   M   G   S   M   T   P   Q   A   V   L   A   F   V ·
      5701    CTACCCGGCC GCGCGGTACC TTATGGGCAG CATGACCCCC CAGGCCGTGC TGGCGTTCGT
              GATGGGCCGG CGCGCCATGG AATACCCGTC GTACTGGGGG GTCCGGCACG ACCGCAAGCA

· A   L   I   P   P   T   L   P   G   T   N   I   V   L   G   A   L   P   E   D ·
      5761    GGCCCTCATC CCGCCGACCT TGCCCGGCAC CAACATCGTG CTTGGGGCCC TTCCGGAGGA
              CCGGGAGTAG GGCGGCTGGA ACGGGCCGTG GTTGTAGCAC GAACCCCGGG AAGGCCTCCT

· R   H   I   D   R   L   A   K   R   Q   R   P   G   E   R   L   D   L   A   M ·
      5821    CAGACACATC GACCGCCTGG CCAAACGCCA GCGCCCCGGC GAGCGGCTGG ACCTGGCTAT
              GTCTGTGTAG CTGGCGGACC GGTTTGCGGT CGCGGGGCCG CTCGCCGACC TGGACCGATA

· L   A   A   I   R   R   V   Y   G   L   L   A   N   T   V   R   Y   L   Q   C ·
      5881    GCTGGCTGCG ATTCGCCGCG TTTACGGGCT ACTTGCCAAT ACGGTGCGGT ATCTGCAGTG
              CGACCGACGC TAAGCGGCGC AAATGCCCGA TGAACGGTTA TGCCACGCCA TAGACGTCAC

· G   G   S   W   R   E   D   W   G   Q   L   S   G   T   A   V   P   P   Q   G ·
      5941    CGGCGGGTCG TGGCGGGAGG ACTGGGGACA GCTTTCGGGG ACGGCCGTGC CGCCCCAGGG
              GCCGCCCAGC ACCGCCCTCC TGACCCCTGT CGAAAGCCCC TGCCGGCACG GCGGGGTCCC

· A   E   P   Q   S   N   A   G   P   R   P   H   I   G   D   T   L   F   T   L ·
      6001    TGCCGAGCCC CAGAGCAACG CGGGCCCACG ACCCCATATC GGGGACACGT TATTTACCCT
              ACGGCTCGGG GTCTCGTTGC GCCCGGGTGC TGGGGTATAG CCCCTGTGCA ATAAATGGGA
```

FIG. 13H

```
              · F   R   A   P   E   L   L   A   P   N   G   D   L   Y   N   V   F   A   W   A ·
      6061    GTTTCGGGCC CCCGAGTTGC TGGCCCCCAA CGGCGACCTG TATAACGTGT TTGCCTGGGC
              CAAAGCCCGG GGGCTCAACG ACCGGGGGTT GCCGCTGGAC ATATTGCACA AACGGACCCG

· L   D   V   L   A   K   R   L   R   S   M   H   V   F   I   L   D   Y   D   Q ·
      6121    CTTGGACGTC TTTGGCCAAAC GCCTCCGTTC CATGCACGTC TTTATCCTGG ATTACGACCA
              GAACCTGCAG AAACCGGTTTG CGGAGGCAAG GTACGTGCAG AAATAGGACC TAATGCTGGT

· S   P   A   G   C   R   D   A   L   L   Q   L   T   S   G   M   V   Q   T   H ·
      6181    ATCGCCCGCC GGCTGCCGGG ACGCCCTGCT GCAACTTACC TCCGGGATGG TCCAGACCCA
              TAGCGGGCGG CCGACGGCCC TGCGGGACGA CGTTGAATGG AGGCCCTACC AGGTCTGGGT

· V   T   T   P   G   S   I   P   T   I   C   D   L   A   R   T   F   A   R   E ·
      6241    CGTCACCACC CCCGGCTCCA TACCGACGAT ATGCGACCTG GCGCGCACGT TTGCCCGGGA
              GCAGTGGTGG GGGCCGAGGT ATGGCTGCTA TACGCTGGAC CGCGCGTGCA AACGGGCCCT

· M   G   E   A   N   *  (BGh pAn→)
      6301    GATGGGGGAG GCTAACTGAG TCGAGAATTC GCTAGAGGGC CCTATTCTAT AGTGTCACCT
              CTACCCCCTC CGATTGACTC AGCTCTTAAG CGATCTCCCG GGATAAGATA TCACAGTGGA

6361    AAATGCTAGA GCTCGCTGAT CAGCCTCGAC TGTGCCTTCT AGTTGCCAGC CATCTGTTGT
              TTTACGATCT CGAGCGACTA GTCGGAGCTG ACACGGAAGA TCAACGGTCG GTAGACAACA

6421    TTGCCCCTCC CCCGTGCCTT CCTTGACCCT GGAAGGTGCC ACTCCCACTG TCCTTTCCTA
              AACGGGGAGG GGGCACGGAA GGAACTGGGA CCTTCCACGG TGAGGGTGAC AGGAAAGGAT

6481    ATAAAATGAG GAAATTGCAT CGCATTGTCT GAGTAGGTGT CATTCTATTC TGGGGGGTGG
              TATTTTACTC CTTTAACGTA GCGTAACAGA CTCATCCACA GTAAGATAAG ACCCCCCACC

6541    GGTGGGGCAG GACAGCAAGG GGGAGGATTG GGAAGACAAT AGCAGGCATG CGCAGGGCCC
              CCACCCCGTC CTGTCGTTCC CCCTCCTAAC CCTTCTGTTA TCGTCCGTAC GCGTCCCGGG

6601    AATTGCTCGA GCGGCCGCAA TAAAATATCT TTATTTTCAT TACATCTGTG TGTTGGTTTT
              TTAACGAGCT CGCCGGCGTT ATTTTATAGA AATAAAAGTA ATGTAGACAC ACAACCAAAA

6661    TTGTGTGAAT CGTAACTAAC ATACGCTCTC CATCAAAACA AAACGAAACA AAACAAACTA
              AACACACTTA GCATTGATTG TATGCGAGAG GTAGTTTTGT TTTGCTTTGT TTTGTTTGAT

6721    GCAAAATAGG CTGTCCCCAG TGCAAGTGCA GGTGCCAGAA CATTTCTCTA   (SEQ ID NO:19)
              CGTTTTATCC GACAGGGGTC ACGTTCACGT CCACGGTCTT GTAAAGAGAT   (SEQ ID NO:20)
```

HyTK amino acid sequence, SEQ ID NO:21
IL13zetakine amino acid sequence, SEQ ID NO:22

FIG. 13I

```
   1 caccctagag ccgccaccat gcttctcctg gtgacaagcc ttctgctctg tgagttacca
  61 cacccagcat tcctcctgat cccaggccct gtgcctccct ctacagccct caggtacctc
 121 attgaggagc tggtcaacat cacccagaac cagaaggctc cgctctgcaa tggcagcatg
 181 gtatggagca tcaacctgac agctggcatg tactgtgcag ccctggaatc cctgatcaac
 241 gtgtcaggct gcagtgccat cgagaagacc cagaggatgc tgagcggatt ctgcccgcac
 301 aaggtctcag ctgggcagtt ttccagcttg catgtccgag acaccaaaat cgaggtggcc
 361 cagtttgtaa aggacctgct cttacattta aagaaacttt ttcgcgaggg acggttcaac
 421 gagtccaaat atggtccccc atgcccacca tgcccagcac ctgagttcct ggggggacca
 481 tcagtcttcc tgttcccccc aaaacccaag gacactctca tgatctcccg gacccctgag
 541 gtcacgtgcg tggtggtgga cgtgagccag gaagacccca aggtccagtt caactggtac
 601 gtggatggcg tggaggtgca taatgccaag acaaagccgc gggaggagca gttcaacagc
 661 acgtaccgtg tggtcagcgt cctcaccgtc ctgcaccagg actggctgaa cggcaaggag
 721 tacaagtgca aggtctccaa caaaggcctc ccgtcctcca tcgagaaaac catctccaaa
 781 gccaaagggc agccccgaga gccacaggtg tacaccctgc ccccatccca ggaggagatg
 841 accaagaacc aggtcagcct gacctgcctg gtcaaaggct tctaccccag cgacatcgcc
 901 gtggagtggg agagcaatgg gcagccggag aacaactaca agaccacgcc tcccgtgctg
 961 gactccgacg gctccttctt cctctacagc aggctaaccg tggacaagag caggtggcag
1021 gaggggaatg tcttctcatg ctccgtgatg catgaggctc tgcacaacca ctacacacag
1081 aagagcctct ccctgtccct aggtaaaatg gccctgattg tgctgggggg cgtcgccggc
1141 ctcctgcttt tcattgggct aggcatcttc ttcagagtga agttcagcag gagcgcagac
1201 gcccccgcgt accagcaggg ccagaaccag ctctataacg agctcaatct aggacgaaga
1261 gaggagtacg atgttttgga caagagacgt ggccgggacc ctgagatggg gggaaagccg
1321 agaaggaaga accctcagga aggcctgtac aatgaactgc agaaagataa gatggcggag
1381 gcctacagtg agattgggat gaaaggcgag cgccggaggg gcaaggggca cgatggcctt
1441 taccagggtc tcagtacagc caccaaggac acctacgacg cccttcacat gcaggccctg
1501 cccccctcgc tgagcggccg cgaaggaggc ctagatctat cgattgtaca gctagctcga
1561 catgataaga tacattgatg agtttggaca aaccacaact agaatgcagt gaaaaaaatg
1621 ctttatttgt gaaatttgtg atgctattgc tttatttgtg aaatttgtga tgctattgct
1681 ttatttgtaa ccattataag ctgcaataaa caagttaaca acaacaattg cattcatttt
1741 atgtttcagg ttcagggggga ggtgtgggag gttttttaaa gcaagtaaaa cctctacaaa
1801 tgtggtagat ccatttaaat gttagcgaag aacatgtgag caaaaggcca gcaaaaggcc
1861 aggaaccgta aaaaggccgc gttgctggcg ttttttccata ggctccgccc cctgacgag
1921 catcacaaaa atcgacgctc aagtcagagg tggcgaaacc cgacaggact ataaagatac
1981 caggcgtttc ccctggaagc tccctcgtg cgctctcctg ttccgaccct gccgcttacc
2041 ggatacctgt ccgcctttct cccttcggga agcgtggcgc tttctcaatg ctcacgctgt
2101 aggtatctca gttcggtgta ggtcgttcgc tccaagctgg gctgtgtgca cgaaccccc
2161 gttcagcccg accgctgcgc cttatccggt aactatcgtc ttgagtccaa cccggtaaga
2221 cacgacttat cgccactggc agcagccact ggtaacagga ttagcagagc gaggtatgta
2281 ggcggtgcta cagagttctt gaagtggtgg cctaactacg gctacactag aagaacagta
2341 tttggtatct gcgctctgct gaagccagtt accttcggaa aaagagttgg tagctcttga
2401 tccggcaaac aaaccaccgc tggtagcggt ggttttttg tttgcaagca gcagattacg
```

FIG. 14A

```
2461 cgcagaaaaa aaggatctca agaagatcct ttgatctttt ctacggggtc tgacgctcag
2521 tggaacgaaa actcacgtta agggattttg gtcatggcta gttaattaag ctgcaataaa
2581 caatcattat tttcattgga tctgtgtgtt ggttttttgt gtgggcttgg gggaggggga
2641 ggccagaatg actccaagag ctacaggaag gcaggtcaga gaccccactg gacaaacagt
2701 ggctggactc tgcaccataa cacacaatca acaggggagt gagctggatc gagctagagt
2761 ccgttacata acttacggta aatggcccgc ctggctgacc gcccaacgac ccccgcccat
2821 tgacgtcaat aatgacgtat gttcccatag taacgccaat agggactttc cattgacgtc
2881 aatgggtgga gtatttacgg taaactgccc acttggcagt acatcaagtg tatcatatgc
2941 caagtacgcc ccctattgac gtcaatgacg gtaaatggcc cgcctggcat tatgcccagt
3001 acatgacctt atgggacttt cctacttggc agtacatcta cgtattagtc atcgctatta
3061 ccatggtgat gcggttttgg cagtacatca atgggcgtgg atagcggttt gactcacggg
3121 gatttccaag tctccacccc attgacgtca atgggagttt gttttggcac caaaatcaac
3181 gggactttcc aaaatgtcgt aacaactccg ccccattgac gcaaatgggc ggtaggcgtg
3241 tacggtggga ggtctatata agcagagctc gtttagtgaa ccgtcagatc gcctggagac
3301 gccatccacg ctgttttgac ctccatagaa gacaccggga ccgatccagc ctccgcggcc
3361 gggaacggtg cattggaacg cggattcccc gtgccaagag tgacgtaagt accgcctata
3421 gagtctatag gcccacctag ttgtgaccgg cgcctagtgt tgacaattaa tcatcggcat
3481 agtataatac gactcactat aggagggcca ccatgtcgac tactaacctt cttctctttc
3541 ctacagctga gatcaccggt aggagggcca tcatgaaaaa gcctgaactc accgcgacgt
3601 ctgtcgcgaa gtttctgatc gaaaagttcg acagcgtctc cgacctgatg cagctctcgg
3661 agggcgaaga atctcgtgct ttcagcttcg atgtaggagg gcgtggatat gtcctgcggg
3721 taaatagctg cgccgatggt ttctacaaag atcgttatgt ttatcggcac tttgcatcgg
3781 ccgcgctccc gattccggaa gtgcttgaca ttggggaatt cagcgagagc ctgacctatt
3841 gcatctcccg ccgtgcacag ggtgtcacgt tgcaagacct gcctgaaacc gaactgcccg
3901 ctgttctgca acccgtcgcg gagctcatgg atgcgatcgc tgcggccgat cttagccaga
3961 cgagcgggtt cggcccattc ggaccgcaag gaatcggtca atacactaca tggcgtgatt
4021 tcatatgcgc gattgctgat ccccatgtgt atcactggca aactgtgatg gacgacaccg
4081 tcagtgcgtc cgtcgcgcag gctctcgatg agctgatgct ttgggccgag gactgccccg
4141 aagtccggca cctcgtgcac gcggatttcg gctccaacaa tgtcctgacg gacaatggcc
4201 gcataacagc ggtcattgac tggagcgagg cgatgttcgg ggattcccaa tacgaggtcg
4261 ccaacatctt cttctggagg ccgtggttgg cttgtatgga gcagcagacg cgctacttcg
4321 agcggaggca tccggagctt gcaggatcgc cgcggctccg gcgtatatg ctccgcattg
4381 gtcttgacca actctatcag agcttggttg acggcaattt cgatgatgca gcttgggcgc
4441 agggtcgatg cgacgcaatc gtccgatccg gagccgggac tgtcgggcgt acacaaatcg
4501 cccgcagaag cgcggccgtc tggaccgatg ctgtgtaga agtcgcgtct gcgttcgacc
4561 aggctgcgcg ttctcgcggc catagcaacc gacgtacggc gttgcgccct cgccggcagc
4621 aagaagccac ggaagtccgc ccggagcaga aaatgcccac gctactgcgg gtttatatag
4681 acggtcccca cgggatgggg aaaaccacca ccacgcaact gctggtggcc ctgggttcgc
4741 gcgacgatat cgtctacgta cccgagccga tgacttactg gcgggtgctg ggggcttccg
4801 agacaatcgc gaacatctac accacacaac accgcctcga ccagggtgag atatcggccg
4861 gggacgcggc ggtggtaatg acaagcgccc agataacaat gggcatgcct tatgccgtga
4921 ccgacgccgt tctggctcct catatcgggg gggaggctgg gagctcacat gccccgcccc
```

FIG. 14B

```
4981 cggccctcac cctcatcttc gaccgccatc ccatcgccgc cctcctgtgc tacccggccg
5041 cgcggtacct tatgggcagc atgacccccc aggccgtgct ggcgttcgtg gccctcatcc
5101 cgccgacctt gcccggcacc aacatcgtgc ttggggcccct tccggaggac agacacatcg
5161 accgcctggc caaacgccag cgccccggcg agcggctgga cctggctatg ctggctgcga
5221 ttcgccgcgt ttacgggcta cttgccaata cggtgcggta tctgcagtgc ggcgggtcgt
5281 ggcgggagga ctggggacag ctttcgggga cggccgtgcc gccccagggt gccgagcccc
5341 agagcaacgc gggcccacga ccccatatcg gggacacgtt atttaccctg tttcgggccc
5401 ccgagttgct ggcccccaac ggcgacctgt ataacgtgtt tgcctgggcc ttggacgtct
5461 tggccaaacg cctccgttcc atgcacgtct ttatcctgga ttacgaccaa tcgcccgccg
5521 gctgccggga cgccctgctg caacttacct ccgggatggt ccagacccac gtcaccaccc
5581 ccggctccat accgacgata tgcgacctgg cgcgcacgtt tgcccgggag atgggggagg
5641 ctaactgagt cgagaattcg ctagagggcc ctattctata gtgtcaccta aatgctagag
5701 ctcgctgatc agcctcgact gtgccttcta gttgccagcc atctgttgtt tgcccctccc
5761 ccgtgccttc cttgaccctg gaaggtgcca ctcccactgt cctttcctaa taaaatgagg
5821 aaattgcatc gcattgtctg agtaggtgtc attctattct gggggggtggg gtggggcagg
5881 acagcaaggg ggaggattgg gaagacaata gcaggcatgc gcagggccca attgctcgag
5941 cggccgcaat aaaatatctt tattttcatt acatctgtgt gttggttttt tgtgtgaatc
6001 gtaactaaca tacgctctcc atcaaaacaa aacgaaacaa aacaaactag caaaataggc
6061 tgtccccagt gcaagtgcag gtgccagaac atttctctat cgaaggatct gcgatcgctc
6121 cggtgcccgt cagtgggcag agcgcacatc gcccacagtc cccgagaagt tggggggagg
6181 ggtcggcaat tgaaccggtg cctagagaag gtggcgcggg gtaaactggg aaagtgatgt
6241 cgtgtactgg ctccgccttt ttccccgaggg tggggagaa ccgtatataa gtgcagtagt
6301 cgccgtgaac gttctttttc gcaacgggtt tgccgccaga acacagctga agcttcgagg
6361 ggctcgcatc tctccttcac gcgcccgccg cctacctga ggccgccatc cacgccggtt
6421 gagtcgcgtt ctgccgcctc ccgcctgtgg tgcctcctga actgcgtccg ccgtctaggt
6481 aagtttaaag ctcaggtcga gaccgggcct tgtccggcg ctcccttgga gcctacctag
6541 actcagccgg ctctccacgc tttgcctgac cctgcttgct caactctacg tctttgtttc
6601 gttttctgtt ctgcgccgtt acagatccaa gctgtgaccg gcgcctacgt aagtgatatc
6661 tactagattt atcaaaaaga gtgttgactt gtgagcgctc acaattgata cggattcatc
6721 gagagggaca cgtcgactac taaccttctt ctctttccta cagctgagat (SEQ ID NO:23)
```

FIG. 14C

Plasmid DNA Vector Sequence (hEF1p→)
```
  1  TCGAAGGATC TGCGATCGCT CCGGTGCCCG TCAGTGGGCA GAGCGCACAT CGCCCACAGT
     AGCTTCCTAG ACGCTAGCGA GGCCACGGGC AGTCACCCGT CTCGCGTGTA GCGGGTGTCA 61  CCCCGAGAAG TTGGGGGGAG GGGTCGGCAA TTGAACCGGT GCCTAGAGAA GGTGGCGCGG
     GGGGCTCTTC AACCCCCCTC CCCAGCCGTT AACTTGGCCA CGGATCTCTT CCACCGCGCC 121  GGTAAACTGG GAAAGTGATG TCGTGTACTG GCTCCGCCTT TTTCCCGAGG GTGGGGGAGA
     CCATTTGACC CTTTCACTAC AGCACATGAC CGAGGCGGAA AAAGGGCTCC CACCCCCTCT 181  ACCGTATATA AGTGCAGTAG TCGCCGTGAA CGTTCTTTTT CGCAACGGGT TTGCCGCCAG
     TGGCATATAT TCACGTCATC AGCGGCACTT GCAAGAAAAA GCGTTGCCCA AACGGCGGTC 241  AACACAGCTG AAGCTTCGAG GGCTCGCAT CTCTCCTTCA CGCGCCCGCC GCCCTACCTG
     TTGTGTCGAC TTCGAAGCTC CCCGAGCGTA GAGAGGAAGT GCGCGGGCGG CGGGATGGAC 301  AGGCCGCCAT CCACGCCGGT TGAGTCGCGT TCTGCCGCCT CCCGCCTGTG GTGCCTCCTG
     TCCGGCGGTA GGTGCGGCCA ACTCAGCGCA AGACGGCGGA GGGCGGACAC CACGGAGGAC 361  AACTGCGTCC GCCGTCTAGG TAAGTTTAAA GCTCAGGTCG AGACCGGGCC TTTGTCCGGC
     TTGACGCAGG CGGCAGATCC ATTCAAATTT CGAGTCCAGC TCTGGCCCGG AAACAGGCCG 421  GCTCCCTTGG AGCCTACCTA GACTCAGCCG GCTCTCCACG CTTTGCCTGA CCCTGCTTGC
     CGAGGGAACC TCGGATGGAT CTGAGTCGGC CGAGAGGTGC GAAACGGACT GGGACGAACG 481  TCAACTCTAC GTCTTTGTTT CGTTTTCTGT TCTGCGCCGT TACAGATCCA AGCTGTGACC
     AGTTGAGATG CAGAAACAAA GCAAAAGACA AGACGCGGCA ATGTCTAGGT TCGACACTGG 541  GGCGCCTACG TAAGTGATAT CTACTAGATT TATCAAAAAG AGTGTTGACT TGTGAGCGCT
     CCGCGGATGC ATTCACTATA GATGATCTAA ATAGTTTTTC TCACAACTGA ACACTCGCGA 601  CACAATTGAT ACGGATTCAT CGAGAGGGAC ACGTCGACTA CTAACCTTCT TCTCTTTCCT
     GTGTTAACTA TGCCTAAGTA GCTCTCCCTG TGCAGCTGAT GATTGGAAGA AGAGAAAGGA
                                                    (IL13zetakine→)
                                     M   L   L   V   T   S   L   L   L·
661  ACAGCTGAGA TCACCCTAGA GCCGCCACCA TGCTTCTCCT GGTGACAAGC CTTCTGCTCT
     TGTCGACTCT AGTGGGATCT CGGCGGTGGT ACGAAGAGGA CCACTGTTCG GAAGACGAGA C   E   L   P   H   P   A   F   L   L   I   P   G   P   V   P   P   S   T   A·
721  GTGAGTTACC ACACCCAGCA TTCCTCCTGA TCCCAGGCCC TGTGCCTCCC TCTACAGCCC
     CACTCAATGG TGTGGGTCGT AAGGAGGACT AGGGTCCGGG ACACGGAGGG AGATGTCGGG L   R   Y   L   I   E   E   L   V   N   I   T   Q   N   Q   K   A   P   L   C·
781  TCAGGTACCT CATTGAGGAG CTGGTCAACA TCACCCAGAA CCAGAAGGCT CCGCTCTGCA
     AGTCCATGGA GTAACTCCTC GACCAGTTGT AGTGGGTCTT GGTCTTCCGA GGCGAGACGT
```

FIG. 15A

```
       N  G  S  M     V  W  S     I  N  L  T     A  G  M     Y  C  A     A  L  E·
 841   ATGGCAGCAT GGTATGGAGC ATCAACCTGA CAGCTGGCAT GTACTGTGCA GCCCTGGAAT
       TACCGTCGTA CCATACCTCG TAGTTGGACT GTCGACCGTA CATGACACGT CGGGACCTTA

S  L  I  N     V  S  G     C  S  A  I     E  K  T     Q  R  M     L  S  G·
 901   CCCTGATCAA CGTGTCAGGC TGCAGTGCCA TCGAGAAGAC CCAGAGGATG CTGAGCGGAT
       GGGACTAGTT GCACAGTCCG ACGTCACGGT AGCTCTTCTG GGTCTCCTAC GACTCGCCTA

F  C  P  H     K  V  S     A  Q  F     S  S  L     H  V  R     D  T  K·
 961   TCTGCCCCA CAAGGTCTCA GCTGGGCAGT TTTCCAGCTT GCATGTCCGA GACACCAAAA
       AGACGGGCGT GTTCCAGAGT CGACCCGTCA AAAGGTCGAA CGTACAGGCT CTGTGGTTTT

I  E  V  A     Q  F  V     K  D  L  L     L  H  L     K  K  L     F  R  E·
1021   TCGAGGTGGC CCAGTTTGTA AAGGACCTGC TCTTACATTT AAAGAAACTT TTTCGCGAGG
       AGCTCCACCG GGTCAAACAT TTCCTGGACG AGAATGTAAA TTTCTTTGAA AAAGCGCTCC

G  R  F  N     E  S  K     Y  G  P  P     C  P  P     C  P  A     P  E  F·
1081   GACGGTTCAA CGAGTCCAAA TATGGTCCCC CATGCCCACC ATGCCCAGCA CCTGAGTTCC
       CTGCCAAGTT GCTCAGGTTT ATACCAGGGG GTACGGGTGG TACGGGTCGT GGACTCAAGG

L  G  G  P     S  V  F     L  P  P  P     K  P  K     D  T  L     M  I  S·
1141   TGGGGGGACC ATCAGTCTTC CTGTTCCCCC CAAAACCCAA GGACACTCTC ATGATCTCCC
       ACCCCCCTGG TAGTCAGAAG GACAAGGGGG GTTTTGGGTT CCTGTGAGAG TACTAGAGGG

R  T  P  E     V  T  C     V  V  V  D     V  S  Q     E  D  P     E  V  Q·
1201   GGACCCCTGA GGTCACGTGC GTGGTGGTGG ACGTGAGCCA GGAAGACCCC GAGGTCCAGT
       CCTGGGGACT CCAGTGCACG CACCACCACC TGCACTCGGT CCTTCTGGGG CTCCAGGTCA

F  N  W  Y     V  D  G     V  E  V  H     N  A  K     T  K  P     R  E  E·
1261   TCAACTGGTA CGTGGATGGC GTGGAGGTGC ATAATGCCAA GACAAAGCCG CGGGAGGAGC
       AGTTGACCAT GCACCTACCG CACCTCCACG TATTACGGTT CTGTTTCGGC GCCCTCCTCG

Q  F  N  S     T  Y  R     V  V  S  V     L  T  V     L  H  Q     D  W  L·
1321   AGTTCAACAG CACGTACCGT GTGGTCAGCG TCCTCACCGT CCTGCACCAG GACTGGCTGA
       TCAAGTTGTC GTGCATGGCA CACCAGTCGC AGGAGTGGCA GGACGTGGTC CTGACCGACT

N  G  K  E     Y  K  C     K  V  S  N     K  G  L     P  S  S     I  E  K·
1381   ACGGCAAGGA GTACAAGTGC AAGGTCTCCA ACAAAGGCCT CCCGTCCTCC ATCGAGAAAA
       TGCCGTTCCT CATGTTCACG TTCCAGAGGT TGTTTCCGGA GGGCAGGAGG TAGCTCTTTT

T  I  S  K     A  K  G     Q  P  R  E     P  Q  V     Y  T  L     P  P  S·
1461   CCATCTCCAA AGCCAAAGGG CAGCCCCGAG AGCCACAGGT GTACACCCTG CCCCCATCCC
       GGTAGAGGTT TCGGTTTCCC GTCGGGGCTC TCGGTGTCCA CATGTGGGAC GGGGGTAGGG

Q  E  E  M     T  K  N     Q  V  S  L     T  C  L     V  K  G     F  Y  P·
1501   AGGAGGAGAT GACCAAGAAC CAGGTCAGCC TGACCTGCCT GGTCAAAGGC TTCTACCCCA
       TCCTCCTCTA CTGGTTCTTG GTCCAGTCGG ACTGGACGGA CCAGTTTCCG AAGATGGGGT

S  D  I  A     V  E  W     E  S  N  G     Q  P  E     N  N  Y     K  T  T·
1561   GCGACATCGC CGTGGAGTGG GAGAGCAATG GGCAGCCGGA GAACAACTAC AAGACCACGC
       CGCTGTAGCG GCACCTCACC CTCTCGTTAC CCGTCGGCCT CTTGTTGATG TTCTGGTGCG
```

FIG. 15B

```
          P   P   V   L   D   S   D   G   S   F   F   L   Y   S   R   L   T       V   D   K·
1621   CTCCCGTGCT GGACTCCGAC GGCTCCTTCT TCCTCTACAG CAGGCTAACC GTGGACAAGA
       GAGGGCACGA CCTGAGGCTG CCGAGGAAGA AGGAGATGTC GTCCGATTGG CACCTGTTCT

S   R   W   Q   E   G   N   V   F   S   C   S   V   M   H   E   A       L   H   N·
1681   GCAGGTGGCA GGAGGGGAAT GTCTTCTCAT GCTCCGTGAT GCATGAGGCT CTGCACAACC
       CGTCCACCGT CCTCCCCTTA CAGAAGAGTA CGAGGCACTA CGTACTCCGA GACGTGTTGG

H   Y   T   Q   K   S   L   S   L   S   L   G   K   M   A   L   I       V   L   G·
1741   ACTACACACA GAAGAGCCTC TCCCTGTCCC TAGGTAAAAT GGCCCTGATT GTGCTGGGGG
       TGATGTGTGT CTTCTCGGAG AGGGACAGGG ATCCATTTTA CCGGGACTAA CACGACCCCC

G   V   A   G   L   L   L   F   I   G   L   G   I   F   F   R   V       K   F   S·
1801   GCGTCGCCGG CCTCCTGCTT TTCATTGGGC TAGGCATCTT CTTCAGAGTG AAGTTCAGCA
       CGCAGCGGCC GGAGGACGAA AAGTAACCCG ATCCGTAGAA GAAGTCTCAC TTCAAGTCGT

R   S   A   D   A   P   A   Y   Q   Q   G   Q   N   Q   L   Y   N       E   L   N·
1861   GGAGCGCAGA CGCCCCCGCG TACCAGCAGG GCCAGAACCA GCTCTATAAC GAGCTCAATC
       CCTCGCGTCT GCGGGGGCGC ATGGTCGTCC CGGTCTTGGT CGAGATATTG CTCGAGTTAG

L   G   R   R   E   E   Y   D   V   L   D   K   R   R   G   R   D       P   E   M·
1921   TAGGACGAAG AGAGGAGTAC GATGTTTTGG ACAAGAGACG TGGCCGGGAC CCTGAGATGG
       ATCCTGCTTC TCTCCTCATG CTACAAAACC TGTTCTCTGC ACCGGCCCTG GGACTCTACC

G   G   K   P   R   R   K   N   P   Q   E   G   L   Y   N   E   L       Q   K   D·
1981   GGGGAAAGCC GAGAAGGAAG AACCCTCAGG AAGGCCTGTA CAATGAACTG CAGAAAGATA
       CCCCTTTCGG CTCTTCCTTC TTGGGAGTCC TTCCGGACAT GTTACTTGAC GTCTTTCTAT

K   M   A   E   A   Y   S   E   I   G   M   K   G   E   R   R   R       G   K   G·
2041   AGATGGCGGA GGCCTACAGT GAGATTGGGA TGAAAGGCGA GCGCCGGAGG GGCAAGGGGC
       TCTACCGCCT CCGGATGTCA CTCTAACCCT ACTTTCCGCT CGCGGCCTCC CCGTTCCCCG

H   D   G   L   Y   Q   G   L   S   T   A   T   K   D   T   Y   D       A   L   H·
2101   ACGATGGCCT TTACCAGGGT CTCAGTACAG CCACCAAGGA CACCTACGAC GCCCTTCACA
       TGCTACCGGA AATGGTCCCA GAGTCATGTC GGTGGTTCCT GTGGATGCTG CGGGAAGTGT

M   Q   A   L   P   P   R   *
2161   TGCAGGCCCT GCCCCCTCGC TGAGCGGCCG GCGAAGGAGG CCTAGATCTA TCGATTGTAC
       ACGTCCGGGA CGGGGGAGCG ACTCGCCGGC CGCTTCCTCC GGATCTAGAT AGCTAACATG
               (late SV40pAN→)
2221   AGCTAGCTCG ACATGATAAG ATACATTGAT GAGTTTGGAC AAACCACAAC TAGAATGCAG
       TCGATCGAGC TGTACTATTC TATGTAACTA CTCAAACCTG TTTGGTGTTG ATCTTACGTC 2281   TGAAAAAAAT GCTTTATTTG TGAAATTTGT GATGCTATTG CTTTATTTGT GAAATTTGTG
       ACTTTTTTTA CGAAATAAAC ACTTTAAACA CTACGATAAC GAAATAAACA CTTTAAACAC 2341   ATGCTATTGC TTTATTTGTA ACCATTATAA GCTGCAATAA ACAAGTTAAC AACAACAATT
       TACGATAACG AAATAAACAT TGGTAATATT CGACGTTATT TGTTCAATTG TTGTTGTTAA
```

FIG. 15C

```
2401  GCATTCATTT TATGTTTCAG GTTCAGGGGG AGGTGTGGGA GGTTTTTTAA AGCAAGTAAA
      CGTAAGTAAA ATACAAAGTC CAAGTCCCCC TCCACACCCT CCAAAAAATT TCGTTCATTT
                                                    (ori ColE1→)
2461  ACCTCTACAA ATGTGGTAGA TCCATTTAAA TGTTAGCGAA GAACATGTGA GCAAAAGGCC
      TGGAGATGTT TACACCATCT AGGTAAATTT ACAATCGCTT CTTGTACACT CGTTTTCCGG 2521  AGCAAAAGGC CAGGAACCGT AAAAAGGCCG CGTTGCTGGC GTTTTTCCAT AGGCTCCGCC
      TCGTTTTCCG GTCCTTGGCA TTTTTCCGGC GCAACGACCG CAAAAAGGTA TCCGAGGCGG 2581  CCCCTGACGA GCATCACAAA AATCGACGCT CAAGTCAGAG GTGGCGAAAC CCGACAGGAC
      GGGGACTGCT CGTAGTGTTT TTAGCTGCGA GTTCAGTCTC CACCGCTTTG GGCTGTCCTG 2641  TATAAAGATA CCAGGCGTTT CCCCCTGGAA GCTCCCTCGT GCGCTCTCCT GTTCCGACCC
      ATATTTCTAT GGTCCGCAAA GGGGGACCTT CGAGGGAGCA CGCGAGAGGA CAAGGCTGGG 2701  TGCCGCTTAC CGGATACCTG TCCGCCTTTC TCCCTTCGGG AAGCGTGGCG CTTTCTCAAT
      ACGGCGAATG GCCTATGGAC AGGCGGAAAG AGGGAAGCCC TTCGCACCGC GAAAGAGTTA 2761  GCTCACGCTG TAGGTATCTC AGTTCGGTGT AGGTCGTTCG CTCCAAGCTG GGCTGTGTGC
      CGAGTGCGAC ATCCATAGAG TCAAGCCACA TCCAGCAAGC GAGGTTCGAC CCGACACACG 2821  ACGAACCCCC CGTTCAGCCC GACCGCTGCG CCTTATCCGG TAACTATCGT CTTGAGTCCA
      TGCTTGGGGG GCAAGTCGGG CTGGCGACGC GGAATAGGCC ATTGATAGCA GAACTCAGGT 2881  ACCCGGTAAG ACACGACTTA TCGCCACTGG CAGCAGCCAC TGGTAACAGG ATTAGCAGAG
      TGGGCCATTC TGTGCTGAAT AGCGGTGACC GTCGTCGGTG ACCATTGTCC TAATCGTCTC 2941  CGAGGTATGT AGGCGGTGCT ACAGAGTTCT TGAAGTGGTG GCCTAACTAC GGCTACACTA
      GCTCCATACA TCCGCCACGA TGTCTCAAGA ACTTCACCAC CGGATTGATG CCGATGTGAT 3001  GAAGAACAGT ATTTGGTATC TGCGCTCTGC TGAAGCCAGT TACCTTCGGA AAAAGAGTTG
      CTTCTTGTCA TAAACCATAG ACGCGAGACG ACTTCGGTCA ATGGAAGCCT TTTTCTCAAC 3061  GTAGCTCTTG ATCCGGCAAA CAAACCACCG CTGGTAGCGG TGGTTTTTTT GTTTGCAAGC
      CATCGAGAAC TAGGCCGTTT GTTTGGTGGC GACCATCGCC ACCAAAAAAA CAAACGTTCG 3121  AGCAGATTAC GCGCAGAAAA AAGGATCTC AAGAAGATCC TTTGATCTTT TCTACGGGGT
      TCGTCTAATG CGCGTCTTTT TTTCCTAGAG TTCTTCTAGG AAACTAGAAA AGATGCCCCA
                                                         PacI
3181  CTGACGCTCA GTGGAACGAA AACTCACGTT AAGGGATTTT GGTCATGGCT AGTTAATTAA
      GACTGCGAGT CACCTTGCTT TTGAGTGCAA TTCCCTAAAA CCAGTACCGA TCAATTAATT
      (SpAn)
3241  GCTGCAATAA ACAATCATTA TTTTCATTGG ATCTGTGTGT TGGTTTTTTG TGTGGGCTTG
      CGACGTTATT TGTTAGTAAT AAAAGTAACC TAGACACACA ACCAAAAAAC ACACCCGAAC 3301  GGGGAGGGGG AGGCCAGAAT GACTCCAAGA GCTACAGGAA GGCAGGTCAG AGACCCCACT
      CCCCTCCCCC TCCGGTCTTA CTGAGGTTCT CGATGTCCTT CCGTCCAGTC TCTGGGGTGA
```

FIG. 15D

```
3361  GGACAAACAG TGGCTGGACT CTGCACCATA ACACACAATC AACAGGGGAG TGAGCTGGAT
      CCTGTTTGTC ACCGACCTGA GACGTGGTAT TGTGTGTTAG TTGTCCCCTC ACTCGACCTA
                    (h CMV-1Aprom→)
3421  CGAGCTAGAG TCCGTTACAT AACTTACGGT AAATGGCCCG CCTGGCTGAC CGCCCAACGA
      GCTCGATCTC AGGCAATGTA TTGAATGCCA TTTACCGGGC GGACCGACTG GCGGGTTGCT 3481  CCCCCGCCCA TTGACGTCAA TAATGACGTA TGTTCCCATA GTAACGCCAA TAGGGACTTT
      GGGGGCGGGT AACTGCAGTT ATTACTGCAT ACAAGGGTAT CATTGCGGTT ATCCCTGAAA 3561  CCATTGACGT CAATGGGTGG AGTATTTACG GTAAACTGCC CACTTGGCAG TACATCAAGT
      GGTAACTGCA GTTACCCACC TCATAAATGC CATTTGACGG GTGAACCGTC ATGTAGTTCA 3601  GTATCATATG CCAAGTACGC CCCCTATTGA CGTCAATGAC GGTAAATGGC CCGCCTGGCA
      CATAGTATAC GGTTCATGCG GGGATAACT GCAGTTACTG CCATTTACCG GGCGGACCGT 3661  TTATGCCCAG TACATGACCT TATGGGACTT TCCTACTTGG CAGTACATCT ACGTATTAGT
      AATACGGGTC ATGTACTGGA ATACCCTGAA AGGATGAACC GTCATGTAGA TGCATAATCA 3721  CATCGCTATT ACCATGGTGA TGCGGTTTTG GCAGTACATC AATGGGCGTG GATAGCGGTT
      GTAGCGATAA TGGTACCACT ACGCCAAAAC CGTCATGTAG TTACCCGCAC CTATCGCCAA 3781  TGACTCACGG GGATTTCCAA GTCTCCACCC CATTGACGTC AATGGGAGTT TGTTTTGGCA
      ACTGAGTGCC CCTAAAGGTT CAGAGGTGGG GTAACTGCAG TTACCCTCAA ACAAAACCGT 3841  CCAAAATCAA CGGGACTTTC CAAAATGTCG TAACAACTCC GCCCCATTGA CGCAAATGGG
      GGTTTTAGTT GCCCTGAAAG GTTTTACAGC ATTGTTGAGG CGGGGTAACT GCGTTTACCC 3901  CGGTAGGCGT GTACGGTGGG AGGTCTATAT AAGCAGAGCT CGTTTAGTGA ACCGTCAGAT
      GCCATCCGCA CATGCCACCC TCCAGATATA TTCGTCTCGA GCAAATCACT TGGCAGTCTA 3961  CGCCTGGAGA CGCCATCCAC GCTGTTTTGA CCTCCATAGA AGACACCGGG ACCGATCCAG
      GCGGACCTCT GCGGTAGGTG CGACAAAACT GGAGGTATCT TCTGTGGCCC TGGCTAGGTC 4021  CCTCCGCGGC CGGGAACGGT GCATTGGAAC GCGGATTCCC CGTGCCAAGA GTGACGTAAG
      GGAGGCGCCG GCCCTTGCCA CGTAACCTTG CGCCTAAGGG CACGGTTCT CACTGCATTC 4081  TACCGCCTAT AGAGTCTATA GGCCCACCTA GTTGTGACCG GCGCCTAGTG TTGACAATTA
      ATGGCGGATA TCTCAGATAT CCGGGTGGAT CAACACTGGC CGCGGATCAC AACTGTTAAT 4141  ATCATCGGCA TAGTATATCG GCATAGTATA ATACGACTCA CTATAGGAGG GCCACCATGT
      TAGTAGCCGT ATCATATAGC CGTATCATAT TATGCTGAGT GATATCCTCC CGGTGGTACA
                                                              (HyTK→)
                                                              M  ·
4201  CGACTACTAA CCTTCTTCTC TTTCCTACAG CTGAGATCAC CGGTAGGAGG GCCATCATGA
      GCTGATGATT GGAAGAAGAG AAAGGATGTC GACTCTAGTG GCCATCCTCC CGGTAGTACT K  K  P  E  L  T  A  T  S  V  A  K  F  L  I  E  K  F  D  S  ·
4261  AAAAGCCTGA ACTCACCGCG ACGTCTGTCG CGAAGTTTCT GATCGAAAAG TTCGACAGCG
      TTTTCGGACT TGAGTGGCGC TGCAGACAGC GCTTCAAAGA CTAGCTTTTC AAGCTGTCGC
```

FIG. 15E

```
          V  S  D  L     M  Q  L     S  E  G  E     E  S  R     A  F  S     F  D  V  ·
4321   TCTCCGACCT GATGCAGCTC TCGGAGGGCG AAGAATCTCG TGCTTTCAGC TTCGATGTAG
       AGAGGCTGGA CTACGTCGAG AGCCTCCCGC TTCTTAGAGC ACGAAAGTCG AAGCTACATC

G  G  R  G     Y  V  L     R  V  N  S     C  A  D     G  F  Y     K  D  R  ·
4381   GAGGGCGTGG ATATGTCCTG CGGGTAAATA GCTGCGCCGA TGGTTTCTAC AAAGATCGTT
       CTCCCGCACC TATACAGGAC GCCCATTTAT CGACGCGGCT ACCAAAGATG TTTCTAGCAA

Y  V  Y  R     H  F  A     S  A  A  L     P  I  P     E  V  L     D  I  G  ·
4441   ATGTTTATCG GCACTTTGCA TCGGCCGCGC TCCCGATTCC GGAAGTGCTT GACATTGGGG
       TACAAATAGC CGTGAAACGT AGCCGGCGCG AGGGCTAAGG CCTTCACGAA CTGTAACCCC

E  F  S  E     S  L  T     Y  C  I  S     R  R  A     Q  G  V     T  L  Q  ·
4501   AATTCAGCGA GAGCCTGACC TATTGCATCT CCCGCCGTGC ACAGGGTGTC ACGTTGCAAG
       TTAAGTCGCT CTCGGACTGG ATAACGTAGA GGGCGGCACG TGTCCCACAG TGCAACGTTC

D  L  P  E     T  E  L     P  A  V  L     Q  P  V     A  E  L     M  D  A  ·
4561   ACCTGCCTGA AACCGAACTG CCCGCTGTTC TGCAACCCGT CGCGGAGCTC ATGGATGCGA
       TGGACGGACT TTGGCTTGAC GGGCGACAAG ACGTTGGGCA GCGCCTCGAG TACCTACGCT

I  A  A  A     D  L  S     Q  T  S  G     F  G  P     F  G  P     Q  G  I  ·
4621   TCGCTGCGGC CGATCTTAGC CAGACGAGCG GGTTCGGCCC ATTCGGACCG CAAGGAATCG
       AGCGACGCCG GCTAGAATCG GTCTGCTCGC CCAAGCCGGG TAAGCCTGGC GTTCCTTAGC

G  Q  Y  T     T  W  R     D  F  I  C     A  I  A     D  P  H     V  Y  H  ·
4681   GTCAATACAC TACATGGCGT GATTTCATAT GCGCGATTGC TGATCCCCAT GTGTATCACT
       CAGTTATGTG ATGTACCGCA CTAAAGTATA CGCGCTAACG ACTAGGGGTA CACATAGTGA

W  Q  T  V     M  D  D     T  V  S  A     S  V  A     Q  A  L     D  E  L  ·
4741   GGCAAACTGT GATGGACGAC ACCGTCAGTG CGTCCGTCGC GCAGGCTCTC GATGAGCTGA
       CCGTTTGACA CTACCTGCTG TGGCAGTCAC GCAGGCAGCG CGTCCGAGAG CTACTCGACT

M  L  W  A     E  D  C     P  E  V  R     H  L  V     H  A  D     F  G  S  ·
4801   TGCTTTGGGC CGAGGACTGC CCCGAAGTCC GGCACCTCGT GCACGCGGAT TTCGGCTCCA
       ACGAAACCCG GCTCCTGACG GGGCTTCAGG CCGTGGAGCA CGTGCGCCTA AAGCCGAGGT

N  N  V  L     T  D  N     G  R  I  T     A  V  I     D  W  S     E  A  M  ·
4861   ACAATGTCCT GACGGACAAT GGCCGCATAA CAGCGGTCAT TGACTGGAGC GAGGCGATGT
       TGTTACAGGA CTGCCTGTTA CCGGCGTATT GTCGCCAGTA ACTGACCTCG CTCCGCTACA

F  G  D  S     Q  Y  E     V  A  N  I     F  F  W     R  P  W     L  A  C  ·
4921   TCGGGGATTC CCAATACGAG GTCGCCAACA TCTTCTTCTG GAGGCCGTGG TTGGCTTGTA
       AGCCCCTAAG GGTTATGCTC CAGCGGTTGT AGAAGAAGAC CTCCGGCACC AACCGAACAT

M  E  Q  Q     T  R  Y     F  E  R  R     H  P  E     L  A  G     S  P  R  ·
4981   TGGAGCAGCA GACGCGCTAC TTCGAGCGGA GGCATCCGGA GCTTGCAGGA TCGCCGCGGC
       ACCTCGTCGT CTGCGCGATG AAGCTCGCCT CCGTAGGCCT CGAACGTCCT AGCGGCGCCG

L  R  A  Y     M  L  R     I  G  L  D     Q  L  Y     Q  S  L     V  D  G  ·
5041   TCCGGGCGTA TATGCTCCGC ATTGGTCTTG ACCAACTCTA TCAGAGCTTG GTTGACGGCA
       AGGCCCGCAT ATACGAGGCG TAACCAGAAC TGGTTGAGAT AGTCTCGAAC CAACTGCCGT
```

FIG. 15F

```
          N  F  D  D     A  A  W     A  Q  G  R     C  D  A     I  V  R     S  G  A ·
5101     ATTTCGATGA TGCAGCTTGG GCGCAGGGTC GATGCGACGC AATCGTCCGA TCCGGAGCCG
         TAAAGCTACT ACGTCGAACC CGCGTCCCAG CTACGCTGCG TTAGCAGGCT AGGCCTCGGC

G  T  V  G     R  T  Q     I  A  R  R     S  A  A     V  W  T     D  G  C ·
5161     GGACTGTCGG GCGTACACAA ATCGCCCGCA GAAGCGCGGC CGTCTGGACC GATGGCTGTG
         CCTGACAGCC CGCATGTGTT TAGCGGGCGT CTTCGCGCCG GCAGACCTGG CTACCGACAC

V  E  V  A     S  A  F     D  Q  A  A     R  S  R     G  H  S     N  R  R ·
5221     TAGAAGTCGC GTCTGCGTTC GACCAGGCTG CGCGTTCTCG CGGCCATAGC AACCGACGTA
         ATCTTCAGCG CAGACGCAAG CTGGTCCGAC GCGCAAGAGC GCCGGTATCG TTGGCTGCAT

T  A  L  R     P  R  R     Q  Q  E  A     T  E  V     R  P  E     Q  K  M ·
5281     CGGCGTTGCG CCCTCGCCGG CAGCAAGAAG CCACGGAAGT CCGCCCGGAG CAGAAAATGC
         GCCGCAACGC GGGAGCGGCC GTCGTTCTTC GGTGCCTTCA GGCGGGCCTC GTCTTTTACG

P  T  L  L     R  V  Y     I  D  G  P     H  G  M     G  K  T     T  T  T ·
5341     CCACGCTACT GCGGGTTTAT ATAGACGGTC CCCACGGGAT GGGGAAAACC ACCACCACGC
         GGTGCGATGA CGCCCAAATA TATCTGCCAG GGGTGCCCTA CCCCTTTTGG TGGTGGTGCG

Q  L  L  V     A  L  G     S  R  D  D     I  V  Y     V  P  E     P  M  T ·
5401     AACTGCTGGT GGCCCTGGGT TCGCGCGACG ATATCGTCTA CGTACCCGAG CCGATGACTT
         TTGACGACCA CCGGGACCCA AGCGCGCTGC TATAGCAGAT GCATGGGCTC GGCTACTGAA

Y  W  R  V     L  G  A     S  E  T  I     A  N  I     Y  T  T     Q  H  R ·
5461     ACTGGCGGGT GCTGGGGGCT TCCGAGACAA TCGCGAACAT CTACACCACA CAACACCGCC
         TGACCGCCCA CGACCCCCGA AGGCTCTGTT AGCGCTTGTA GATGTGGTGT GTTGTGGCGG

L  D  Q  G     E  I  S     A  G  D  A     V  V  M     T  S  A     Q  I ·
5521     TCGACCAGGG TGAGATATCG GCCGGGACG CGGCGGTGGT AATGACAAGC GCCCAGATAA
         AGCTGGTCCC ACTCTATAGC CGGCCCCTGC GCCGCCACCA TTACTGTTCG CGGGTCTATT

T  M  G  M     P  Y  A     V  T  D  A     V  L  A     P  H  I     G  G  E ·
5581     CAATGGGCAT GCCTTATGCC GTGACCGACG CCGTTCTGGC TCCTCATATC GGGGGGGAGG
         GTTACCCGTA CGGAATACGG CACTGGCTGC GGCAAGACCG AGGAGTATAG CCCCCCCTCC

A  G  D  S     H  A  P     P  P  A  L     T  L  I     F  D  R     H  P  I ·
5641     CTGGGAGCTC ACATGCCCCG CCCCCGGCCC TCACCCTCAT CTTCGACCGC CATCCCATCG
         GACCCTCGAG TGTACGGGGC GGGGGCCGGG AGTGGGAGTA GAAGCTGGCG GTAGGGTAGC

A  A  L  L     C  Y  P     A  A  R  Y     L  M  G     S  M  T     P  Q  A ·
5701     CCGCCCTCCT GTGCTACCCG GCCGCGCGGT ACCTTATGGG CAGCATGACC CCCCAGGCCG
         GGCGGGAGGA CACGATGGGC CGGCGCGCCA TGGAATACCC GTCGTACTGG GGGGTCCGGC

V  L  A  F     V  A  L     I  P  P  T     L  P  G     T  N  I     V  L  G ·
5761     TGCTGGCGTT CGTGGCCCTC ATCCCGCCGA CCTTGCCCGG CACCAACATC GTGCTTGGGG
         ACGACCGCAA GCACCGGGAG TAGGGCGGCT GGAACGGGCC GTGGTTGTAG CACGAACCCC

A  L  P  E     D  R  H     I  D  R  L     A  K  R     Q  R  P     G  E  R ·
5821     CCCTTCCGGA GGACAGACAC ATCGACCGCC TGGCCAAACG CCAGCGCCCC GGCGAGCGGC
         GGGAAGGCCT CCTGTCTGTG TAGCTGGCGG ACCGGTTTGC GGTCGCGGGG CCGCTCGCCG
```

FIG. 15G

```
              L   D   L   A     M   L   A     A   I   R   R     V   Y   G     L   L   A     N   T   V   ·
       TGGACCTGGC TATGCTGGCT GCGATTCGCC GCGTTTACGG GCTACTTGCC AATACGGTGC
5881   ACCTGGACCG ATACGACCGA CGCTAAGCGG CGCAAATGCC CGATGAACGG TTATGCCACG

R   Y   L   Q     C   G   G     S   W   R   E     D   W   G     Q   L   S     G   T   A   ·
       GGTATCTGCA GTGCGGCGGG TCGTGGCGGG AGGACTGGGG ACAGCTTTCG GGGACGGCCG
5941   CCATAGACGT CACGCCGCCC AGCACCGCCC TCCTGACCCC TGTCGAAAGC CCCTGCCGGC

V   P   P   Q     G   A   E     P   Q   S   N     A   G   P     R   P   H     I   G   D   ·
       TGCCGCCCCA GGGTGCCGAG CCCCAGAGCA ACGCGGGCCC ACGACCCCAT ATCGGGGACA
6001   ACGGCGGGGT CCCACGGCTC GGGGTCTCGT TGCGCCCGGG TGCTGGGGTA TAGCCCCTGT

T   L   F   T     L   F   R     A   P   E   L     L   A   P     N   G   D     L   Y   N   ·
       CGTTATTTAC CCTGTTTCGG GCCCCCGAGT TGCTGGCCCC CAACGGCGAC CTGTATAACG
6061   GCAATAAATG GGACAAAGCC CGGGGGCTCA ACGACCGGGG GTTGCCGCTG GACATATTGC

V   F   A   W     A   L   D     V   L   A   K     R   L   R     S   M   H     V   F   I   ·
       TGTTTGCCTG GGCCTTGGAC GTCTTGGCCA AACGCCTCCG TTCCATGCAC GTCTTTATCC
6121   ACAAACGGAC CCGGAACCTG CAGAACCGGT TTGCGGAGGC AAGGTACGTG CAGAAATAGG

L   D   Y   D     Q   S   P     A   G   C   R     D   A   L     L   Q   L     T   S   G   ·
       TGGATTACGA CCAATCGCCC GCCGGCTGCC GGGACGCCCT GCTGCAACTT ACCTCCGGGA
6181   ACCTAATGCT GGTTAGCGGG CGGCCGACGG CCCTGCGGGA CGACGTTGAA TGGAGGCCCT

M   V   Q   T     H   V   T     T   P   G   S     I   P   T     I   C   D     L   A   R   ·
       TGGTCCAGAC CCACGTCACC ACCCCCGGCT CCATACCGAC GATATGCGAC CTGGCGCGCA
6241   ACCAGGTCTG GGTGCAGTGG TGGGGGCCGA GGTATGGCTG CTATACGCTG GACCGCGCGT

T   F   A   R     E   M   G     E   A   N   *  (bGh Pa→)
       CGTTTGCCCG GGAGATGGGG GAGGCTAACT GAGTCGAGAA TTCGCTAGAG GGCCCTATTC
6301   GCAAACGGGC CCTCTACCCC CTCCGATTGA CTCAGCTCTT AAGCGATCTC CCGGGATAAG

TATAGTGTCA CCTAAATGCT AGAGCTCGCT GATCAGCCTC GACTGTGCCT TCTAGTTGCC
6361   ATATCACAGT GGATTTACGA TCTCGAGCGA CTAGTCGGAG CTGACACGGA AGATCAACGG

AGCCATCTGT TGTTTGCCCC TCCCCCGTGC CTTCCTTGAC CCTGGAAGGT GCCACTCCCA
6421   TCGGTAGACA ACAAACGGGG AGGGGGCACG GAAGGAACTG GGACCTTCCA CGGTGAGGGT

CTGTCCTTTC CTAATAAAAT GAGGAAATTG CATCGCATTG TCTGAGTAGG TGTCATTCTA
6481   GACAGGAAAG GATTATTTTA CTCCTTTAAC GTAGCGTAAC AGACTCATCC ACAGTAAGAT

TTCTGGGGGG TGGGGTGGGG CAGGACAGCA AGGGGGAGGA TTGGGAAGAC AATAGCAGGC
6541   AAGACCCCCC ACCCCACCCC GTCCTGTCGT TCCCCCTCCT AACCCTTCTG TTATCGTCCG

ATGCGCAGGG CCCAATTGCT CGAGCGGCCG CAATAAAATA TCTTTATTTT CATTACATCT
6601   TACGCGTCCC GGGTTAACGA GCTCGCCGGC GTTATTTTAT AGAAATAAAA GTAATGTAGA

GTGTGTTGGT TTTTTGTGTG AATCGTAACT AACATACGCT CTCCATCAAA ACAAAACGAA
6661   CACACAACCA AAAAACACAC TTAGCATTGA TTGTATGCGA GAGGTAGTTT TGTTTTGCTT

ACAAAACAAA CTAGCAAAAT AGGCTGTCCC CAGTGCAAGT GCAGGTGCCA GAACATTTCT
6721   TGTTTTGTTT GATCGTTTTA TCCGACAGGG GTCACGTTCA CGTCCACGGT CTTGTAAAGA

CTA (SEQ ID NO:14)
6781   GAT (SEQ ID NO:16)
```

FIG. 15H

SEQUENCE LISTING

```
<160> NUMBER OF SEQ ID NOS: 25

<210> SEQ ID NO 1
<211> LENGTH: 102
<212> TYPE: DNA
<213> ORGANISM: Homo sapiens
<220> FEATURE:
<221> NAME/KEY: misc_feature
<222> LOCATION: (4)..(9)
<223> OTHER INFORMATION: EcoRI restriction site

<400> SEQUENCE: 1
tatgaattca tggcgctttt gttgaccacg gtcattgctc tcacttgcct tggcggcttt      60 gcctcccag gccctgtgcc tccctctaca gccctcaggt ac                        102

<210> SEQ ID NO 2
<211> LENGTH: 101
<212> TYPE: DNA
<213> ORGANISM: Homo sapiens

<400> SEQUENCE: 2
gttgatgctc cataccatgc tgccattgca gagcggagcc ttctggttct gggtgatgtt      60
```

```
gaccagctcc tcaatgaggt acctgagggc tgtagaggga g                    101
```

<210> SEQ ID NO 3
<211> LENGTH: 100
<212> TYPE: DNA
<213> ORGANISM: Homo sapiens

<400> SEQUENCE: 3

```
ctctgggtct tctcgatggc actgcagcct gacacgttga tcagggattc cagggctgca    60
cagtacatgc cagctgtcag gttgatgctc cataccatgc                          100
```

<210> SEQ ID NO 4
<211> LENGTH: 100
<212> TYPE: DNA
<213> ORGANISM: Homo sapiens

<400> SEQUENCE: 4

```
cctcgatttt ggtgtctcgg acatgcaagc tggaaaactg cccagctgag accttgtgcg    60
ggcagaatcc gctcagcatc ctctgggtct tctcgatggc                          100
```

<210> SEQ ID NO 5
<211> LENGTH: 96
<212> TYPE: DNA
<213> ORGANISM: Homo sapiens
<220> FEATURE:
<221> NAME/KEY: misc_feature
<222> LOCATION: (3)..(8)
<223> OTHER INFORMATION: BamHI restriction site

<400> SEQUENCE: 5

```
tcggatcctc agttgaaccg tccctcgcga aaagtttct ttaaatgtaa gagcaggtcc     60
tttacaaact gggccacctc gattttggtg tctcgg                              96
```

<210> SEQ ID NO 6
<211> LENGTH: 39
<212> TYPE: DNA
<213> ORGANISM: Homo sapiens

<400> SEQUENCE: 6

```
caacctgaca gctggcatgt actgtgcagc cctggaatc                           39
```

<210> SEQ ID NO 7
<211> LENGTH: 39
<212> TYPE: DNA
<213> ORGANISM: Homo sapiens

<400> SEQUENCE: 7

```
gattccaggg ctgcacagta catgccagct gtcaggttg                           39
```

<210> SEQ ID NO 8
<211> LENGTH: 43
<212> TYPE: DNA
<213> ORGANISM: Homo sapiens
<220> FEATURE:
<221> NAME/KEY: misc_feature
<222> LOCATION: (4)..(9)
<223> OTHER INFORMATION: XbaI restriction site

<400> SEQUENCE: 8

```
atctctagag ccgccaccat gcttctcctg gtgacaagcc ttc                      43
```

<210> SEQ ID NO 9
<211> LENGTH: 34
<212> TYPE: DNA

<213> ORGANISM: Homo sapiens

<400> SEQUENCE: 9
gagggaggca cagggcctgg gatcaggagg aatg                              34

<210> SEQ ID NO 10
<211> LENGTH: 34
<212> TYPE: DNA
<213> ORGANISM: Homo sapiens

<400> SEQUENCE: 10
cattcctcct gatcccaggc cctgtgcctc cctc                              34

<210> SEQ ID NO 11
<211> LENGTH: 35
<212> TYPE: DNA
<213> ORGANISM: Homo sapiens

<400> SEQUENCE: 11
gggaccatat ttggactcgt tgaaccgtcc ctcgc                             35

<210> SEQ ID NO 12
<211> LENGTH: 35
<212> TYPE: DNA
<213> ORGANISM: Homo sapiens

<400> SEQUENCE: 12
gcgagggacg gttcaacgag tccaaatatg gtccc                             35

<210> SEQ ID NO 13
<211> LENGTH: 26
<212> TYPE: DNA
<213> ORGANISM: Homo sapiens
<220> FEATURE:
<221> NAME/KEY: misc_feature
<222> LOCATION: (3)..(10)
<223> OTHER INFORMATION: NotI restriction site

<400> SEQUENCE: 13
atgcggccgc tcagcgaggg ggcagg                                       26

<210> SEQ ID NO 14
<211> LENGTH: 6783
<212> TYPE: DNA
<213> ORGANISM: Artificial Sequence
<220> FEATURE:
<223> OTHER INFORMATION: plasmid DNA vector incorporating human, simian
      virus 40, E. coli, cytomegalovirus and bovine sequences

<400> SEQUENCE: 14
tcgaaggatc tgcgatcgct ccggtgcccg tcagtgggca gagcgcacat cgcccacagt    60
ccccgagaag ttgggggggag gggtcggcaa ttgaaccggt gcctagagaa ggtggcgcgg   120
ggtaaactgg gaaagtgatg tcgtgtactg gctccgcctt tttcccgagg gtgggggaga   180
accgtatata agtgcagtag tcgccgtgaa cgttctttt cgcaacgggt ttgccgccag    240
aacacagctg aagcttcgag gggctcgcat ctctccttca cgcgcccgcc gccctacctg    300
aggccgccat ccacgccggt tgagtcgcgt tctgccgcct cccgcctgtg gtgcctcctg   360
aactgcgtcc gccgtctagg taagtttaaa gctcaggtcg agaccgggcc tttgtccggc    420
gctcccttgg agcctaccta gactcagccg gctctccacg ctttgcctga cctgcttgc    480 tcaactctac gtctttgttt cgttttctgt tctgcgccgt tacagatcca agctgtgacc   540
ggcgcctacg taagtgatat ctactagatt tatcaaaaag agtgttgact tgtgagcgct   600

```
cacaattgat acggattcat cgagagggac acgtcgacta ctaaccttct tctctttcct    660
acagctgaga tcaccctaga gccgccacca tgcttctcct ggtgacaagc cttctgctct    720
gtgagttacc acacccagca ttcctcctga tcccaggccc tgtgcctccc tctacagccc    780
tcaggtacct cattgaggag ctggtcaaca tcacccagaa ccagaaggct ccgctctgca    840
atggcagcat ggtatggagc atcaacctga cagctggcat gtactgtgca gccctggaat    900
ccctgatcaa cgtgtcaggc tgcagtgcca tcgagaagac ccagaggatg ctgagcggat    960
tctgcccgca caaggtctca gctgggcagt tttccagctt gcatgtccga gacaccaaaa   1020
tcgaggtggc ccagtttgta aaggacctgc tcttacattt aaagaaactt tttcgcgagg   1080
gacggttcaa cgagtccaaa tatggtcccc catgcccacc atgccagca cctgagttcc    1140
tgggggggacc atcagtcttc ctgttccccc caaaacccaa ggacactctc atgatctccc   1200
ggaccctga ggtcacgtgc gtggtggtgg acgtgagcca ggaagacccc gaggtccagt    1260
tcaactggta cgtggatggc gtggaggtgc ataatgccaa gacaaagccg cgggaggagc   1320
agttcaacag cacgtaccgt gtggtcagcg tcctcaccgt cctgcaccag gactggctga   1380
acggcaagga gtacaagtgc aaggtctcca acaaaggccc ccgtcctcc atcgagaaaa    1440
ccatctccaa agccaaaggg cagccccgag agccacaggt gtacaccctg cccccatccc   1500
aggaggagat gaccaagaac caggtcagcc tgacctgcct ggtcaaaggc ttctacccca   1560
gcgacatcgc cgtggagtgg gagagcaatg ggcagccgga gaacaactac aagaccacgc   1620
ctcccgtgct ggactccgac ggctccttct tcctctacag caggctaacc gtggacaaga   1680
gcaggtggca ggaggggaat gtcttctcat gctccgtgat gcatgaggct ctgcacaacc   1740
actacacaca gaagagcctc tccctgtccc taggtaaaat ggccctgatt gtgctggggg   1800
gcgtcgccgg cctcctgctt ttcattgggc taggcatctt cttcagagtg aagttcagca   1860
ggagcgcaga cgcccccgcg taccagcagg gccagaacca gctctataac gagctcaatc   1920
taggacgaag agaggagtac gatgttttgg acaagagacg tggccgggac cctgagatgg   1980
ggggaaagcc gagaaggaag aaccctcagg aaggcctgta caatgaactg cagaaagata   2040
agatggcgga ggcctacagt gagattggga tgaaaggcga gcgccggagg ggcaagggc    2100
acgatggcct ttaccagggt ctcagtacag ccaccaagga cacctacgac gcccttcaca   2160
tgcaggccct gccccctcgc tgagcggccg gcgaaggagg cctagatcta tcgattgtac   2220
agctagctcg acatgataag atacattgat gagtttggac aaaccacaac tagaatgcag   2280
tgaaaaaaat gctttatttg tgaaatttgt gatgctattg ctttatttgt gaaatttgtg   2340
atgctattgc tttatttgta accattataa gctgcaataa acaagttaac aacaacaatt   2400
gcattcattt tatgtttcag gttcagggg aggtgtggga ggttttttaa agcaagtaaa    2460
acctctacaa atgtggtaga tccatttaaa tgttagcgaa gaacatgtga gcaaaaggcc   2520
agcaaaaggc caggaaccgt aaaaaggccg cgttgctggc gttttccat aggctccgcc    2580
cccctgacga gcatcacaaa aatcgacgct caagtcagag gtggcgaaac ccgacaggac   2640
tataaagata ccaggcgttt ccccctggaa gctccctcgt gcgctctcct gttccgaccc   2700
tgccgcttac cggatacctg tccgcctttc tcccttcggg aagcgtggcg ctttctcaat   2760
gctcacgctg taggtatctc agttcggtgt aggtcgttcg ctccaagctg ggctgtgtgc   2820
acgaaccccc cgttcagccc gaccgctgcg ccttatccgg taactatcgt cttgagtcca   2880
acccggtaag acacgactta tcgccactgg cagcagccac tggtaacagg attagcagag   2940
cgaggtatgt aggcggtgct acagagttct tgaagtggtg gcctaactac ggctacacta   3000
```

```
gaagaacagt atttggtatc tgcgctctgc tgaagccagt taccttcgga aaaagagttg   3060
gtagctcttg atccggcaaa caaaccaccg ctggtagcgg tggttttttt gtttgcaagc   3120
agcagattac gcgcagaaaa aaaggatctc aagaagatcc tttgatcttt tctacgggt    3180 ctgacgctca gtggaacgaa aactcacgtt aagggatttt ggtcatggct agttaattaa   3240
gctgcaataa acaatcatta ttttcattgg atctgtgtgt tggttttttg tgtgggcttg   3300
ggggaggggg aggccagaat gactccaaga gctacaggaa ggcaggtcag agaccccact   3360
ggacaaacag tggctggact ctgcaccata acacacaatc aacaggggag tgagctggat   3420
cgagctagag tccgttacat aacttacggt aaatggcccg cctggctgac cgcccaacga   3480
cccccgccca ttgacgtcaa taatgacgta tgttcccata gtaacgccaa tagggacttt   3540
ccattgacgt caatgggtgg agtatttacg gtaaactgcc cacttggcag tacatcaagt   3600
gtatcatatg ccaagtacgc ccccattga  cgtcaatgac ggtaaatggc ccgcctggca   3660
ttatgcccag tacatgacct tatgggactt tcctacttgg cagtacatct acgtattagt   3720
catcgctatt accatggtga tgcggttttg gcagtacatc aatgggcgtg atagcggtt    3780 tgactcacgg ggatttccaa gtctccaccc cattgacgtc aatgggagtt tgttttggca   3840
ccaaaatcaa cgggactttc caaaatgtcg taacaactcc gccccattga cgcaaatggg   3900
cggtaggcgt gtacggtggg aggtctatat aagcagagct cgtttagtga accgtcagat   3960
cgcctggaga cgccatccac gctgttttga cctccataga agacaccggg accgatccag   4020
cctccgcggc cgggaacggt gcattggaac gcggattccc cgtgccaaga gtgacgtaag   4080
taccgcctat agagtctata ggcccaccta gttgtgaccg gcgcctagtg ttgacaatta   4140
atcatcggca tagtatatcg gcatagtata atacgactca ctataggagg gccaccatgt   4200
cgactactaa ccttcttctc tttcctacag ctgagatcac cggtaggagg gccatcatga   4260
aaaagcctga actcaccgcg acgtctgtcg cgaagtttct gatcgaaaag ttcgacagcg   4320
tctccgacct gatgcagctc tcggagggcg aagaatctcg tgctttcagc ttcgatgtag   4380
gagggcgtgg atatgtcctg cgggtaaata gctgcgccga tggtttctac aaagatcgtt   4440
atgtttatcg gcactttgca tcggccgcgc tcccgattcc ggaagtgctt gacattgggg   4500
aattcagcga gagcctgacc tattgcatct cccgccgtgc acagggtgtc acgttgcaag   4560
acctgcctga aaccgaactg cccgctgttc tgcaacccgt cgcggagctc atggatgcga   4620
tcgctgcggc cgatcttagc cagacgagcg ggttcggccc attcggaccg caaggaatcg   4680
gtcaatacac tacatggcgt gatttcatat gcgcgattgc tgatccccat gtgtatcact   4740
ggcaaactgt gatggacgac accgtcagtg cgtccgtcgc gcaggctctc gatgagctga   4800
tgctttgggc cgaggactgc cccgaagtcc ggcacctcgt gcacgcggat ttcggctcca   4860
acaatgtcct gacggacaat ggccgcataa cagcggtcat tgactggagc gaggcgatgt   4920
tcggggattc ccaatacgag gtcgccaaca tcttcttctg gaggccgtgg ttggcttgta   4980
tggagcagca gacgcgctac ttcgagcgga ggcatccgga gcttgcagga tcgccgcggc   5040
tccgggcgta tatgctccgc attggtcttg accaactcta tcagagcttg gttgacggca   5100
atttcgatga tgcagcttgg gcgcagggtc gatgcgacgc aatcgtccga tccggagccg   5160
ggactgtcgg gcgtacacaa atcgcccgca gaagcgcggc cgtctggacc gatggctgtg   5220
tagaagtcgc gtctgcgttc gaccaggctg cgcgttctcg cggccatagc aaccgacgta   5280
cggcgttgcg ccctcgccgg cagcaagaag ccacggaagt ccgcccggag cagaaaatgc   5340
ccacgctact gcgggtttat atagacggtc cccacgggat ggggaaaacc accaccacgc   5400
```

```
aactgctggt ggccctgggt tcgcgcgacg atatcgtcta cgtacccgag ccgatgactt    5460
actggcgggt gctgggggct tccgagacaa tcgcgaacat ctacaccaca caacaccgcc    5520
tcgaccaggg tgagatatcg gccggggacg cggcggtggt aatgacaagc gcccagataa    5580
caatgggcat gccttatgcc gtgaccgacg ccgttctggc tcctcatatc ggggggggagg   5640 ctgggagctc acatgcccg ccccggcc tcaccctcat cttcgaccgc catcccatcg       5700 ccgcccctcct gtgctacccg gccgcgcggt accttatggg cagcatgacc ccccaggccg   5760
tgctggcgtt cgtggccctc atccgccga ccttgcccgg caccaacatc gtgcttgggg     5820
cccttccgga ggacagacac atcgaccgcc tggccaaacg ccagcgcccc ggcgagcggc    5880
tggacctggc tatgctggct gcgattcgcc gcgtttacgg gctacttgcc aatacggtgc    5940
ggtatctgca gtgcggcggg tcgtggcggg aggactgggg acagctttcg gggacggccg    6000
tgccgcccca gggtgccgag ccccagagca acgcgggccc acgacccat atcggggaca     6060 cgttatttac cctgtttcgg gccccgagt tgctggcccc caacggcgac ctgtataacg     6120
tgtttgcctg ggccttggac gtcttggcca aacgcctccg ttccatgcac gtctttatcc    6180
tggattacga ccaatcgccc gccggctgcc gggacgccct gctgcaactt acctccggga   6240
tggtccagac ccacgtcacc accccggct ccataccgac gatatgcgac ctggcgcgca    6300
cgtttgcccg ggagatgggg gaggctaact gagtcgagaa ttcgctagag ggccctattc    6360
tatagtgtca cctaaatgct agagctcgct gatcagcctc gactgtgcct tctagttgcc    6420
agccatctgt tgtttgcccc tcccccgtgc cttccttgac cctggaaggt gccactccca    6480
ctgtcctttc ctaataaaat gaggaaattg catcgcattg tctgagtagg tgtcattcta    6540
ttctgggggg tggggtgggg caggacagca aggggggagga ttgggaagac aatagcaggc    6600
atgcgcaggg cccaattgct cgagcggccg caataaaata tctttatttt cattacatct    6660
gtgtgttggt tttttgtgtg aatcgtaact aacatacgct ctccatcaaa acaaaacgaa    6720
acaaaacaaa ctagcaaaat aggctgtccc cagtgcaagt gcaggtgcca gaacatttct    6780
cta                                                                  6783
```

<210> SEQ ID NO 15
<211> LENGTH: 1491
<212> TYPE: DNA
<213> ORGANISM: Homo sapiens

<400> SEQUENCE: 15

```
atgcttctcc tggtgacaag ccttctgctc tgtgagttac cacacccagc attcctcctg     60
atcccaggcc ctgtgcctcc ctctacagcc ctcaggtacc tcattgagga gctggtcaac   120
atcacccaga accagaaggc tccgctctgc aatggcagca tggtatggag catcaacctg   180
acagctggca tgtactgtgc agccctggaa tccctgatca acgtgtcagg ctgcagtgcc   240
atcgagaaga cccagaggat gctgagcgga ttctgcccgc acaaggtctc agctgggcag   300
ttttccagct tgcatgtccg agacaccaaa atcgaggtgg cccagtttgt aaaggacctg   360
ctcttacatt taaagaaact ttttcgcgag ggacggttca acgagtccaa atatggtccc   420
ccatgcccac catgcccagc acctgagttc ctggggggac catcagtctt cctgttcccc   480
ccaaaaccca aggacactct catgatctcc cggaccctg aggtcacgtg cgtggtggtg    540
gacgtgagcc aggaagaccc cgaggtccag ttcaactggt acgtggatgg cgtggaggtg    600
cataatgcca agacaaagcc gcgggaggag cagttcaaca gcacgtaccg tgtggtcagc   660
gtcctcaccg tcctgcacca ggactggctg aacggcaagg agtacaagtg caaggtctcc   720
```

```
aacaaaggcc tcccgtcctc catcgagaaa accatctcca aagccaaagg gcagccccga    780
gagccacagg tgtacaccct gcccccatcc caggaggaga tgaccaagaa ccaggtcagc    840
ctgacctgcc tggtcaaagg cttctacccc agcgacatcg ccgtggagtg ggagagcaat    900
gggcagccgg agaacaacta caagaccacg cctcccgtgc tggactccga cggctccttc    960
ttcctctaca gcaggctaac cgtggacaag agcaggtggc aggagggaa tgtcttctca    1020 tgctccgtga tgcatgaggc tctgcacaac cactacacac agaagagcct ctccctgtcc    1080
ctaggtaaaa tggccctgat gtgctgggg ggcgtcgccg gcctcctgct tttcattggg    1140
ctaggcatct tcttcagagt gaagttcagc aggagcgcag acgcccccgc gtaccagcag    1200
ggccagaacc agctctataa cgagctcaat ctaggacgaa gagaggagta cgatgttttg    1260
gacaagagac gtggccggga ccctgagatg ggggaaagc cgagaaggaa gaaccctcag    1320
gaaggcctgt acaatgaact gcagaaagat aagatggcgg aggcctacag tgagattggg    1380
atgaaaggcg agcgccggag gggcaagggg cacgatggcc tttaccaggg tctcagtaca    1440
gccaccaagg acacctacga cgcccttcac atgcaggccc tgccccctcg c             1491

<210> SEQ ID NO 16
<211> LENGTH: 6783
<212> TYPE: DNA
<213> ORGANISM: Artificial Sequence
<220> FEATURE:
<223> OTHER INFORMATION: plasmid DNA vector incorporating human, simian
      virus 40, E. coli, cytomegalovirus and bovine sequences

<400> SEQUENCE: 16
tagagaaatg ttctggcacc tgcacttgca ctggggacag cctatttgc tagtttgttt    60 tgtttcgttt tgttttgatg gagagcgtat gttagttacg attcacacaa aaaaccaaca    120
cacagatgta atgaaaataa agatatttta ttgcggccgc tcgagcaatt gggccctgcg    180
catgcctgct attgtcttcc caatcctccc ccttgctgtc ctgccccacc ccaccccca    240 gaatagaatg acacctactc agacaatgcg atgcaatttc ctcattttat taggaaagga    300 cagtggggagt ggcaccttcc agggtcaagg aaggcacggg ggaggggcaa acaacagatg    360
gctggcaact agaaggcaca gtcgaggctg atcagcgagc tctagcattt aggtgacact    420
atagaatagg gccctctagc gaattctcga ctcagttagc ctcccccatc tcccgggcaa    480
acgtgcgcgc caggtcgcat atcgtcggta tggagccggg ggtggtgacg tgggtctgga    540
ccatcccgga ggtaagttgc agcagggcgt cccggcagcc ggcgggcgat tggtcgtaat    600
ccaggataaa gacgtgcatg aacggaggc gtttggccaa gacgtccaag gcccaggcaa    660
acacgttata caggtcgccg ttggggcca gcaactcggg ggcccgaaac agggtaaata    720
acgtgtcccc gatatggggt cgtgggcccg cgttgctctg gggctcggca ccctggggcg    780
gcacggccgt cccgaaagc tgtccccagt cctcccgcca cgacccgccg cactgcagat    840
accgcaccgt attggcaagt agcccgtaaa cgcggcgaat cgcagccagc atagccaggt    900
ccagccgctc gccggggcgc tggcgttttgg ccaggcggtc gatgtgtctg tcctccggaa    960 gggcccccaag cacgatgttg gtgccgggca aggtcggcgg gatgagggcc acgaacgcca   1020
gcacggcctg gggggtcatg ctgcccataa ggtaccgcgc ggccgggtag cacaggaggg   1080
cggcgatggg atggcggtcg aagatgaggg tgagggccgg gggcggggca tgtgagctcc   1140
cagcctcccc cccgatatga ggagccagaa cggcgtcggt cacggcataa ggcatgccca   1200
ttgttatctg ggcgcttgtc attaccaccg ccgcgtcccc ggccgatatc tcaccctggt   1260
```

-continued

```
cgaggcggtg ttgtgtggtg tagatgttcg cgattgtctc ggaagccccc agcacccgcc    1320
agtaagtcat cggctcgggt acgtagacga tatcgtcgcg cgaacccagg gccaccagca    1380
gttgcgtggt ggtggttttc cccatcccgt ggggaccgtc tatataaacc cgcagtagcg    1440
tgggcatttt ctgctccggg cggacttccg tggcttcttg ctgccggcga gggcgcaacg    1500
ccgtacgtcg gttgctatgg ccgcgagaac gcgcagcctg gtcgaacgca gacgcgactt    1560
ctacacagcc atcggtccag acggccgcgc ttctgcgggc gatttgtgta cgcccgacag    1620
tcccggctcc ggatcggacg attgcgtcgc atcgaccctg cgcccaagct gcatcatcga    1680
aattgccgtc aaccaagctc tgatagagtt ggtcaagacc aatgcggagc atatacgccc    1740
ggagccgcgg cgatcctgca agctccggat gcctccgctc gaagtagcgc gtctgctgct    1800
ccatacaagc caaccacggc ctccagaaga agatgttggc gacctcgtat tgggaatccc    1860
cgaacatcgc ctcgctccag tcaatgaccg ctgttatgcg gccattgtcc gtcaggacat    1920
tgttggagcc gaaatccgcg tgcacgaggt gccggacttc ggggcagtcc tcggcccaaa    1980
gcatcagctc atcgagagcc tgcgcgacgg acgcactgac ggtgtcgtcc atcacagttt    2040
gccagtgata cacatgggga tcagcaatcg cgcatatgaa atcacgccat gtagtgtatt    2100
gaccgattcc ttgcggtccg aatgggccga accgctcgt ctggctaaga tcggccgcag    2160
cgatcgcatc catgagctcc gcgacgggtt gcagaacagc gggcagttcg gtttcaggca    2220
ggtcttgcaa cgtgacaccc tgtgcacggc gggagatgca ataggtcagg ctctcgctga    2280
attccccaat gtcaagcact tccggaatcg ggagcgcggc cgatgcaaag tgccgataaa    2340
cataacgatc tttgtagaaa ccatcggcgc agctatttac ccgcaggaca tatccacgcc    2400
ctcctacatc gaagctgaaa gcacgagatt cttcgccctc cgagagctgc atcaggtcgg    2460
agacgctgtc gaacttttcg atcagaaact tcgcgacaga cgtcgcggtg agttcaggct    2520
ttttcatgat ggccctccta ccggtgatct cagctgtagg aaagagaaga aggttagtag    2580
tcgacatggt ggccctccta tagtgagtcg tattatacta tgccgatata ctatgccgat    2640
gattaattgt caacactagg cgccggtcac aactaggtgg gcctatagac tctataggcg    2700
gtacttacgt cactcttggc acggggaatc cgcgttccaa tgcaccgttc ccggccgcgg    2760
aggctggatc ggtcccggtg tcttctatgg aggtcaaaac agcgtggatg gcgtctccag    2820
gcgatctgac ggttcactaa acgagctctg cttatataga cctcccaccg tacacgccta    2880
ccgcccattt gcgtcaatgg ggcggagttg ttacgacatt ttggaaagtc ccgttgattt    2940
tggtgccaaa acaaactccc attgacgtca atggggtgga gacttggaaa tccccgtgag    3000
tcaaaccgct atccacgccc attgatgtac tgccaaaacc gcatcaccat ggtaatagcg    3060
atgactaata cgtagatgta ctgccaagta ggaaagtccc ataaggtcat gtactgggca    3120
taatgccagg cgggccattt accgtcattg acgtcaatag ggggcgtact tggcatatga    3180
tacacttgat gtactgccaa gtgggcagtt taccgtaaat actccaccca ttgacgtcaa    3240
tggaaagtcc ctattggcgt tactatggga acatacgtca ttattgacgt caatgggcgg    3300
gggtcgttgg gcggtcagcc aggcgggcca tttaccgtaa gttatgtaac ggactctagc    3360
tcgatccagc tcactcccct gttgattgtg tgttatggtg cagagtccag ccactgtttg    3420
tccagtgggg tctctgacct gccttcctgt agctcttgga gtcattctgg cctcccctc    3480 ccccaagccc acacaaaaaa ccaacacaca gatccaatga aaataatgat tgtttattgc    3540
agcttaatta actagccatg accaaaaatcc cttaacgtga gttttcgttc cactgagcgt    3600 cagacccgt agaaaagatc aaaggatctt cttgagatcc ttttttttctg cgcgtaatct    3660
```

```
gctgcttgca aacaaaaaaa ccaccgctac cagcggtggt ttgtttgccg gatcaagagc    3720
taccaactct ttttccgaag gtaactggct tcagcagagc gcagatacca aatactgttc    3780
ttctagtgta gccgtagtta ggccaccact tcaagaactc tgtagcaccg cctacatacc    3840
tcgctctgct aatcctgtta ccagtggctg ctgccagtgg cgataagtcg tgtcttaccg    3900
ggttggactc aagacgatag ttaccggata aggcgcagcg gtcgggctga acgggggtt    3960 cgtgcacaca gcccagcttg gagcgaacga cctacaccga actgagatac ctacagcgtg    4020
agcattgaga aagcgccacg cttcccgaag ggagaaaggc ggacaggtat ccggtaagcg    4080
gcagggtcgg aacaggagag cgcacgaggg agcttccagg gggaaacgcc tggtatcttt    4140
atagtcctgt cgggtttcgc cacctctgac ttgagcgtcg attttttgtga tgctcgtcag    4200 gggggcggag cctatggaaa aacgccagca acgcggcctt tttacggttc ctggccttt    4260 gctggccttt tgctcacatg ttcttcgcta acatttaaat ggatctacca catttgtaga    4320
ggttttactt gctttaaaaa acctcccaca cctcccctg aacctgaaac ataaaatgaa    4380
tgcaattgtt gttgttaact tgtttattgc agcttataat ggttacaaat aaagcaatag    4440
catcacaaat ttcacaaata aagcaatagc atcacaaatt tcacaaataa agcatttttt    4500
tcactgcatt ctagttgtgg tttgtccaaa ctcatcaatg tatcttatca tgtcgagcta    4560
gctgtacaat cgatagatct aggcctcctt cgccggccgc tcagcgaggg ggcagggcct    4620
gcatgtgaag ggcgtcgtag gtgtccttgg tggctgtact gagaccctgg taaaggccat    4680 cgtgccctt gcccctccgg cgctcgcctt tcatcccaat ctcactgtag gcctccgcca    4740
tcttatcttt ctgcagttca ttgtacaggc cttcctgagg gttcttcctt ctcggctttc    4800
cccccatctc agggtcccgg ccacgtctct tgtccaaaac atcgtactcc tctcttcgtc    4860
ctagattgag ctcgttatag agctggttct ggccctgctg gtacgcgggg gcgtctcgc    4920 tcctgctgaa cttcactctg aagaagatgc ctagcccaat gaaaagcagg aggccggcga    4980
cgccccccag cacaatcagg gccatttac ctagggacag ggagaggctc ttctgtgtgt    5040
agtggttgtg cagagcctca tgcatcacgg agcatgagaa gacattcccc tcctgccacc    5100
tgctcttgtc cacggttagc ctgctgtaga ggaagaagga gccgtcggag tccagcacgg    5160
gaggcgtggt cttgtagttg ttctccggct gcccattgct ctcccactcc acggcgatgt    5220 cgctgggta gaagcctttg accaggcagg tcaggctgac ctggttcttg gtcatctcct    5280
cctgggatgg gggcagggtg tacacctgtg gctctcgggg ctgccctttg gctttggaga    5340
tggttttctc gatggaggac gggaggcctt tgttggagac cttgcacttg tactccttgc    5400
cgttcagcca gtcctggtgc aggacggtga ggacgctgac cacacggtac gtgctgttga    5460
actgctcctc ccgcgctttt gtcttggcat tatgcacctc cacgccatcc acgtaccagt    5520
tgaactggac ctcggggtct tcctggctca cgtccaccac cacgcacgtg acctcagggg    5580
tccgggagat catgagagtg tccttgggtt ttggggggaa caggaagact gatggtcccc    5640
ccaggaactc aggtgctggg catggtgggc atggggacc atatttggac tcgttgaacc    5700
gtccctcgcg aaaagttttc tttaaatgta agagcaggtc cttacaaac tgggccacct    5760 cgattttggt gtctcggaca tgcaagctgg aaaactgccc agctgagacc ttgtgcgggc    5820
agaatccgct cagcatcctc tgggtcttct cgatggcact gcagcctgac acgttgatca    5880
gggattccag ggctgcacag tacatgccag ctgtcaggtt gatgctccat accatgctgc    5940
cattgcagag cggagccttc tggttctggg tgatgttgac cagctcctca atgaggtacc    6000
tgagggctgt agagggaggc acagggcctg ggatcaggag gaatgctggg tgtggtaact    6060
```

-continued

```
cacagagcag aaggcttgtc accaggagaa gcatggtggc ggctctaggg tgatctcagc    6120
tgtaggaaag agaagaaggt tagtagtcga cgtgtccctc tcgatgaatc cgtatcaatt    6180
gtgagcgctc acaagtcaac actctttttg ataaatctag tagatatcac ttacgtaggc    6240
gccggtcaca gcttggatct gtaacggcgc agaacagaaa acgaaacaaa gacgtagagt    6300
tgagcaagca gggtcaggca aagcgtggag agccggctga gtctaggtag gctccaaggg    6360
agcgccggac aaaggcccgg tctcgacctg agctttaaac ttacctagac ggcggacgca    6420
gttcaggagg caccacaggc gggaggcggc agaacgcgac tcaaccggcg tggatggcgg    6480
cctcaggtag ggcggcgggc gcgtgaagga gagatgcgag cccctcgaag cttcagctgt    6540
gttctggcgg caaacccgtt gcgaaaaaga acgttcacgg cgactactgc acttatatac    6600
ggttctcccc caccctcggg aaaaaggcgg agccagtaca cgacatcact ttcccagttt    6660
accccgcgcc accttctcta ggcaccggtt caattgccga cccctccccc caacttctcg    6720
gggactgtgg gcgatgtgcg ctctgcccac tgacgggcac cggagcgatc gcagatcctt    6780
cga                                                                 6783
```

```
<210> SEQ ID NO 17
<211> LENGTH: 497
<212> TYPE: PRT
<213> ORGANISM: Homo sapiens

<400> SEQUENCE: 17

Met Leu Leu Leu Val Thr Ser Leu Leu Cys Glu Leu Pro His Pro
1               5                   10                  15

Ala Phe Leu Leu Ile Pro Gly Pro Val Pro Pro Ser Thr Ala Leu Arg
            20                  25                  30

Tyr Leu Ile Glu Glu Leu Val Asn Ile Thr Gln Asn Gln Lys Ala Pro
        35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Glu Ser Lys Tyr Gly Pro Pro Cys Pro Pro
    130                 135                 140

Cys Pro Ala Pro Glu Phe Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
        195                 200                 205

Glu Glu Gln Phe Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
```

```
                        245                 250                 255
Gly Gln Pro Arg Glu Pro Gln Val Tyr Thr Leu Pro Pro Ser Gln Glu
                260                 265                 270

Glu Met Thr Lys Asn Gln Val Ser Leu Thr Cys Leu Val Lys Gly Phe
            275                 280                 285

Tyr Pro Ser Asp Ile Ala Val Glu Trp Glu Ser Asn Gly Gln Pro Glu
        290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
                325                 330                 335

Asn Val Phe Ser Cys Ser Val Met His Glu Ala Leu His Asn His Tyr
            340                 345                 350

Thr Gln Lys Ser Leu Ser Leu Ser Leu Gly Lys Met Ala Leu Ile Val
        355                 360                 365

Leu Gly Gly Val Ala Gly Leu Leu Leu Phe Ile Gly Leu Gly Ile Phe
    370                 375                 380

Phe Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 18
<211> LENGTH: 691
<212> TYPE: PRT
<213> ORGANISM: Artificial Sequence
<220> FEATURE:
<223> OTHER INFORMATION: selection/ suicide fusion coding region
      containing herpes simplex virus and E.coli sequences

<400> SEQUENCE: 18

Met Lys Lys Pro Glu Leu Thr Ala Thr Ser Val Ala Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110
```

```
Gln Pro Val Ala Glu Leu Met Asp Ala Ile Ala Ala Asp Leu Ser
            115                 120                 125
Gln Thr Ser Gly Phe Gly Pro Phe Gly Pro Gln Gly Ile Gly Gln Tyr
            130                 135                 140
Thr Thr Trp Arg Asp Phe Ile Cys Ala Ile Ala Asp Pro His Val Tyr
145                 150                 155                 160
His Trp Gln Thr Val Met Asp Asp Thr Val Ser Ala Ser Val Ala Gln
                165                 170                 175
Ala Leu Asp Glu Leu Met Leu Trp Ala Glu Asp Cys Pro Glu Val Arg
            180                 185                 190
His Leu Val His Ala Asp Phe Gly Ser Asn Asn Val Leu Thr Asp Asn
            195                 200                 205
Gly Arg Ile Thr Ala Val Ile Asp Trp Ser Glu Ala Met Phe Gly Asp
210                 215                 220
Ser Gln Tyr Glu Val Ala Asn Ile Phe Phe Trp Arg Pro Trp Leu Ala
225                 230                 235                 240
Cys Met Glu Gln Gln Thr Arg Tyr Phe Glu Arg Arg His Pro Glu Leu
                245                 250                 255
Ala Gly Ser Pro Arg Leu Arg Ala Tyr Met Leu Arg Ile Gly Leu Asp
            260                 265                 270
Gln Leu Tyr Gln Ser Leu Val Asp Gly Asn Phe Asp Asp Ala Ala Trp
            275                 280                 285
Ala Gln Gly Arg Cys Asp Ala Ile Val Arg Ser Gly Ala Gly Thr Val
            290                 295                 300
Gly Arg Thr Gln Ile Ala Arg Arg Ser Ala Ala Val Trp Thr Asp Gly
305                 310                 315                 320
Cys Val Glu Val Ala Ser Ala Phe Asp Gln Ala Ala Arg Ser Arg Gly
                325                 330                 335
His Ser Asn Arg Arg Thr Ala Leu Arg Pro Arg Gln Gln Glu Ala
            340                 345                 350
Thr Glu Val Arg Pro Glu Gln Lys Met Pro Thr Leu Leu Arg Val Tyr
            355                 360                 365
Ile Asp Gly Pro His Gly Met Gly Lys Thr Thr Thr Gln Leu Leu
            370                 375                 380
Val Ala Leu Gly Ser Arg Asp Asp Ile Val Tyr Val Pro Glu Pro Met
385                 390                 395                 400
Thr Tyr Trp Arg Val Leu Gly Ala Ser Glu Thr Ile Ala Asn Ile Tyr
                405                 410                 415
Thr Thr Gln His Arg Leu Asp Gln Gly Glu Ile Ser Ala Gly Asp Ala
            420                 425                 430
Ala Val Val Met Thr Ser Ala Gln Ile Thr Met Gly Met Pro Tyr Ala
            435                 440                 445
Val Thr Asp Ala Val Leu Ala Pro His Ile Gly Gly Glu Ala Gly Ser
450                 455                 460
Ser His Ala Pro Pro Ala Leu Thr Leu Ile Phe Asp Arg His Pro
465                 470                 475                 480
Ile Ala Ala Leu Leu Cys Tyr Pro Ala Ala Arg Tyr Leu Met Gly Ser
                485                 490                 495
Met Thr Pro Gln Ala Val Leu Ala Phe Val Ala Leu Ile Pro Pro Thr
            500                 505                 510
Leu Pro Gly Thr Asn Ile Val Leu Gly Ala Leu Pro Glu Asp Arg His
            515                 520                 525
Ile Asp Arg Leu Ala Lys Arg Gln Arg Pro Gly Glu Arg Leu Asp Leu
```

```
                530             535             540
Ala Met Leu Ala Ala Ile Arg Arg Val Tyr Gly Leu Leu Ala Asn Thr
545                 550                 555                 560

Val Arg Tyr Leu Gln Cys Gly Gly Ser Trp Arg Glu Asp Trp Gly Gln
                565                 570                 575

Leu Ser Gly Thr Ala Val Pro Pro Gln Gly Ala Glu Pro Gln Ser Asn
                580                 585                 590

Ala Gly Pro Arg Pro His Ile Gly Asp Thr Leu Phe Thr Leu Phe Arg
                595                 600                 605

Ala Pro Glu Leu Leu Ala Pro Asn Gly Asp Leu Tyr Asn Val Phe Ala
610                 615                 620

Trp Ala Leu Asp Val Leu Ala Lys Arg Leu Arg Ser Met His Val Phe
625                 630                 635                 640

Ile Leu Asp Tyr Asp Gln Ser Pro Ala Gly Cys Arg Asp Ala Leu Leu
                645                 650                 655

Gln Leu Thr Ser Gly Met Val Gln Thr His Val Thr Thr Pro Gly Ser
                660                 665                 670

Ile Pro Thr Ile Cys Asp Leu Ala Arg Thr Phe Ala Arg Glu Met Gly
                675                 680                 685

Glu Ala Asn
690

<210> SEQ ID NO 19
<211> LENGTH: 6770
<212> TYPE: DNA
<213> ORGANISM: Artificial Sequence
<220> FEATURE:
<223> OTHER INFORMATION: alternate plasmid DNA vector incorporating
      human, simian virus 40, E. coli, cytomegalovirus and bovine
      sequences

<400> SEQUENCE: 19
tcgaaggatc tgcgatcgct ccggtgcccg tcagtgggca gagcgcacat cgcccacagt      60
ccccgagaag ttgggggggag gggtcggcaa ttgaaccggt gcctagagaa ggtggcgcgg    120
ggtaaactgg gaaagtgatg tcgtgtactg gctccgcctt tttcccgagg gtggggagaa    180
accgtatata agtgcagtag tcgccgtgaa cgttcttttt cgcaacgggt ttgccgccag    240
aacacagctg aagcttcgag gggctcgcat ctctccttca cgcgcccgcc gcctacctg     300
aggccgccat ccacgccggt tgagtcgcgt tctgccgcct cccgcctgtg gtgcctcctg    360
aactgcgtcc gccgtctagg taagtttaaa gctcaggtcg agaccgggcc tttgtccggc    420
gctcccttgg agcctaccta gactcagccg gctctccacg ctttgcctga ccctgcttgc    480
tcaactctac gtctttgttt cgttttctgt tctgcgccgt tacagatcca agctgtgacc    540
ggcgcctacg taagtgatat ctactagatt tatcaaaaag agtgttgact tgtgagcgct    600
cacaattgat acggattcat cgagagggac acgtcgacta ctaaccttct tctctttcct    660
acagctgaga tcaccctaga gccgccacca tgcttctcct ggtgacaagc cttctgctct    720
gtgagttacc acacccagca ttcctcctga tcccaggccc tgtgcctccc tctacagccc    780
tcaggtacct cattgaggag ctggtcaaca tcacccagaa ccagaaggct ccgctctgca    840
atggcagcat ggtatggagc atcaacctga gctggcat gtactgtgca gccctggaat    900
ccctgatcaa cgtgtcaggc tgcagtgcca tcgagaagac ccagaggatg ctgagcggat    960
tctgccccgca caaggtctca gctgggcagt tttccagctt gcatgtccga gacaccaaaa   1020
tcgaggtggc ccagtttgta aaggacctgc tcttacattt aaagaaactt tttcgcgagg   1080
```

```
gacggttcaa cgagtccaaa tatggtcccc catgcccacc atgcccagca cctgagttcc    1140
tggggggacc atcagtcttc ctgttccccc caaaacccaa ggacactctc atgatctccc    1200
ggacccctga ggtcacgtgc gtggtggtgg acgtgagcca ggaagacccc gaggtccagt    1260
tcaactggta cgtggatggc gtggaggtgc ataatgccaa gacaaagccg cgggaggagc    1320
agttcaacag cacgtaccgt gtggtcagcg tcctcaccgt cctgcaccag gactggctga    1380
acggcaagga gtacaagtgc aaggtctcca acaaaggcct cccgtcctcc atcgagaaaa    1440
ccatctccaa agccaaaggg cagcccgag agccacaggt gtacaccctg cccccatccc    1500
aggaggagat gaccaagaac caggtcagcc tgacctgcct ggtcaaaggc ttctaccca    1560 gcgacatcgc cgtggagtgg gagagcaatg ggcagccgga gaacaactac aagaccacgc    1620
ctcccgtgct ggactccgac ggctccttct cctctacag caggctaacc gtggacaaga    1680
gcaggtggca ggaggggaat gtcttctcat gctccgtgat gcatgaggct ctgcacaacc    1740
actacacaca gaagagcctc tccctgtccc taggtaaaat ggccctgatt gtgctggggg    1800
gcgtcgccgg cctcctgctt ttcattgggc taggcatctt cttcagagtg aagttcagca    1860
ggagcgcaga cgcccccgcg taccagcagg gccagaacca gctctataac gagctcaatc    1920
taggacgaag agaggagtac gatgttttgg acaagagacg tggccgggac cctgagatgg    1980
ggggaaagcc gagaaggaag aaccctcagg aaggcctgta caatgaactg cagaaagata    2040
agatggcgga ggcctacagt gagattggga tgaaaggcga gcgccggagg ggcaaggggc    2100
acgatggcct ttaccagggt ctcagtacag ccaccaagga cacctacgac gcccttcaca    2160
tgcaggccct gcccctcgc tgagcggccg gcgaaggagg cctagatcta tcgattgtac    2220
agctagctcg acatgataag atacattgat gagtttggac aaaccacaac tagaatgcag    2280 tgaaaaaat gctttatttg tgaaatttgt gatgctattg ctttatttgt gaaatttgtg    2340
atgctattgc tttatttgta accattataa gctgcaataa acaagttaac aacaacaatt    2400
gcattcattt tatgtttcag gttcaggggg aggtgtggga ggttttttaa agcaagtaaa    2460
acctctacaa atgtggtaga tccatttaaa tgttagcgaa gaacatgtga gcaaaaggcc    2520
agcaaaaggc caggaaccgt aaaaaggccg cgttgctggc gttttccat aggctccgcc    2580 ccctgacga gcatcacaaa aatcgacgct caagtcagag gtggcgaaac ccgacaggac    2640 tataagata ccaggcgttt ccccctggaa gctccctcgt gcgctctcct gttccgaccc    2700
tgccgcttac cggatacctg tccgcctttc tcccttcggg aagcgtggcg ctttctcaat    2760
gctcacgctg taggtatctc agttcggtgt aggtcgttcg ctccaagctg gctgtgtgc    2820 acgaaccccc cgttcagccc gaccgctgcg ccttatccgg taactatcgt cttgagtcca    2880
acccggtaag acacgactta tcgccactgg cagcagccac tggtaacagg attagcagag    2940
cgaggtatgt aggcggtgct acagagttct tgaagtggtg gcctaactac ggctacacta    3000
gaagaacagt atttggtatc tgcgctctgc tgaagccagt taccttcgga aaagagttg    3060 gtagctcttg atccggcaaa caaaccaccg ctggtagcgg tggtttttt gtttgcaagc    3120 agcagattac gcgcagaaaa aaaggatctc aagaagatcc tttgatcttt tctacggggt    3180
ctgacgctca gtggaacgaa aactcacgtt aagggatttt ggtcatggct agttaattaa    3240
gctgcaataa acaatcatta ttttcattgg atctgtgtgt tggttttttg tgtgggcttg    3300
ggggaggggg aggccagaat gactccaaga gctacaggaa ggcaggtcag agaccccact    3360
ggacaaacag tggctggact ctgcaccata acacacaatc aacaggggag tgagctggat    3420
cgagctagag tccgttacat aacttacggt aaatggcccg cctggctgac cgcccaacga    3480
```

```
cccccgccca ttgacgtcaa taatgacgta tgttcccata gtaacgccaa tagggacttt    3540
ccattgacgt caatgggtgg agtatttacg gtaaactgcc cacttggcag tacatcaagt    3600
gtatcatatg ccaagtacgc ccCctattga cgtcaatgac ggtaaatggc ccgcctggca    3660
ttatgcccag tacatgacct tatgggactt tcctacttgg cagtacatct acgtattagt    3720
catcgctatt accatggtga tgcggttttg gcagtacatc aatgggcgtg gatagcggtt    3780
tgactcacgg ggatttccaa gtctccaccc cattgacgtc aatgggagtt tgttttggca    3840
ccaaaatcaa cgggactttc caaaatgtcg taacaactcc gccccattga cgcaaatggg    3900
cggtaggcgt gtacggtggg aggtctatat aagcagagct cgtttagtga accgtcagat    3960
cgcctggaga cgccatccac gctgttttga cctccataga agacaccggg accgatccag    4020
cctccgcggc cgggaacggt gcattggaac gcggattccc cgtgccaaga gtgacgtaag    4080
taccgcctat agagtctata ggcccaccta gttgtgaccg cgcctagtg ttgacaatta    4140 atcatcggca tagtataata cgactcacta taggagggcc accatgtcga ctactaacct    4200
tcttctcttt cctacagctg agatcaccgg taggagggcc atcatgaaaa agcctgaact    4260
caccgcgacg tctgtcgcga agtttctgat cgaaaagttc gacagcgtct ccgacctgat    4320
gcagctctcg gagggcgaag aatctcgtgc tttcagcttc gatgtaggag ggcgtggata    4380
tgtcctgcgg gtaaatagct gcgccgatgg ttttctacaaa gatcgttatg tttatcggca    4440
ctttgcatcg gccgcgctcc cgattccgga agtgcttgac attggggaat tcagcgagag    4500
cctgacctat tgcatctccc gccgtgcaca gggtgtcacg ttgcaagacc tgcctgaaac    4560
cgaactgccc gctgttctgc aacccgtcgc ggagctcatg gatgcgatcg ctgcggccga    4620
tcttagccag acgagcgggt tcggcccatt cggaccgcaa ggaatcggtc aatacactac    4680
atggcgtgat ttcatatgcg cgattgctga tccccatgtg tatcactggc aaactgtgat    4740
ggacgacacc gtcagtgcgt ccgtcgcgca ggctctcgat gagctgatgc tttgggccga    4800
ggactgcccc gaagtccggc acctcgtgca cgcggatttc ggctccaaca atgtcctgac    4860
ggacaatggc cgcataacag cggtcattga ctggagcgag gcgatgttcg gggattccca    4920
atacgaggtc gccaacatct tcttctggag gccgtggttg gcttgtatgg agcagcagac    4980
gcgctacttc gagcggaggc atccggagct tgcaggatcg ccgcggctcc gggcgtatat    5040
gctccgcatt ggtcttgacc aactctatca gagcttggtt gacggcaatt tcgatgatgc    5100
agcttgggcg cagggtcgat gcgacgcaat cgtccgatcc ggagccggga ctgtcgggcg    5160
tacacaaatc gcccgcagaa gcgcggccgt ctggaccgat ggctgtgtag aagtcgcgtc    5220
tgcgttcgac caggctgcgc gttctcgcgg ccatagcaac cgacgtacgg cgttgcgccc    5280
tcgccggcag caagaagcca cggaagtccg cccggagcag aaaatgccca cgctactgcg    5340
ggtttatata cggtccccc acgggatggg gaaaaccacc accacgcaac tgctggtggc    5400
cctgggttcg cgcgacgata tcgtctacgt acccgagccg atgacttact ggcgggtgct    5460
gggggcttcc gagacaatcg cgaacatcta caccacacaa caccgcctcg accagggtga    5520
gatatcggcc ggggacgcgg cggtggtaat gacaagcgcc cagataacaa tgggcatgcc    5580
ttatgccgtg accgacgccg ttctggctcc tcatatcggg ggggaggctg ggagctcaca    5640
tgccccgccc ccgccctca ccctcatctt gaccgccat cccatcgccg ccctcctgtg    5700
ctacccggcc gcgcggtacc ttatgggcag catgaccccc caggccgtgc tggcgttcgt    5760
ggccctcatc ccgccgacct tgcccggcac caacatcgtg cttggggccc ttccggagga    5820
cagacacatc gaccgcctgg ccaaacgcca gcgccccggc gagcggctgg acctggctat    5880
```

```
gctggctgcg attcgccgcg tttacgggct acttgccaat acggtgcggt atctgcagtg    5940
cggcgggtcg tggcgggagg actggggaca gctttcgggg acggccgtgc cgccccaggg    6000
tgccgagccc cagagcaacg cgggcccacg accccatatc ggggacacgt tatttaccct    6060
gtttcgggcc cccgagttgc tggccccaa cggcgacctg tataacgtgt ttgcctgggc     6120
cttggacgtc ttggccaaac gcctccgttc catgcacgtc tttatcctgg attacgacca    6180
atcgcccgcc ggctgccggg acgccctgct gcaacttacc tccgggatgg tccagaccca    6240
cgtcaccacc cccggctcca taccgacgat atgcgacctg gcgcgcacgt ttgcccggga    6300
gatggggag ctaactgag tcgagaattc gctagagggc cctattctat agtgtcacct      6360
aaatgctaga gctcgctgat cagcctcgac tgtgccttct agttgccagc catctgttgt    6420
ttgcccctcc cccgtgcctt ccttgaccct ggaaggtgcc actccactg tcctttccta     6480
ataaaatgag gaaattgcat cgcattgtct gagtaggtgt cattctattc tgggggtgg     6540
ggtggggcag gacagcaagg gggaggattg ggaagacaat agcaggcatg cgcagggccc    6600
aattgctcga gcggccgcaa taaaatatct ttattttcat tacatctgtg tgttggtttt    6660
ttgtgtgaat cgtaactaac atacgctctc catcaaaaca aaacgaaaca aaacaaacta    6720
gcaaaatagg ctgtccccag tgcaagtgca ggtgccagaa catttctcta               6770
```

<210> SEQ ID NO 20
<211> LENGTH: 6770
<212> TYPE: DNA
<213> ORGANISM: Artificial Sequence
<220> FEATURE:
<223> OTHER INFORMATION: alternate plasmid DNA vector incorporating
      human, simian virus 40, E. coli, cytomegalovirus and bovine
      sequences

<400> SEQUENCE: 20

```
tagagaaatg ttctggcacc tgcacttgca ctggggacag cctatttgc tagtttgttt     60
tgtttcgttt tgttttgatg gagagcgtat gttagttacg attcacacaa aaaaccaaca    120
cacagatgta atgaaaataa agatatttta ttgcggccgc tcgagcaatt gggcccgcg     180
catgcctgct attgtcttcc caatcctccc ccttgctgtc ctgccccacc ccacccccca    240
gaatagaatg acacctactc agacaatgcg atgcaatttc ctcattttat taggaaagga    300
cagtgggagt ggcaccttcc agggtcaagg aaggcacggg ggaggggcaa acaacagatg    360
gctggcaact agaaggcaca gtcgaggctg atcagcgagc tctagcattt aggtgacact    420
atagaatagg gccctctagc gaattctcga ctcagttagc ctcccccatc tcccgggcaa    480
acgtgcgcgc caggtcgcat atcgtcggta tggagccggg ggtggtgacg tgggtctgga    540
ccatcccgga ggtaagttgc agcagggcgt cccggcagcc ggcgggcgat tggtcgtaat    600
ccaggataaa gacgtgcatg gaacggaggc gtttggccaa gacgtccaag gcccaggcaa    660
acacgttata caggtcgccg ttgggggcca gcaactcggg ggcccgaaac agggtaaata    720
acgtgtcccc gatatggggt cgtgggcccg cgttgctctg gggctcggca ccctggggcg    780
gcacggccgt ccccgaaagc tgtccccagt cctcccgcca cgaccgccg cactgcagat     840
accgcaccgt attggcaagt agcccgtaaa cgcggcgaat cgcagccagc atagccaggt    900
ccagccgctc gccggggcgc tggcgttttgg ccaggcggtc gatgtgtctg tcctccggaa    960
gggccccaag cacgatgttg gtgccgggca aggtcggcgg gatgagggcc acgaacgcca    1020
gcacggcctg gggggtcatg ctgcccataa ggtaccgcgc ggccgggtag cacaggaggg    1080
cggcgatggg atggcggtcg aagatgaggg tgagggccgg gggcggggca tgtgagctcc    1140
```

```
cagcctcccc cccgatatga ggagccagaa cggcgtcggt cacggcataa ggcatgccca    1200
ttgttatctg ggcgcttgtc attaccaccg ccgcgtcccc ggccgatatc tcaccctggt    1260
cgaggcggtg ttgtgtggtg tagatgttcg cgattgtctc ggaagccccc agcacccgcc    1320
agtaagtcat cggctcgggt acgtagacga tatcgtcgcg cgaacccagg ccaccagca    1380
gttgcgtggt ggtggttttc cccatcccgt ggggaccgtc tatataaacc cgcagtagcg    1440
tgggcatttt ctgctccggg cggacttccg tggcttcttg ctgccggcga gggcgcaacg    1500
ccgtacgtcg gttgctatgg ccgcgagaac gcgcagcctg gtcgaacgca gacgcgactt    1560
ctacacagcc atcggtccag acggccgcgc ttctgcgggc gatttgtgta cgcccgacag    1620
tcccggctcc ggatcggacg attgcgtcgc atcgaccctg cgcccaagct gcatcatcga    1680
aattgccgtc aaccaagctc tgatagagtt ggtcaagacc aatgcggagc atatacgccc    1740
ggagccgcgg cgatcctgca agctccggat gcctccgctc gaagtagcgc gtctgctgct    1800
ccatacaagc caaccacggc ctccagaaga agatgttggc gacctcgtat tgggaatccc    1860
cgaacatcgc ctcgctccag tcaatgaccg ctgttatgcg gccattgtcc gtcaggacat    1920
tgttggagcc gaaatccgcg tgcacgaggt gccggacttc ggggcagtcc tcggcccaaa    1980
gcatcagctc atcgagagcc tgcgcgacgg acgcactgac ggtgtcgtcc atcacagttt    2040
gccagtgata cacatgggga tcagcaatcg cgcatatgaa atcacgccat gtagtgtatt    2100
gaccgattcc ttgcggtccg aatgggccga accgctcgt ctggctaaga tcggccgcag    2160
cgatcgcatc catgagctcc gcgacgggtt gcagaacagc gggcagttcg gtttcaggca    2220
ggtcttgcaa cgtgacaccc tgtgcacggc gggagatgca ataggtcagg ctctcgctga    2280
attccccaat gtcaagcact tccggaatcg ggagcgcggc cgatgcaaag tgccgataaa    2340
cataacgatc tttgtagaaa ccatcggcgc agctatttac ccgcaggaca tatccacgcc    2400
ctcctacatc gaagctgaaa gcacgagatt cttcgccctc cgagagctgc atcaggtcgg    2460
agacgctgtc gaacttttcg atcagaaact tcgcgacaga cgtcgcggtg agttcaggct    2520
ttttcatgat ggccctccta ccggtgatct cagctgtagg aaagagaaga aggttagtag    2580
tcgacatggt ggccctccta tagtgagtcg tattatacta tgccgatgat taattgtcaa    2640
cactaggcgc cggtcacaac taggtgggcc tatagactct ataggcggta cttacgtcac    2700
tcttggcacg gggaatccgc gttccaatgc accgttcccg gccgcggagg ctggatcggt    2760
cccggtgtct tctatggagg tcaaaacagc gtggatggcg tctccaggcg atctgacggt    2820
tcactaaacg agctctgctt atatagacct cccaccgtac acgcctaccg cccatttgcg    2880
tcaatggggc ggagttgtta cgacattttg gaaagtcccg ttgattttgg tgccaaaaca    2940
aactcccatt gacgtcaatg gggtggagac ttggaaatcc ccgtgagtca accgctatc    3000
cacgcccatt gatgtactgc caaaaccgca tcaccatggt aatagcgatg actaatacgt    3060
agatgtactg ccaagtagga aagtcccata aggtcatgta ctgggcataa tgccaggcgg    3120
gccatttacc gtcattgacg tcaataggggg gcgtacttgg catatgatac acttgatgta    3180
ctgccaagtg ggcagtttac cgtaaatact ccaccattg acgtcaatgg aaagtcccta    3240
ttggcgttac tatgggaaca tacgtcatta ttgacgtcaa tgggcggggg tcgttgggcg    3300
gtcagccagg cgggccatt accgtaagtt atgtaacgga ctctagctcg atccagctca    3360
ctccccctgtt gattgtgtgt tatggtgcag agtccagcca ctgtttgtcc agtggggtct    3420
ctgacctgcc ttcctgtagc tcttggagtc attctggcct ccccctcccc caagcccaca    3480
caaaaaacca acacacagat ccaatgaaaa taatgattgt ttattgcagc ttaattaact    3540
```

```
agccatgacc aaaatccctt aacgtgagtt ttcgttccac tgagcgtcag accccgtaga    3600
aaagatcaaa ggatcttctt gagatccttt ttttctgcgc gtaatctgct gcttgcaaac    3660
aaaaaaacca ccgctaccag cggtggtttg tttgccggat caagagctac caactctttt    3720
tccgaaggta actggcttca gcagagcgca gataccaaat actgttcttc tagtgtagcc    3780
gtagttaggc caccacttca agaactctgt agcaccgcct acatacctcg ctctgctaat    3840
cctgttacca gtggctgctg ccagtggcga taagtcgtgt cttaccgggt tggactcaag    3900
acgatagtta ccggataagg cgcagcggtc gggctgaacg gggggttcgt gcacacagcc    3960
cagcttggag cgaacgacct acaccgaact gagataccta cagcgtgagc attgagaaag    4020
cgccacgctt cccgaaggga gaaaggcgga caggtatccg gtaagcggca gggtcggaac    4080
aggagagcgc acgagggagc ttccaggggg aaacgcctgg tatctttata gtcctgtcgg    4140
gtttcgccac ctctgacttg agcgtcgatt tttgtgatgc tcgtcagggg ggcggagcct    4200
atggaaaaac gccagcaacg cggcttttt  acggttcctg gccttttgct ggccttttgc    4260
tcacatgttc ttcgctaaca tttaaatgga tctaccacat ttgtagaggt tttacttgct    4320
ttaaaaaacc tcccacacct cccctgaac  ctgaaacata aaatgaatgc aattgttgtt    4380
gttaacttgt ttattgcagc ttataatggt tacaaataaa gcaatagcat cacaaatttc    4440
acaaataaag caatagcatc acaaatttca caaataaagc attttttca  ctgcattcta    4500 gttgtggttt gtccaaactc atcaatgtat cttatcatgt cgagctagct gtacaatcga    4560
tagatctagg cctccttcgc cggccgctca gcgaggggc  agggcctgca tgtgaagggc    4620
gtcgtaggtg tccttggtgg ctgtactgag accctggtaa aggccatcgt gccccttgcc    4680
cctccggcgc tcgccttca  tcccaatctc actgtaggcc tccgccatct tatctttctg    4740
cagttcattg tacaggcctt cctgagggtt cttccttctc ggctttcccc ccatctcagg    4800
gtcccggcca cgtctcttgt ccaaaacatc gtactcctct cttcgtccta gattgagctc    4860
gttatagagc tggttctggc cctgctggta cgcgggggcg tctgcgctcc tgctgaactt    4920
cactctgaag aagatgccta gcccaatgaa aagcaggagg ccggcgacgc ccccagcac    4980 aatcagggcc attttaccta gggacaggga gaggctcttc tgtgtgtagt ggttgtgcag    5040
agcctcatgc atcacggagc atgagaagac attcccctcc tgccacctgc tcttgtccac    5100
ggttagcctg ctgtagagga agaaggagcc gtcggagtcc agcacgggag gcgtggtctt    5160
gtagttgttc tccggctgcc cattgctctc ccactccacg gcgatgtcgc tggggtagaa    5220
gcctttgacc aggcaggtca ggctgacctg gttcttggtc atctcctcct gggatgggg     5280 cagggtgtac acctgtggct ctcggggctg ccctttggct ttggagatgg ttttctcgat    5340
ggaggacggg aggcctttgt tggagacctt gcacttgtac tccttgccgt tcagccagtc    5400
ctggtgcagg acgtgagga  cgctgaccac acggtacgtg ctgttgaact gctcctcccg    5460
cggctttgtc ttggcattat gcacctccac gccatccacg taccagttga actgaccctc    5520
ggggtcttcc tggctcacgt ccaccaccac gcacgtgacc tcagggtcc  gggagatcat    5580 gagagtgtcc ttgggtttg  ggggaacag  gaagactgat ggtcccccca ggaactcagg    5640
tgctgggcat ggtgggcatg ggggaccata tttggactcg ttgaaccgtc cctcgcgaaa    5700
aagtttcttt aaatgtaaga gcaggtcctt tacaaactgg gccacctcga ttttggtgtc    5760
tcggacatgc aagctggaaa actgcccagc tgagaccttg tgcgggcaga atccgctcag    5820
catcctctgg gtcttctcga tggcactgca gcctgacacg ttgatcaggg attccagggc    5880
tgcacagtac atgccagctg tcaggttgat gctccatacc atgctgccat tgcagagcgg    5940
```

-continued

```
agccttctgg ttctgggtga tgttgaccag ctcctcaatg aggtacctga gggctgtaga    6000
gggaggcaca gggcctggga tcaggaggaa tgctgggtgt ggtaactcac agagcagaag    6060
gcttgtcacc aggagaagca tggtggcggc tctagggtga tctcagctgt aggaaagaga    6120
agaaggttag tagtcgacgt gtccctctcg atgaatccgt atcaattgtg agcgctcaca    6180
agtcaacact cttttttgata aatctagtag atatcactta cgtaggcgcc ggtcacagct    6240
tggatctgta acggcgcaga acagaaaacg aaacaaagac gtagagttga gcaagcaggg    6300
tcaggcaaag cgtggagagc cggctgagtc taggtaggct ccaagggagc gccggacaaa    6360
ggcccggtct cgacctgagc tttaaactta cctagacggc ggacgcagtt caggaggcac    6420
cacaggcggg aggcggcaga acgcgactca accggcgtgg atggcggcct caggtagggc    6480
ggcgggcgcg tgaaggagag atgcgagccc ctcgaagctt cagctgtgtt ctggcggcaa    6540
acccgttgcg aaaagaacg ttcacggcga ctactgcact tatatacggt tctcccccac    6600
cctcgggaaa aaggcggagc cagtacacga catcactttc ccagtttacc ccgcgccacc    6660
ttctctaggc accggttcaa ttgccgaccc ctcccccaa cttctcgggg actgtgggcg    6720
atgtgcgctc tgcccactga cgggcaccgg agcgatcgca gatccttcga    6770
```

<210> SEQ ID NO 21
<211> LENGTH: 691
<212> TYPE: PRT
<213> ORGANISM: Homo sapiens
<400> SEQUENCE: 21

```
Met Lys Lys Pro Glu Leu Thr Ala Thr Ser Val Ala Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Leu Met Asp Ala Ile Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240
```

```
Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Ala Ser Ala Phe Asp Gln Ala Ala Arg Ser Arg Gly
                325                 330                 335

His Ser Asn Arg Arg Thr Ala Leu Arg Pro Arg Gln Gln Glu Ala
            340                 345                 350

Thr Glu Val Arg Pro Glu Gln Lys Met Pro Thr Leu Leu Arg Val Tyr
        355                 360                 365

Ile Asp Gly Pro His Gly Met Gly Lys Thr Thr Thr Gln Leu Leu
    370                 375                 380

Val Ala Leu Gly Ser Arg Asp Asp Ile Val Tyr Val Pro Glu Pro Met
385                 390                 395                 400

Thr Tyr Trp Arg Val Leu Gly Ala Ser Glu Thr Ile Ala Asn Ile Tyr
                405                 410                 415

Thr Thr Gln His Arg Leu Asp Gln Gly Glu Ile Ser Ala Gly Asp Ala
            420                 425                 430

Ala Val Val Met Thr Ser Ala Gln Ile Thr Met Gly Met Pro Tyr Ala
        435                 440                 445

Val Thr Asp Ala Val Leu Ala Pro His Ile Gly Gly Glu Ala Gly Ser
    450                 455                 460

Ser His Ala Pro Pro Ala Leu Thr Leu Ile Phe Asp Arg His Pro
465                 470                 475                 480

Ile Ala Ala Leu Leu Cys Tyr Pro Ala Ala Arg Tyr Leu Met Gly Ser
                485                 490                 495

Met Thr Pro Gln Ala Val Leu Ala Phe Val Ala Leu Ile Pro Pro Thr
            500                 505                 510

Leu Pro Gly Thr Asn Ile Val Leu Gly Ala Leu Pro Glu Asp Arg His
        515                 520                 525

Ile Asp Arg Leu Ala Lys Arg Gln Arg Pro Gly Glu Arg Leu Asp Leu
    530                 535                 540

Ala Met Leu Ala Ala Ile Arg Arg Val Tyr Gly Leu Leu Ala Asn Thr
545                 550                 555                 560

Val Arg Tyr Leu Gln Cys Gly Gly Ser Trp Arg Glu Asp Trp Gly Gln
                565                 570                 575

Leu Ser Gly Thr Ala Val Pro Pro Gln Gly Ala Glu Pro Gln Ser Asn
            580                 585                 590

Ala Gly Pro Arg Pro His Ile Gly Asp Thr Leu Phe Thr Leu Phe Arg
        595                 600                 605

Ala Pro Glu Leu Leu Ala Pro Asn Gly Asp Leu Tyr Asn Val Phe Ala
    610                 615                 620

Trp Ala Leu Asp Val Leu Ala Lys Arg Leu Arg Ser Met His Val Phe
625                 630                 635                 640

Ile Leu Asp Tyr Asp Gln Ser Pro Ala Gly Cys Arg Asp Ala Leu Leu
                645                 650                 655

Gln Leu Thr Ser Gly Met Val Gln Thr His Val Thr Thr Pro Gly Ser
```

```
                    660                 665                 670
Ile Pro Thr Ile Cys Asp Leu Ala Arg Thr Phe Ala Arg Glu Met Gly
                675                 680                 685

Glu Ala Asn
        690

<210> SEQ ID NO 22
<211> LENGTH: 497
<212> TYPE: PRT
<213> ORGANISM: Artificial Sequence
<220> FEATURE:
<223> OTHER INFORMATION: IL13 cytokine fused to Fc:zeta

<400> SEQUENCE: 22

Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Leu Arg
                20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
 50                 55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Glu Ser Lys Tyr Gly Pro Pro Cys Pro Pro
130                 135                 140

Cys Pro Ala Pro Glu Phe Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
        195                 200                 205

Glu Glu Gln Phe Asn Ser Thr Tyr Arg Val Val Ser Val Leu Thr Val
210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
                245                 250                 255

Gly Gln Pro Arg Glu Pro Gln Val Tyr Thr Leu Pro Pro Ser Gln Glu
            260                 265                 270

Glu Met Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
                325                 330                 335
```

```
Asn Val Phe Ser Cys Ser Val Met His Glu Ala Leu His Asn His Tyr
            340                 345                 350
Thr Gln Lys Ser Leu Ser Leu Ser Leu Gly Lys Met Ala Leu Ile Val
        355                 360                 365
Leu Gly Gly Val Ala Gly Leu Leu Leu Phe Ile Gly Leu Gly Ile Phe
    370                 375                 380
Phe Arg Val Lys Phe Ser Arg Ser Ala Asp Ala Pro Ala Tyr Gln Gln
385                 390                 395                 400
Gly Gln Asn Gln Leu Tyr Asn Glu Leu Asn Leu Gly Arg Arg Glu Glu
                405                 410                 415
Tyr Asp Val Leu Asp Lys Arg Arg Gly Arg Asp Pro Glu Met Gly Gly
            420                 425                 430
Lys Pro Arg Arg Lys Asn Pro Gln Glu Gly Leu Tyr Asn Glu Leu Gln
        435                 440                 445
Lys Asp Lys Met Ala Glu Ala Tyr Ser Glu Ile Gly Met Lys Gly Glu
    450                 455                 460
Arg Arg Arg Gly Lys Gly His Asp Gly Leu Tyr Gln Gly Leu Ser Thr
465                 470                 475                 480
Ala Thr Lys Asp Thr Tyr Asp Ala Leu His Met Gln Ala Leu Pro Pro
                485                 490                 495
Arg
```

<210> SEQ ID NO 23
<211> LENGTH: 6770
<212> TYPE: DNA
<213> ORGANISM: Artificial Sequence
<220> FEATURE:
<223> OTHER INFORMATION: IL13-Zeta_diihyTk-pMG

<400> SEQUENCE: 23

```
caccctagag ccgccaccat gcttctcctg gtgacaagcc ttctgctctg tgagttacca      60
cacccagcat tcctcctgat cccaggccct gtgcctccct ctacagccct caggtacctc     120
attgaggagc tggtcaacat cacccagaac cagaaggctc cgctctgcaa tggcagcatg     180
gtatggagca tcaacctgac agctggcatg tactgtgcag ccctggaatc cctgatcaac     240
gtgtcaggct gcagtgccat cgagaagacc cagaggatgc tgagcggatt ctgcccgcac     300
aaggtctcag ctgggcagtt ttccagcttg catgtccgag acaccaaaat cgaggtggcc     360
cagtttgtaa aggaccctgc tttacattta aagaaacttt ttcgcgaggg acggttcaac     420
gagtccaaat atggtccccc atgcccacca tgcccagcac ctgagttcct ggggggacca     480
tcagtcttcc tgttcccccc aaaacccaag gacactctca tgatctcccg gacccctgag     540
gtcacgtgcg tggtggtgga cgtgagccag gaagaccccg aggtccagtt caactggtac     600
gtggatggcg tggaggtgca taatgccaag acaaagccgc gggaggagca gttcaacagc     660
acgtaccgtg tggtcagcgt cctcaccgtc ctgcaccagg actggctgaa cggcaaggag     720
tacaagtgca aggtctccaa caaaggcctc ccgtcctcca tcgagaaaac catctccaaa     780
gccaaagggc agccccgaga gccacaggtg tacaccctgc ccccatccca ggaggagatg     840
accaagaacc aggtcagcct gacctgcctg gtcaaaggct tctacccag cgacatcgcc     900
gtggagtggg agagcaatgg gcagccggag aacaactaca agaccacgcc tcccgtgctg     960
gactccgacg gctccttctt cctctacagc aggctaaccg tggacaagag caggtggcag    1020
gaggggaatg tcttctcatg ctccgtgatg catgaggctc tgcacaacca ctacacacag    1080
aagagcctct ccctgtccct aggtaaaatg gccctgattg tgctgggggg cgtcgccggc    1140
```

```
ctcctgcttt tcattgggct aggcatcttc ttcagagtga agttcagcag gagcgcagac    1200
gcccccgcgt accagcaggg ccagaaccag ctctataacg agctcaatct aggacgaaga    1260
gaggagtacg atgttttgga caagagacgt ggccggacc ctgagatggg gggaaagccg     1320
agaaggaaga accctcagga aggcctgtac aatgaactgc agaaagataa gatggcggag    1380
gcctacagtg agattgggat gaaaggcgag cgccggaggg gcaaggggca cgatggcctt    1440
taccagggtc tcagtacagc caccaaggac acctacgacg cccttcacat gcaggccctg    1500 cccctcgct gagcggccgg cgaaggaggc ctagatctat cgattgtaca gctagctcga    1560
catgataaga tacattgatg agtttggaca aaccacaact agaatgcagt gaaaaaaatg    1620
ctttatttgt gaaatttgtg atgctattgc tttatttgtg aaatttgtga tgctattgct    1680
ttatttgtaa ccattataag ctgcaataaa caagttaaca acaacaattg cattcatttt    1740
atgtttcagg ttcaggggga ggtgtgggag gtttttaaa gcaagtaaaa cctctacaaa     1800
tgtggtagat ccatttaaat gttagcgaag aacatgtgag caaaaggcca gcaaaaggcc    1860
aggaaccgta aaaaggccgc gttgctggcg ttttccata ggctccgccc ccctgacgag     1920
catcacaaaa atcgacgctc aagtcagagg tggcgaaacc cgacaggact ataaagatac    1980
caggcgtttc ccctggaag ctccctcgtg cgctctcctg ttccgaccct gccgcttacc     2040
ggatacctgt ccgcctttct cccttcggga agcgtggcgc tttctcaatg ctcacgctgt    2100
aggtatctca gttcggtgta ggtcgttcgc tccaagctgg gctgtgtgca cgaaccccc     2160 gttcagcccg accgctgcgc cttatccggt aactatcgtc ttgagtccaa cccggtaaga    2220
cacgacttat cgccactggc agcagccact ggtaacagga ttagcagagc gaggtatgta    2280
ggcggtgcta cagagttctt gaagtggtgg cctaactacg gctacactag aagaacagta    2340
tttggtatct gcgctctgct gaagccagtt accttcggaa aaagagttgg tagctcttga    2400
tccggcaaac aaaccaccgc tggtagcggt ggtttttttg tttgcaagca gcagattacg    2460
cgcagaaaaa aaggatctca agaagatcct ttgatctttt ctacggggtc tgacgctcag    2520
tggaacgaaa actcacgtta agggattttg gtcatggcta gttaattaag ctgcaataaa    2580
caatcattat tttcattgga tctgtgtgtt ggttttttgt gtgggcttgg gggaggggga    2640
ggccagaatg actccaagag ctacaggaag gcaggtcaga gaccccactg gacaaacagt    2700
ggctggactc tgcaccataa cacacaatca acaggggagt gagctggatc gagctagagt    2760
ccgttacata acttacggta aatggcccgc ctggctgacc gcccaacgac ccccgcccat    2820
tgacgtcaat aatgacgtat gttcccatag taacgccaat agggactttc cattgacgtc    2880
aatgggtgga gtatttacgg taaactgccc acttggcagt acatcaagtg tatcatatgc    2940
caagtacgcc ccctattgac gtcaatgacg gtaaatggcc cgcctggcat tatgcccagt    3000
acatgacctt atgggacttt cctacttggc agtacatcta cgtattagtc atcgctatta    3060
ccatggtgat gcggttttgg cagtacatca atgggcgtgg atagcggttt gactcacggg    3120
gatttccaag tctccacccc attgacgtca atgggagttt gttttggcac caaaatcaac    3180
gggactttcc aaaatgtcgt aacaactccg ccccattgac gcaaatgggc ggtaggcgtg    3240
tacggtggga ggtctatata agcagagctc gtttagtgaa ccgtcagatc gcctggagac    3300
gccatccacg ctgttttgac ctccatagaa gacaccggga ccgatccagc ctccgcggcc    3360
gggaacggtg cattggaacg cggattcccc gtgccaagag tgacgtaagt accgcctata    3420
gagtctatag gcccacctag ttgtgaccgg cgcctagtgt tgacaattaa tcatcggcat    3480
agtataatac gactcactat aggagggcca ccatgtcgac tactaacctt cttctctttc    3540
```

```
ctacagctga gatcaccggt aggagggcca tcatgaaaaa gcctgaactc accgcgacgt    3600
ctgtcgcgaa gtttctgatc gaaaagttcg acagcgtctc cgacctgatg cagctctcgg    3660
agggcgaaga atctcgtgct ttcagcttcg atgtaggagg cgtggatat gtcctgcggg     3720 taaatagctg cgccgatggt ttctacaaag atcgttatgt ttatcggcac tttgcatcgg    3780
ccgcgctccc gattccggaa gtgcttgaca ttggggaatt cagcgagagc ctgacctatt    3840
gcatctcccg ccgtgcacag ggtgtcacgt tgcaagacct gcctgaaacc gaactgcccg    3900
ctgttctgca acccgtcgcg gagctcatgg atgcgatcgc tcggccgat  cttagccaga    3960 cgagcgggtt cggcccattc ggaccgcaag gaatcggtca atacactaca tggcgtgatt    4020
tcatatgcgc gattgctgat ccccatgtgt atcactggca aactgtgatg gacgacaccg    4080
tcagtgcgtc cgtcgcgcag gctctcgatg agctgatgct ttgggccgag gactgccccg    4140
aagtccggca cctcgtgcac gcggatttcg gctccaacaa tgtcctgacg gacaatggcc    4200
gcataacagc ggtcattgac tggagcgagg cgatgttcgg ggattcccaa tacgaggtcg    4260
ccaacatctt cttctggagg ccgtggttgg cttgtatgga gcagcagacg cgctacttcg    4320
agcggaggca tccggagctt gcaggatcgc cgcggctccg ggcgtatatg ctccgcattg    4380
gtcttgacca actctatcag agcttggttg acggcaattt cgatgatgca gcttgggcgc    4440
agggtcgatg cgacgcaatc gtccgatccg gagcccggac tgtcgggcgt acacaaatcg    4500
cccgcagaag cgcggccgtc tggaccgatg gctgtgtaga agtcgcgtct gcgttcgacc    4560
aggctgcgcg ttctcgcggc catagcaacc gacgtacggc gttgcgccct cgccggcagc    4620
aagaagccac ggaagtccgc ccggagcaga aaatgcccac gctactgcgg gtttatatag    4680 acggtccccca cgggatgggg aaaaccacca ccacgcaact gctggtggcc ctgggttcgc    4740
gcgacgatat cgtctacgta cccgagccga tgacttactg gcgggtgctg ggggcttccg    4800
agacaatcgc gaacatctac accacacaac accgcctcga ccaggtgag  atatcggccg    4860 gggacgcggc ggtggtaatg acaagcgccc agataacaat gggcatgcct tatgccgtga    4920
ccgacgccgt tctggctcct catatcgggg gggaggctgg gagctcacat gccccgcccc    4980
cggccctcac cctcatcttc gaccgccatc ccatcgccgc cctcctgtgc tacccggccg    5040
cgcggtacct tatgggcagc atgacccccc aggccgtgct ggcgttcgtg gccctcatcc    5100
cgccgacctt gccgggcacc aacatcgtgc ttggggccct tccggaggac agacacatcg    5160
accgcctggc caaacgccag cgccccgcg agcggctgga cctggctatg ctggctgcga    5220
ttcgccgcgt ttacgggcta cttgccaata cggtgcggta tctgcagtgc ggcgggtcgt    5280
ggcgggagga ctggggacag cttttcggga cggccgtgcc gccccagggt gccgagcccc    5340
agagcaacgc gggcccacga ccccatatcg gggacacgtt atttaccctg tttcgggccc    5400
ccgagttgct ggcccccaac ggcgacctgt ataacgtgtt tgcctgggcc ttggacgtct    5460
tggccaaacg cctccgttcc atgcacgtct ttatcctgga ttacgaccaa tcgcccgccg    5520
gctgccggga cgccctgctg caacttacct ccgggatggt ccagaccccac gtcaccaccc    5580 ccggctccat accgacgata tgcgacctgg cgcgcacgtt tgcccgggag atggggagg     5640 ctaactgagt cgagaattcg ctagagggcc ctattctata gtgtcaccta aatgctagag    5700
ctcgctgatc agcctcgact gtgccttcta gttgccagcc atctgttgtt tgcccctccc    5760
ccgtgccttc cttgaccctg gaaggtgcca ctcccactgt cctttcctaa taaaatgagg    5820
aaattgcatc gcattgtctg agtaggtgtc attctattct ggggggtggg gtggggcagg    5880
acagcaaggg ggaggattgg gaagacaata gcaggcatgc gcagggccca attgctcgag    5940
```

```
cggccgcaat aaaatatctt tattttcatt acatctgtgt gttggttttt tgtgtgaatc    6000
gtaactaaca tacgctctcc atcaaaacaa aacgaaacaa aacaaactag caaaataggc    6060
tgtccccagt gcaagtgcag gtgccagaac atttctctat cgaaggatct gcgatcgctc    6120
cggtgcccgt cagtgggcag agcgcacatc gcccacagtc cccgagaagt tggggggagg    6180
ggtcggcaat tgaaccggtg cctagagaag gtggcgcggg gtaaactggg aaagtgatgt    6240
cgtgtactgg ctccgccttt ttcccgaggg tgggggagaa ccgtatataa gtgcagtagt    6300
cgccgtgaac gttctttttc gcaacgggtt tgccgccaga acacagctga agcttcgagg    6360
ggctcgcatc tctccttcac gcgcccgccg ccctacctga ggccgccatc cacgccggtt    6420
gagtcgcgtt ctgccgcctc ccgcctgtgg tgcctcctga actgcgtccg ccgtctaggt    6480
aagtttaaag ctcaggtcga gaccgggcct ttgtccggcg ctcccttgga gcctacctag    6540
actcagccgg ctctccacgc tttgcctgac cctgcttgct caactctacg tctttgtttc    6600
gttttctgtt ctgcgccgtt acagatccaa gctgtgaccg gcgcctacgt aagtgatatc    6660
tactagattt atcaaaaaga gtgttgactt gtgagcgctc acaattgata cggattcatc    6720
gagagggaca cgtcgactac taaccttctt ctctttccta cagctgagat              6770

<210> SEQ ID NO 24
<211> LENGTH: 6785
<212> TYPE: DNA
<213> ORGANISM: Artificial Sequence
<220> FEATURE:
<223> OTHER INFORMATION: plasmid DNA vector incorporating human, simian
      virus 40, E. coli, cytomegalovirus and bovine sequences

<400> SEQUENCE: 24
tcgaaggatc tgcgatcgct ccggtgcccg tcagtgggca gagcgcacat cgcccacagt      60
ccccgagaag ttgggggagg ggtcggcaat tgaaccggt gcctagagaa ggtggcgcgg     120
ggtaaactgg gaaagtgatg tcgtgtactg gctccgcctt tttcccgagg gtgggggaga     180
accgtatata agtgcagtag tcgccgtgaa cgttcttttt cgcaacgggt ttgccgccag     240
aacacagctg aagcttcgag gggctcgcat ctctccttca cgcgcccgcc gcctacctg     300 aggccgccat ccacgccggt tgagtcgcgt tctgccgcct cccgcctgtg gtgcctcctg     360
aactgcgtcc gccgtctagg taagtttaaa gctcaggtcg agaccgggcc tttgtccggc     420
gctcccttgg agcctaccta gactcagccg gctctccacg ctttgcctga ccctgcttgc     480
tcaactctac gtctttgttt cgttttctgt tctgcgccgt tacagatcca agctgtgacc     540
ggcgcctacg taagtgatat ctactagatt tatcaaaaag agtgttgact tgtgagcgct     600
cacaattgat acttagattc atcgagaggg acacgtcgac tactaacctt cttctctttc     660
ctacagctga gatcacccta gagccgccac catgcttctc ctggtgacaa gccttctgct     720
ctgtgagtta ccacacccag cattcctcct gatcccaggc cctgtgcctc cctctacagc     780
cctcaggtac ctcattgagg agctggtcaa catcacccag aaccagaagg ctccgctctg     840
caatggcagc atggtatgga gcatcaacct gacagctggc atgtactgtg cagccctgga     900
atccctgatc aacgtgtcag gctgcagtgc catcgagaag acccagagga tgctgagcgg     960
attctgcccg cacaaggtct cagctgggca gttttccagc ttgcatgtcc agacaccaa    1020 aatcgaggtg gcccagtttg taaaggacct gctcttacat ttaaagaaac ttttcgcga    1080 gggacggttc aacgagtcca atatggtcc cccatgccca ccatgccag cacctgagtt    1140 cctgggggga ccatcagtct tcctgttccc cccaaaaccc aaggacactc tcatgatctc    1200
```

```
ccggacccct gaggtcacgt gcgtggtggt ggacgtgagc caggaagacc ccgaggtcca    1260
gttcaactgg tacgtggatg gcgtggaggt gcataatgcc aagacaaagc cgcgggagga    1320
gcagttcaac agcacgtacc gtgtggtcag cgtcctcacc gtcctgcacc aggactggct    1380
gaacggcaag gagtacaagt gcaaggtctc caacaaaggc ctcccgtcct ccatcgagaa    1440
aaccatctcc aaagccaaag gcagccccg agagccacag gtgtacaccc tgccccatc    1500 ccaggaggag atgaccaaga accaggtcag cctgacctgc ctggtcaaag gcttctaccc    1560
cagcgacatc gccgtggagt gggagagcaa tgggcagccg gagaacaact acaagaccac    1620
gcctcccgtg ctggactccg acggctcctt cttcctctac agcaggctaa ccgtggacaa    1680
gagcaggtgg caggagggga atgtcttctc atgctccgtg atgcatgagg ctctgcacaa    1740
ccactacaca cagaagagcc tctccctgtc cctaggtaaa atggccctga ttgtgctggg    1800
gggcgtcgcc ggcctcctgc ttttcattgg gctaggcatc ttcttcagag tgaagttcag    1860
caggagcgca gacgccccg cgtaccagca gggccagaac cagctctata cgagctcaa    1920 tctaggacga agagaggagt acgatgtttt ggacaagaga cgtggccggg accctgagat    1980 gggggggaaag ccgagaagga agaaccctca ggaaggcctg tacaatgaac tgcagaaaga    2040
taagatggcg gaggcctaca gtgagattgg gatgaaaggc gagcgccgga ggggcaaggg    2100
gcacgatggc ctttaccagg gtctcagtac agccaccaag gacacctacg acgcccttca    2160
catgcaggcc ctgccccctc gctgagcggc cggcgaagga ggcctagatc tatcgattgt    2220
acagctagct cgacatgata agatacattg atgagtttgg acaaaccaca actagaatgc    2280
agtgaaaaaa atgctttatt tgtgaaattt gtgatgctat tgctttattt gtgaaatttg    2340
tgatgctatt gctttatttg taaccattat aagctgcaat aaacaagtta acaacaacaa    2400
ttgcattcat tttatgtttc aggttcaggg ggaggtgtgg gaggttttt aaagcaagta    2460 aaacctctac aaatgtggta gatccattta aatgttagcg aagaacatgt gagcaaaagg    2520
ccagcaaaag gccaggaacc gtaaaaaggc cgcgttgctg gcgttttcc ataggctccg    2580 ccccctgac gagcatcaca aaaatcgacg ctcaagtcag aggtggcgaa acccgacagg    2640
actataaaga taccaggcgt ttccccctgg aagctccctc gtgcgctctc ctgttccgac    2700
cctgccgctt accggatacc tgtccgcctt tctcccttcg ggaagcgtgg cgctttctca    2760
atgctcacgc tgtaggtatc tcagttcggt gtaggtcgtt cgctccaagc tgggctgtgt    2820
gcacgaaccc cccgttcagc ccgaccgctg cgccttatcc ggtaactatc gtcttgagtc    2880
caacccggta agacacgact tatcgccact ggcagcagcc actggtaaca ggattagcag    2940
agcgaggtat gtaggcggtg ctacagagtt cttgaagtgg tggcctaact acggctacac    3000
tagaagaaca gtatttggta tctgcgctct gctgaagcca gttaccttcg gaaaaagagt    3060
tggtagctct tgatccggca acaaaccac cgctggtagc ggtggttttt tgtttgcaa    3120 gcagcagatt acgcgcagaa aaaaaggatc tcaagaagat cctttgatct tttctacggg    3180
gtctgacgct cagtggaacg aaaactcacg ttaagggatt ttggtcatgg ctagttaatt    3240
aagctgcaat aaacaatcat tattttcatt ggatctgtgt gttggttttt tgtgtgggct    3300
tgggggaggg ggaggccaga atgactccaa gagctacagg aaggcaggtc agagacccca    3360
ctggacaaac agtggctgga ctctgcacca taacacacaa tcaacagggg agtgagctgg    3420
atcgagctag agtccgttac ataacttacg gtaaatggcc cgcctggctg accgcccaac    3480
gacccccgcc cattgacgtc aataatgacg tatgttccca tagtaacgcc aatagggact    3540
ttccattgac gtcaatgggt ggagtattta cggtaaactg cccacttggc agtacatcaa    3600
```

```
gtgtatcata tgccaagtac gcccectatt gacgtcaatg acggtaaatg gcccgcctgg    3660
cattatgccc agtacatgac cttatgggac tttcctactt ggcagtacat ctacgtatta    3720
gtcatcgcta ttaccatggt gatgcggttt tggcagtaca tcaatgggcg tggatagcgg    3780
tttgactcac ggggatttcc aagtctccac cccattgacg tcaatgggag tttgttttgg    3840
caccaaaatc aacgggactt tccaaaatgt cgtaacaact ccgccccatt gacgcaaatg    3900
ggcggtaggc gtgtacggtg ggaggtctat ataagcagag ctcgtttagt gaaccgtcag    3960
atcgcctgga gacgccatcc acgctgtttt gacctccata aagacaccg  ggaccgatcc    4020 agcctccgcg gccgggaacg gtgcattgga acgcggattc cccgtgccaa gagtgacgta    4080
agtaccgcct atagagtcta taggcccacc tagttgtgac cggcgcctag tgttgacaat    4140
taatcatcgg catagtatat cggcatagta taatacgact cactatagga gggccaccat    4200
gtcgactact aaccttcttc tctttcctac agctgagatc accggtagga gggccatcat    4260
gaaaaagcct gaactcaccg cgacgtctgt cgcgaagttt ctgatcgaaa agttcgacag    4320
cgtctccgac ctgatgcagc tctcggaggg cgaagaatct cgtgctttca gcttcgatgt    4380
aggagggcgt ggatatgtcc tgcgggtaaa tagctgcgcc gatggtttct acaaagatcg    4440
ttatgtttat cggcactttg catcggccgc gctcccgatt ccggaagtgc ttgacattgg    4500
ggaattcagc gagagcctga cctattgcat ctcccgccgt gcacagggtg tcacgttgca    4560
agacctgcct gaaaccgaac tgcccgctgt tctgcaaccc gtcgcggagc tcatggatgc    4620
gatcgctgcg gccgatctta gccagacgag cgggttcggc ccattcggac cgcaaggaat    4680
cggtcaatac actacatggc gtgatttcat atgcgcgatt gctgatcccc atgtgtatca    4740
ctggcaaact gtgatggacg acaccgtcag tgcgtccgtc gcgcaggctc tcgatgagct    4800
gatgctttgg gccgaggact gccccgaagt ccggcacctc gtgcacgcgg atttcggctc    4860
caacaatgtc ctgacggaca atggccgcat aacagcggtc attgactgga gcgaggcgat    4920
gttcggggat tcccaatacg aggtcgccaa catcttcttc tggaggccgt ggttggcttg    4980
tatggagcag cagacgcgct acttcgagcg gaggcatccg gagcttgcag atcgccgcg    5040 gctccgggcg tatatgctcc gcattggtct tgaccaactc tatcagagct tggttgacgg    5100
caatttcgat gatgcagctt gggcgcaggg tcgatgcgac gcaatcgtcc gatccggagc    5160
cgggactgtc gggcgtacac aaatcgcccg cagaagcgcg gccgtctgga ccgatgcctg    5220
tgtagaagtc gcgtctgcgt tcgaccaggc tgcgcgttct cgcggccata gcaaccgacg    5280
tacgcgcttg cgccctcgcc ggcagcaaga agccacggaa gtccgcccgg agcagaaaat    5340
gcccacgcta ctgcgggttt atatagacgg tccccacggg atggggaaaa ccaccaccac    5400
gcaactgctg gtgccctgg gttcgcgcga cgatatcgtc tacgtacccg agccgatgac    5460
ttactggcgg gtgctggggg cttccgagac aatcgcgaac atctacacca cacaacaccg    5520
cctcgaccag ggtgagatat cggccgggga cgcggcggtg gtaatgacaa cgcccagat    5580 aacaatgggc atgccttatg ccgtgaccga cgccgttctg gctcctcata tcggggggga    5640
ggctgggagc tcacatgccc cgcccccggc cctcaccctc atcttcgacc gccatcccat    5700
cgccgccctc ctgtgctacc cggccgcgcg gtaccttatg gcagcatga  cccccaggc    5760 cgtgctggcg ttcgtggccc tcatcccgcc gaccttgccc ggcaccaaca tcgtgcttgg    5820
ggcccttccg gaggacagac acatcgaccg cctggccaaa cgccagcgcc ccggcgagcg    5880
gctggacctg gctatgctgg ctgcgattcg ccgcgtttac gggctacttg ccaatacggt    5940
gcggtatctg cagtgcggcg ggtcgtggcg ggaggactgg ggacagcttt cggggacggc    6000
```

```
cgtgccgccc cagggtgccg agccccagag caacgcgggc ccacgacccc atatcgggga    6060
cacgttattt accctgtttc ggggccccga gttgctggcc cccaacggcg acctgtataa    6120
cgtgtttgcc tgggccttgg acgtcttggc caaacgcctc cgttccatgc acgtctttat    6180
cctggattac gaccaatcgc ccgccggctg ccgggacgcc ctgctgcaac ttacctccgg    6240
gatggtccag acccacgtca ccaccccgg ctccataccg acgatatgcg acctggcgcg    6300
cacgtttgcc cggagatgg gggaggctaa ctgagtcgag aattcgctag agggccctat    6360
tctatagtgt cacctaaatg ctagagctcg ctgatcagcc tcgactgtgc cttctagttg    6420
ccagccatct gttgtttgcc cctcccccgt gccttccttg accctggaag gtgccactcc    6480
cactgtcctt tcctaataaa atgaggaaat tgcatcgcat tgtctgagta ggtgtcattc    6540
tattctgggg gtggggtgg ggcaggacag caagggggag gattgggaag acaatagcag    6600
gcatgcgcag ggcccaattg ctcgagcggc cgcaataaaa tatctttatt ttcattacat    6660
ctgtgtgttg gttttttgtg tgaatcgtaa ctaacatacg ctctccatca aaacaaaacg    6720
aaacaaaaca aactagcaaa ataggctgtc cccagtgcaa gtgcaggtgc cagaacattt    6780
ctcta                                                                6785

<210> SEQ ID NO 25
<211> LENGTH: 6785
<212> TYPE: DNA
<213> ORGANISM: Artificial Sequence
<220> FEATURE:
<223> OTHER INFORMATION: plasmid DNA vector incorporating human, simian
      virus 40, E. coli, cytomegalovirus and bovine sequences

<400> SEQUENCE: 25
tagagaaatg ttctggcacc tgcacttgca ctggggacag cctatttgc tagtttgttt        60 tgtttcgttt tgttttgatg gagagcgtat gttagttacg attcacacaa aaaccaaca      120 cacagatgta atgaaaataa agatatttta ttgcggccgc tcgagcaatt gggcccctgcg    180 catgcctgct attgtcttcc caatcctccc ccttgctgtc ctgccccacc cacccccca     240 gaatagaatg acacctactc agacaatgcg atgcaatttc ctcattttat taggaaagga    300
cagtgggagt ggcaccttcc agggtcaagg aaggcacggg ggaggggcaa acaacagatg    360
gctggcaact agaaggcaca gtcgaggctg atcagcgagc tctagcattt aggtgacact    420
atagaatagg gccctctagc gaattctcga ctcagttagc ctccccatc tcccgggcaa    480 acgtgcgcgc caggtcgcat atcgtcggta tggagccggg ggtggtgacg tgggtctgga    540
ccatcccgga ggtaagttgc agcagggcgt cccggcagcc ggcgggcgat tggtcgtaat    600
ccaggataaa gacgtgcatg gaacggaggc gtttggccaa gacgtccaag gcccaggcaa    660
acacgttata caggtcgccg ttgggggcca gcaactcggg ggcccgaaac agggtaaata    720
acgtgtcccc gatatggggt cgtgggcccg cgttgctctg ggctcggca ccctggggcg    780 gcacggccgt ccccgaaagc tgtccccagt cctcccgcca cgacccgccg cactgcagat    840
accgcaccgt attggcaagt agcccgtaaa cgcggcgaat cgcagccagc atagccaggt    900
ccagccgctc gccgggggcg ctggcgttgg ccaggcggtc gatgtgtctg tcctccggaa    960
gggccccaag cacgatgttg gtgccgggca aggtcggcgg gatgagggcc acgaacgcca    1020
gcacggcctg gggggtcatg ctgcccataa ggtaccgcgc ggccgggtag cacaggaggg    1080
cggcgatggg atggcggtcg aagatgaggg tgagggccgg ggcgggca tgtgagctcc    1140 cagcctcccc cccgatatga ggagccagaa cggcgtcggt cacggcataa ggcatgccca    1200
ttgttatctg ggcgcttgtc attaccaccg ccgcgtcccc ggccgatatc tcaccctggt    1260
```

```
cgaggcggtg ttgtgtggtg tagatgttcg cgattgtctc ggaagccccc agcacccgcc   1320
agtaagtcat cggctcgggt acgtagacga tatcgtcgcg cgaacccagg gccaccagca   1380
gttgcgtggt ggtggttttc cccatcccgt ggggaccgtc tatataaacc cgcagtagcg   1440
tgggcatttt ctgctccggg cggacttccg tggcttcttg ctgccggcga gggcgcaacg   1500
ccgtacgtcg gttgctatgg ccgcgagaac gcgcagcctg gtcgaacgca gacgcgactt   1560
ctacacagcc atcggtccag acggccgcgc ttctgcgggc gatttgtgta cgcccgacag   1620
tcccggctcc ggatcggacg attgcgtcgc atcgaccctg cgcccaagct gcatcatcga   1680
aattgccgtc aaccaagctc tgatagagtt ggtcaagacc aatgcggagc atatacgccc   1740
ggagccgcgg cgatcctgca agctccggat gcctccgctc gaagtagcgc gtctgctgct   1800
ccatacaagc caaccacggc ctccagaaga agatgttggc gacctcgtat tgggaatccc   1860
cgaacatcgc ctcgctccag tcaatgaccg ctgttatgcg gccattgtcc gtcaggacat   1920
tgttggagcc gaaatccgcg tgcacgaggt gccggacttc ggggcagtcc tcggcccaaa   1980
gcatcagctc atcgagagcc tgcgcgacgg acgcactgac ggtgtcgtcc atcacagttt   2040
gccagtgata cacatgggga tcagcaatcg cgcatatgaa atcacgccat gtagtgtatt   2100
gaccgattcc ttgcggtccg aatgggccga acccgctcgt ctggctaaga tcggccgcag   2160
cgatcgcatc catgagctcc gcgacgggtt gcagaacagc gggcagttcg gtttcaggca   2220
ggtcttgcaa cgtgacaccc tgtgcacggc gggagatgca ataggtcagg ctctcgctga   2280
attccccaat gtcaagcact tccggaatcg ggagcgcggc cgatgcaaag tgccgataaa   2340
cataacgatc tttgtagaaa ccatcggcgc agctatttac ccgcaggaca tatccacgcc   2400
ctcctacatc gaagctgaaa gcacgagatt cttcgccctc cgagagctgc atcaggtcgg   2460
agacgctgtc gaacttttcg atcagaaact tcgcgacaga cgtcgcggtg agttcaggct   2520
ttttcatgat ggccctccta ccggtgatct cagctgtagg aaagagaaga aggttagtag   2580
tcgacatggt ggccctccta tagtgagtcg tattatacta tgccgatata ctatgccgat   2640
gattaattgt caacactagg cgccggtcac aactaggtgg gcctatagac tctataggcg   2700
gtacttacgt cactcttggc acggggaatc cgcgttccaa tgcaccgttc ccggccgcgg   2760
aggctggatc ggtcccggtg tcttctatgg aggtcaaaac agcgtggatg gcgtctccag   2820
gcgatctgac ggttcactaa acgagctctg cttatataga cctcccaccg tacacgccta   2880
ccgcccattt gcgtcaatgg ggcggagttg ttacgacatt ttggaaagtc ccgttgattt   2940
tggtgccaaa acaaactccc attgacgtca atggggtgga gacttggaaa tccccgtgag   3000
tcaaaccgct atccacgccc attgatgtac tgccaaaacc gcatcaccat ggtaatagcg   3060
atgactaata cgtagatgta ctgccaagta ggaaagtccc ataaggtcat gtactgggca   3120
taatgccagg cgggccattt accgtcattg acgtcaatag ggggcgtact tggcatatga   3180
tacacttgat gtactgccaa gtgggcagtt taccgtaaat actccaccca ttgacgtcaa   3240
tggaaagtcc ctattggcgt tactatggga acatacgtca ttattgacgt caatgggcgg   3300
gggtcgttgg gcggtcagcc aggcgggcca tttaccgtaa gttatgtaac ggactctagc   3360
tcgatccagc tcactcccct gttgattgtg tgttatggtg cagagtccag ccactgtttg   3420
tccagtgggg tctctgacct gccttcctgt agctcttgga gtcattctgg cctccccctc   3480
ccccaagccc acacaaaaaa ccaacacaca gatccaatga aaataatgat tgtttattgc   3540
agcttaatta actagccatg accaaaatcc cttaacgtga gttttcgttc cactgagcgt   3600 cagacccegt agaaaagatc aaaggatctt cttgagatcc ttttttttctg cgcgtaatct   3660
```

```
gctgcttgca aacaaaaaaa ccaccgctac cagcggtggt ttgtttgccg gatcaagagc    3720
taccaactct tttccgaag gtaactggct tcagcagagc gcagatacca aatactgttc    3780
ttctagtgta gccgtagtta ggccaccact tcaagaactc tgtagcaccg cctacatacc    3840
tcgctctgct aatcctgtta ccagtggctg ctgccagtgg cgataagtcg tgtcttaccg    3900
ggttggactc aagacgatag ttaccggata aggcgcagcg gtcgggctga acgggggtt    3960 cgtgcacaca gcccagcttg gagcgaacga cctacaccga actgagatac ctacagcgtg    4020
agcattgaga aagcgccacg cttcccgaag ggagaaaggc ggacaggtat ccggtaagcg    4080
gcagggtcgg aacaggagag cgcacgaggg agcttccagg gggaaacgcc tggtatcttt    4140
atagtcctgt cgggtttcgc cacctctgac ttgagcgtcg attttgtga tgctcgtcag    4200 gggggcggag cctatggaaa aacgccagca acgcggcctt tttacggttc ctggccttt    4260 gctggccttt tgctcacatg ttcttcgcta acatttaaat ggatctacca catttgtaga    4320
ggttttactt gctttaaaaa acctcccaca cctcccctg aacctgaaac ataaaatgaa    4380
tgcaattgtt gttgttaact tgtttattgc agcttataat ggttacaaat aaagcaatag    4440
catcacaaat ttcacaaata aagcaatagc atcacaaatt tcacaaataa agcatttttt    4500
tcactgcatt ctagttgtgg tttgtccaaa ctcatcaatg tatcttatca tgtcgagcta    4560
gctgtacaat cgatagatct aggcctcctt cgccggccgc tcagcgaggg ggcagggcct    4620
gcatgtgaag ggcgtcgtag gtgtccttgg tggctgtact gagaccctgg taaaggccat    4680 cgtgccctt gcccctccgg cgctcgcctt tcatcccaat ctcactgtag gcctccgcca    4740
tcttatcttt ctgcagttca ttgtacaggc cttcctgagg gttcttcctt ctcggctttc    4800
cccccatctc agggtcccgg ccacgtctct tgtccaaaac atcgtactcc tctcttcgtc    4860
ctagattgag ctcgttatag agctggttct ggccctgctg gtacgcgggg gcgtctgcgc    4920
tcctgctgaa cttcactctg aagaagatgc ctagcccaat gaaaagcagg aggccggcga    4980
cgccccccag cacaatcagg gccattttac ctagggacag ggagaggctc ttctgtgtgt    5040
agtggttgtg cagagcctca tgcatcacgg agcatgagaa gacattcccc tcctgccacc    5100
tgctcttgtc cacggttagc ctgctgtaga ggaagaagga gccgtcggag tccagcacgg    5160
gaggcgtggt cttgtagttg ttctccggct gcccattgct ctcccactcc acggcgatgt    5220
cgctggggta gaagcctttg accaggcagg tcaggctgac ctggttcttg gtcatctcct    5280
cctgggatgg gggcagggtg tacacctgtg gctctcgggg ctgcccttg gctttggaga    5340 tggttttctc gatggaggac gggaggcctt tgttggagac cttgcacttg tactccttgc    5400
cgttcagcca gtcctggtgc aggacggtga ggacgctgac cacacggtac gtgctgttga    5460
actgctcctc ccgcggcttt gtcttggcat tatgcacctc cacgccatcc acgtaccagt    5520
tgaactggac ctcggggtct tcctggctca cgtccaccac cacgcacgtg acctcagggg    5580
tccgggagat catgagagtg tccttgggtt ttgggggaa caggaagact gatggtcccc    5640
ccaggaactc aggtgctggg catggtgggc atggggacc atatttggac tcgttgaacc    5700
gtccctcgcg aaaagtttc tttaaatgta agagcaggtc ctttacaaac tgggccacct    5760
cgattttggt gtctcggaca tgcaagctgg aaaactgccc agctgagacc ttgtgcgggc    5820
agaatccgct cagcatcctc tgggtcttct cgatggcact gcagcctgac acgttgatca    5880
gggattccag ggctgcacag tacatgccag ctgtcaggtt gatgctccat accatgctgc    5940
cattgcagag cggagccttc tggttctggg tgatgttgac cagctcctca atgaggtacc    6000
tgagggctgt agagggaggc acagggcctg ggatcaggag gaatgctggg tgtggtaact    6060
```

```
cacagagcag aaggcttgtc accaggagaa gcatggtggc ggctctaggg tgatctcagc    6120
tgtaggaaag agaagaaggt tagtagtcga cgtgtccctc tcgatgaatc taagtatcaa    6180
ttgtgagcgc tcacaagtca acactctttt tgataaatct agtagatatc acttacgtag    6240
gcgccggtca cagcttggat ctgtaacggc gcagaacaga aaacgaaaca aagacgtaga    6300
gttgagcaag cagggtcagg caaagcgtgg agagccggct gagtctaggt aggctccaag    6360
ggagcgccgg acaaaggccc ggtctcgacc tgagctttaa acttacctag acggcggacg    6420
cagttcagga ggcaccacag gcgggaggcg gcagaacgcg actcaaccgg cgtggatggc    6480
ggcctcaggt agggcggcgg gcgcgtgaag gagagatgcg agccctcga agcttcagct     6540 gtgttctggc ggcaaacccg ttgcgaaaaa gaacgttcac ggcgactact gcacttatat    6600
acggttctcc cccaccctcg ggaaaaaggc ggagccagta cacgacatca ctttcccagt    6660 ttacccgcg  ccaccttctc taggcaccgg ttcaattgcc gacccctccc cccaacttct    6720
cggggactgt gggcgatgtg cgctctgccc actgacgggc accggagcga tcgcagatcc    6780
ttcga                                                                6785
```

CHIMERIC IMMUNORECEPTOR USEFUL IN TREATING HUMAN GLIOMAS

This application is a continuation of prior application Ser. No. 12/314,195, filed Dec. 5, 2008, which is a continuation-in-part of application serial no. U.S. Ser. No. 11/274,344, filed Nov. 16, 2005 (now U.S. Pat. No. 7,514,537), which is a continuation-in-part of application serial no. U.S. Ser. No. 10/134,645, filed Apr. 30, 2002, now abandoned, which claims the benefit of provisional application Ser. No. 60/286,981, filed Apr. 30, 2001. Application Ser. No. 12/314,195 also claims the benefit of provisional application Ser. No. 61/091,915, filed Aug. 26, 2008. The disclosures of all of the above applications are hereby incorporated by reference in their entirety.

This invention was made with government support in the form of Cancer Center Support Grant no. P30-CA33572-21 from the United States Department of Health and Human Services, National Institutes of Health. The United States government has certain rights in the invention.

TECHNICAL FIELD

The invention relates to the field of biomedicine and specifically methods useful for cancer therapy. In particular, embodiments of the invention relate to methods for specific CTL immunotherapeutic strategies for cancer including the use of genetically-modified T lymphocytes expressing chimeric immunoreceptors in the treatment of human brain tumors and other cancers.

BACKGROUND OF THE INVENTION

Primary brain tumors are the third leading contributor to cancer-related mortality in young adults, are the second leading contributor in children, and appear to be increasing in incidence both in the pediatric and geriatric population[1-4]. Gliomas are the most common type of primary brain tumors; 20,000 cases are diagnosed and 14,000 glioma-related deaths occur annually in the United States[5-8]. Gliomas are heterogeneous with respect to their malignant behavior and, in their most common and aggressive forms, anaplastic astrocytoma (AA-grade III) and glioblastoma multiforme (GBM-grade IV), are rapidly progressive and nearly uniformly lethal[9; 10]. Currently available therapeutic modalities have minimal curative potential for these high-grade tumors and often exacerbate the already severe morbidities imposed by their location in the central nervous system. Thus patients with malignant glioma are often struck in the most productive period of their lives; frequent deterioration of mental faculties and a high case:fatality ratio contribute to the unique personal and social impact of these tumors.

The cornerstones of oncologic management of malignant glioma are resection and radiation therapy[11-16]. With modern surgical and radiotherapeutic techniques the mean duration of survival has increased to 82 weeks for glioblastoma multiforme and 275 weeks for anaplastic astrocytoma, although 5-year survival rates have only increased from 3 to 6% for glioblastoma multiforme and 12.1% for anaplastic astrocytoma[6-8]. The major prognostic indicators for prolonged survival are younger age (<40 yrs) and performance status (KPS score>70)[17]. Resections of >90% of bulky tumors are usually attempted provided that vital functional anatomy is spared. When used in conjunction with post-operative radiation therapy, the impact of extent of resection on duration of survival is less clear[18; 19]. The addition of chemotherapy to resection and radiation provides only marginal survival advantage to patients with anaplastic astrocytoma or glioblastoma multiforme[20-23]. Nitrosureas alone or in combination with procarbazine and vincristine are the conventional drugs used in the community and appear to improve the 1-year and 2-year survival rates by 15% without impacting on the overall median survival[24; 25]. More aggressive regimens incorporating platinum-based drugs and topoisomerase inhibitors are under investigation[26]. The role of high-dose chemotherapy with stem cell rescue has not been substantiated to date[27-29].

Approximately 80% of recurrent tumors arise from radiographically enhancing remnants of the original incompletely resected tumor[10; 30; 31]. Provided recurrences are unifocal and amenable in their location to aggressive re-resection, this approach can extend survival duration, particularly for patients with anaplastic astrocytoma and those glioblastoma multiforme patients with a KPS>70.[10] The median survival of recurrent glioblastoma multiforme patients treated with re-resection is 36 weeks[10; 30; 31]. Radiation therapy in the form of either brachytherapy or stereotactic radiosurgery may extend the duration of survival in re-resected recurrent glioblastoma multiforme patients by only 10-12 weeks[32]. The use of chemotherapy in the setting of recurrent disease should be in the context of available clinical trials, as its efficacy in this patient population is unsubstantiated.

The continued dismal prognosis of malignant glioma has prompted the clinical investigation of novel therapeutic entities, including, but not limited to: gene therapy (TK-suicide, antisense inhibition of tumor growth factor receptors, conditionally lethal viral vectors), immunotherapy (antibody, tumor cell vaccines, immunotoxins, adoptive transfer of activated lymphocytes), and anti-angiogenesis approaches[33-40]. The multiplicity of challenges faced in the development of effective adjuvant therapies for malignant glioma include the extensive infiltrative growth of tumor cells into normal brain parenchyma, the capacity of soluble factors elaborated from these tumors to attenuate the development of immune responses, and the difficulty of establishing clinically meaningful therapeutic ratios when administering therapeutics into the central nervous system (CNS). Early clinical evaluation of novel therapeutics is clearly indicated in this patient population.

Recently, receptors for transferrin and growth factors have been the subject of experimental glioma therapeutics utilizing ligands for these receptors conjugated to toxins or radionucleotides as a delivery system[41]. The specificity of this approach relies on the unique expression or over-expression of targeted receptors on glioma cells compared to normal brain. Interestingly, some receptor complexes for interleukins utilized by the immune system are expressed by gliomas, in particular high-affinity IL-13 receptors[42-48]. Unlike the IL-13 receptor trimolecular complex utilized by the immune system, which consists of the IL-13Rα1, the IL-4Rβ, and γc, glioma cells overexpress a unique IL-13Rα2 chain capable of binding IL-13 independently of the requirement for IL-4Rβ or γc[44; 49; 50]. Like its homologue IL-4, IL-13 has pleotrophic immunoregulatory activity outside the CNS[51-53]. Both cytokines stimulate IgE production by B lymphocytes and suppress pro-inflammatory cytokine production by macrophages. The immunobiology of IL-13 within the CNS is largely unknown.

Detailed studies by Debinski et al. using autoradiography with radiolabeled IL-13 have demonstrated abundant IL-13 binding on nearly all malignant glioma tissues studied[42; 45; 46; 48]. Moreover, the binding is highly homogeneous within tumor sections and from single cell analysis[46; 48]. Scatchard analyses of IL-13 binding to human glioma cell lines reveals on average 17,000-28,000 binding sites/cell[45]. Molecular analysis using probes specific for IL-13Rα2 mRNA fail to demonstrate expression of the glioma-specific receptor by normal brain elements in all CNS anatomic locations[42; 43]. Furthermore, autoradiography with radiolabeled IL-13 failed to demonstrate detectable specific IL-13 binding in the CNS, suggesting that the shared IL13Rα1/IL-4β/γc receptor is also not expressed at detectable levels in the CNS[46]. These findings were independently verified using immunohistochemical techniques on non-pathologic brain sections with antibodies specific for IL-13Rα1 and IL-4β[54]. Thus IL-13Rα2 stands as the most specific and ubiquitously expressed cell-surface target for glioma described to date.

As a strategy to exploit the glioma-specific expression of IL-13Rα2 to the CNS, molecular constructs of the IL-13 cytokine have been described that fuse various cytotoxins (*Pseudomonas* exotoxin and *Diptheria* toxin) to its carboxyl terminal[55-58]. Internalization of these toxins upon binding to IL-13 receptors is the basis of the selective toxicity of these fusion proteins. These toxins display potent cytotoxicity towards glioma cells in vitro at picomolar concentrations[55]. Human intracranial glioma xenografts in immunodeficient mice can be eliminated by intratumor injection of the IL-13-toxin fusion protein without observed toxicities[55]. These studies support the initiation of clinical investigation utilizing IL-13-directed immunotoxins loco-regionally for malignant glioma.

However, the binding of IL-13-based cytotoxins to the broadly expressed IL-13Rα1/IL-4β/γc receptor complex has the potential of mediating untoward toxicities to normal tissues outside the CNS, and thus limits the systemic administration of these agents. IL-13 has been extensively dissected at the molecular level: structural domains of this cytokine that are important for associating with individual receptor subunits have been mapped[55; 58]. Consequently, selected amino acid substitutions in IL-13 have predictable effects on the association of this cytokine with its receptor subunits. Amino acid substitutions in IL-13's alpha helix A, in particular at amino acid 13, disrupt its ability to associate with IL-4β, thereby selectively reducing the affinity of IL-13 to the IL-13Rα1/IL-4β/γc receptor by a factor of five[55; 57; 58]. Surprisingly, binding of mutant IL-13(E13Y) to IL-13Rα2 was not only preserved but increased relative to wild-type IL-13 by 50-fold. Thus, minimally altered IL-13 analogs can simultaneously increase IL-13's specificity and affinity for glioma cells via selective binding to IL-13Rα2 relative to normal tissues bearing IL-13Rα1/IL-4β/γc receptors.

Malignant gliomas represent a clinical entity that is highly attractive for immunotherapeutic intervention since 1) most patients with resection and radiation therapy achieve a state of minimal disease burden and 2) the anatomic location of these tumors within the confines of the CNS make direct loco-regional administration of effector cells possible. At least two pathologic studies have demonstrated that the extent of perivascular lymphocytic infiltration in malignant gliomas correlates with an improved prognosis[59-61]. Animal model systems have established that glioma-specific T cells, but not lymphokine-activated killer (LAK) cells, can mediate the regression of intracerebrally implanted gliomas[62-71]. T cells, unlike LAK cells, have the capacity to infiltrate into brain parenchyma and thus can target infiltrating tumor cells that may be distant from the primary tumor. Despite these findings, there is a substantial body of evidence that gliomas actively subvert immune destruction, primarily by the elaboration of immunosuppressive cytokines (TGF-β2) and prostaglandins, which, inhibit the induction/amplification of glioma-reactive T cell responses[72-74]. These findings have prompted the evaluation of ex vivo expanded anti-glioma effector cells for adoptive therapy as a strategy to overcome tumor-mediated limitations of generating responses in vivo.

At least ten pilot studies involving the administration of ex vivo activated lymphocytes to malignant glioma resection cavities have been reported to date[75-85]. Despite the variety of effector cell types (LAK, TILs, alloreactive CTLs), their heterogeneous composition/variability of composition from patient to patient, and the often modest in vitro reactivity of these effector cells towards glioma targets, these studies, in aggregate, report an approximate 50% response rate in patients with recurrent/refractory disease with anecdotal long-term survivors. These studies support the premise that a superior clinical effect of cellular immunotherapy for glioma might be expected with homogenous highly potent effector cells.

These pilot studies also report on the safety and tolerability of direct administration of ex vivo activated lymphocytes and interleukin-2 (IL-2), a T cell growth factor, into the resection cavity of patients with malignant glioma[75; 76; 78; 82; 86-92]. Even at large individual cell doses (>$10^9$ cells/dose), as well as high cumulative cell doses (>$27\times10^9$ cells), toxicities are modest, and typically consist of grade II or less transient headache, nausea, vomiting and fever. As noted above, these studies also employed the co-administration of rhIL-2 to support the in vivo survival of transferred lymphocytes. Multiple doses given either concurrently with lymphocytes or sequentially after lymphocyte administration were tolerated at doses as high as $1.2\times10^6$ IU/dose for 12-dose courses of IL-2 delivered every 48-hours.

Based on the findings outlined above, strategies to improve the anti-tumor potency of lymphocyte effector cells used in glioma immunotherapy are under development. One approach utilizes bi-specific antibodies capable of co-localizing and activating T lymphocytes via an anti-CD3 domain with glioma targets utilizing an epidermal growth factor receptor (EGFR) binding domain[93-96]. Preliminary clinical experience with this bi-specific antibody in combination with autologous lymphocytes suggests that T cells are activated in situ in the resection cavity. Targeting infiltrating tumor cells within the brain parenchyma, however, is a potentially significant limitation of this approach. T cells might have significantly increased anti-glioma activity if they are specific for target antigens expressed by gliomas. A growing number of human genes encoding tumor antigens to which T lymphocytes are reactive have been cloned, including the SART-1 gene, which appears to be expressed by nearly 75% of high-grade gliomas[97]. Both dendritic cell-based in vitro cell culture techniques, as well as tetramer-based T cell selection technologies are making feasible the isolation of antigen-specific T cells for adoptive therapy. Since antigens like SART-1 are recognized by T cells in the context of restricting HLA alleles, antigen-specific approaches will require substantial expansion in the number of antigens and restricting HLA alleles capable of presenting these antigens to be broadly applicable to the general population of glioma patients.

Chimeric antigen receptors engineered to consist of an extracellular single chain antibody (scFvFc) fused to the intracellular signaling domain of the T cell antigen receptor complex zeta chain (scFvFc:ζ) have the ability, when expressed in T cells, to redirect antigen recognition based on the monoclonal antibody's specificity[98]. The design of scFvFc:ζ receptors with target specificities for tumor cell-surface epitopes is a conceptually attractive strategy to generate antitumor immune effector cells for adoptive therapy as it does not rely on pre-existing anti-tumor immunity. These receptors are "universal" in that they bind antigen in a MHC independent fashion, thus, one receptor construct can be used to treat a population of patients with antigen-positive tumors. Several constructs for targeting human tumors have been described in the literature including receptors with specificities for Her2/Neu, CEA, ERRB-2, CD44v6, and epitopes selectively expressed on renal cell carcinoma[98-104]. These epitopes all share the common characteristic of being cell-surface moieties accessible to scFv binding by the chimeric T cell receptor. In vitro studies have demonstrated that both CD4+ and CD8+ T cell effector functions can be triggered via these receptors. Moreover, animal models have demonstrated the capacity of adoptively transferred scFvFc:ζ expressing T cells to eradicate established tumors[105]. The function of primary human T cells expressing tumor-specific scFvFc:ζ receptors have been evaluated in vitro; these cells specifically lyse tumor targets and secrete an array of pro-inflammatory cytokines including IL-2, TNF, IFN-γ, and GM-CSF[104]. Phase I pilot adoptive therapy studies are underway utilizing autologous scFvFc:ζ-expressing T cells specific for HIV gp120 in HIV infected individuals and autologous scFvFc:ζ-expressing T cells with specificity for TAG-72 expressed on a variety of adenocarcinomas, including breast and colorectal adenocarcinoma.

Investigators at City of Hope have engineered a CD20-specific scFvFc:ζ receptor construct for the purpose of targeting CD20+ B-cell malignancy and an L1-CAM-specific chimeric immunoreceptor for targeting neuroblastoma[106]. Preclinical laboratory studies have demonstrated the feasibility of isolating and expanding from healthy individuals and lymphoma patients CD8+ CTL clones that contain a single copy of unrearranged chromosomally integrated vector DNA and express the CD20-specific scFvFc:ζ receptor[107]. To accomplish this, purified linear plasmid DNA containing the chimeric receptor sequence under the transcriptional control of the CMV immediate/early promoter and the NeoR gene under the transcriptional control of the SV40 early promoter was introduced into activated human peripheral blood mononuclear cells by exposure of cells and DNA to a brief electrical current, a procedure called electroporation. Utilizing selection, cloning, and expansion methods currently employed in FDA-approved clinical trials at the Fred Hutchinson Cancer Research Center, Seattle, Wash., gene modified CD8+ CTL clones with CD20-specific cytolytic activity have been generated from each of six healthy volunteers in 15 separate electroporation procedures. These clones when co-cultured with a panel of human CD20+ lymphoma cell lines proliferate, specifically lyse target cells, and are stimulated to produce cytokines:

SUMMARY OF THE INVENTION

The present invention relates to chimeric transmembrane immunoreceptors, named "zetakines," comprised of an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those cells expressing a receptor for which the soluble receptor ligand is specific. Zetakine chimeric immunoreceptors represent a novel extension of antibody-based immunoreceptors for redirecting the antigen specificity of T cells, with application to treatment of a variety of cancers, particularly via the autocrine/paracrine cytokine systems utilized by human malignancy.

In one preferred embodiment exploiting the tumor-restricted expression of IL-13Rα2 by malignant glioma and renal cell carcinoma as a target for cellular immunotherapy, a mutant of the IL-13 cytokine, IL-13(E13Y), having selective high-affinity binding to IL-13Rα2 has been converted into a type I transmembrane chimeric immunoreceptor capable of redirecting T cell antigen specificity to IL-13Rα2-expressing tumor cells. This embodiment of the zetakine consists of extracellular IL-13(E13Y) fused to human IgG4 Fc, transmembrane CD4, and intracellular T cell antigen receptor CD3 complex zeta chain. Analogous immunoreceptors can be created that are specific to any of a variety of cancer cell types that selectively express receptors on their cell surfaces, for which selective ligands are known or can be engineered.

Bulk lines and clones of human T cells stably transformed to express such an immunoreceptor display redirected cytolysis of the cancer cell type to which they are specific, while showing negligible toxicity towards non-target cells. Such engineered T cells are a potent and selective therapy for malignancies, including difficult to treat cancers such as glioma.

BRIEF DESCRIPTION OF THE FIGURES

FIG. 2: Results of flow cytometric analyses (FIG. 2A: mouse anti-human Fc; FIG. 2B: anti-human IL13 mAb) showing that expressed IL13zetakine chimeric immunoreceptor traffics to the cell-surface as a type I transmembrane protein.

FIG. 4: Results of chromium release assays. FIGS. 4A and 4B show that the IL13zetakine+ CTL clone acquired glioma-specific re-directed cytolytic activity.

FIG. 7: Results of growth studies.

FIGS. 12A through 12I: Nucleic acid sequence of a plasmid DNA vector (upper strand: SEQ ID NO:24; lower strand:

Figure 1:
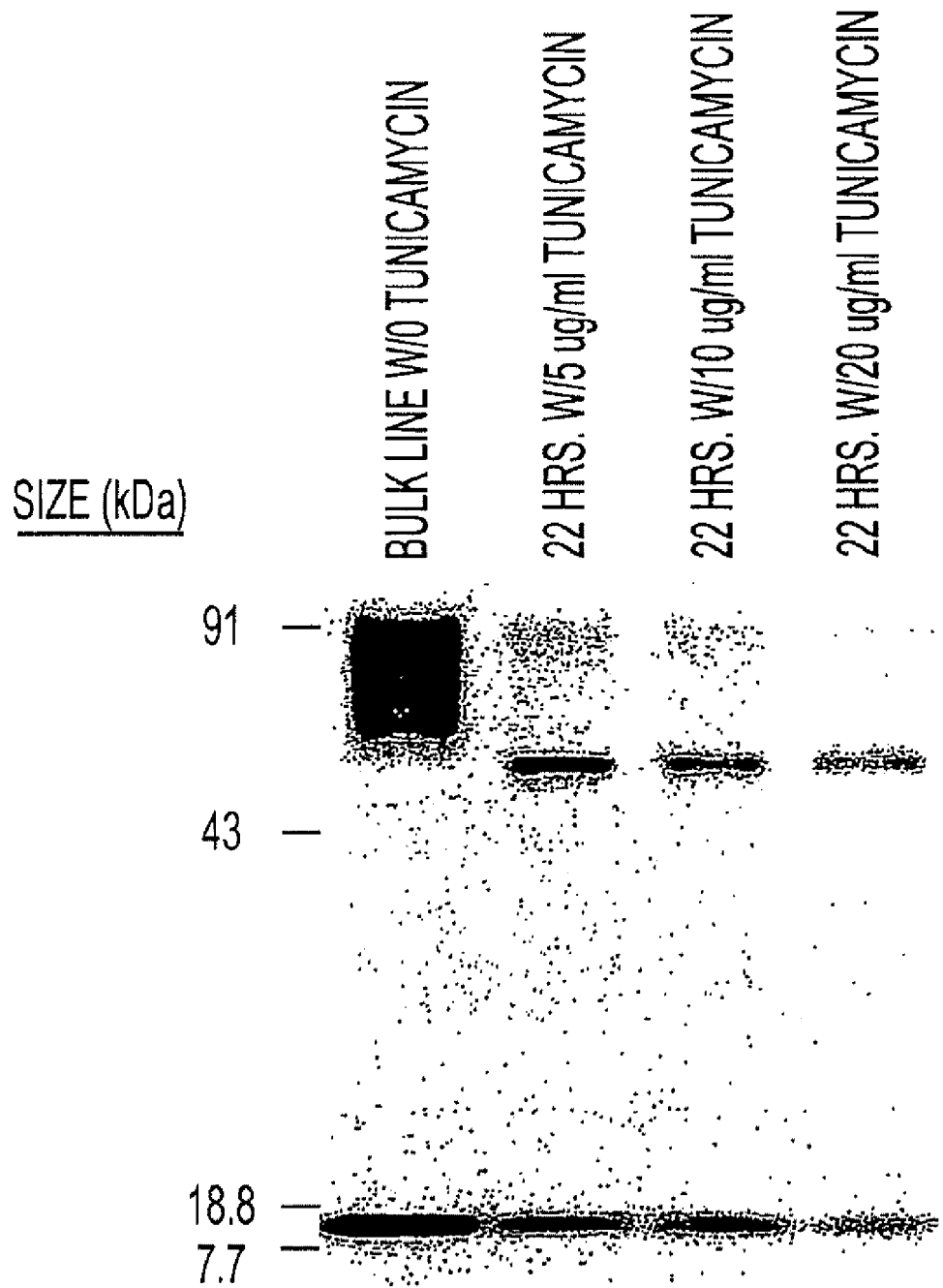
FIG. 1: Results of a Western Blot showing that the IL13zetakine Chimeric Immunoreceptor is expressed as an intact glycosylated protein in Jurkat T cells.

SEQ ID NO:25) and the corresponding amino acid sequence of IL13zetakine (SEQ ID NO:17) and HyTK (SEQ ID NO:18).

FIGS. 13A through 13I: Nucleic acid sequence of an alternate plasmid DNA vector (upper strand: SEQ ID NO:19; lower strand:SEQ ID NO:20) and the corresponding amino acid sequence of IL13zetakine (SEQ ID NO:22) and HyTK (SEQ ID NO:21).

FIGS. 14A through 14C: Nucleic acid sequence of an alternate plasmid DNA vector (SEQ ID NO:23).

FIGS. 15A through 15H: Nucleic acid sequence of an alternate plasma DNA vector (upper strand: SEQ ID NO:14; lower strand: SEQ ID NO:16) and the corresponding amino and sequence of IL13zetakine (SEQ ID NO:17) and HyTK (SEQ ID NO:18).

DETAILED DESCRIPTION

An ideal cell-surface epitope for tumor targeting with genetically-engineered re-directed T cells would be expressed solely on tumor cells in a homogeneous fashion and on all tumors within a population of patients with the same diagnosis. Modulation and/or shedding of the target molecule from the tumor cell membrane may also impact on the utility of a particular target epitope for re-directed T cell recognition. To date few "ideal" tumor-specific epitopes have been defined and secondary epitopes have been targeted based on either lack of expression on critical normal tissues or relative over-expression on tumors. In the case of malignant glioma, the intracavitary administration of T cells for the treatment of this cancer permits the expansion of target epitopes to those expressed on tumor cells but not normal CNS with less stringency on expression by other tissues outside the CNS. The concern regarding toxicity from cross-reactivity of tissues outside the CNS is mitigated by a) the sequestration of cells in the CNS based on the intracavitary route of administration and b) the low cell numbers administered in comparison to cell doses typically administered systemically.

The IL-13Rα2 receptor stands out as the most ubiquitous and specific cell-surface target for malignant glioma[47]. Sensitive autoradiographic and immunohistochemical studies fail to detect IL-13 receptors in the CNS[46; 48]. Moreover, mutation of the IL-13 cytokine to selectively bind the glioma-restricted IL-13Rα2 receptor is a further safeguard against untoward reactivity of IL-13-directed therapeutics against IL-13Rα1/IL-4β+normal tissues outside the CNS[55; 57]. The potential utility of targeting glioma IL-13Rα2 the design and testing of a novel engineered chimeric immunoreceptor for re-directing the specificity of T cells that consists of an extracellular IL-13 mutant cytokine (E13Y) tethered to the plasma membrane by human IgG4 Fc which, in turn, is fused to CD4TM and the cytoplasmic tail of CD3 zeta. This chimeric immunoreceptor has been given the designation of "IL-13 zetakine." The IL-13Rα2 receptor/IL-13(E13Y) receptor-ligand pair is an excellent guide for understanding and assessing the suitability of receptor-ligand pairs generally for use in zetakines. An ideal zetakine comprises an extracellular soluble receptor ligand having the properties of IL-13(E13Y) (specificity for a unique cancer cell surface receptor, in vivo stability due to it being derived from a naturally-occurring soluble cell signal molecule, low immunogenicity for the same reason). The use of soluble receptor ligands as distinct advantages over the prior art use of antibody fragments (such as the scFvFc immunoreceptors) or cell adhesion molecules, in that soluble receptor ligands are more likely to be stable in the extracellular environment, non-antigenic, and more selective.

Chimeric immunoreceptors according to the present invention comprise an extracellular domain comprised of a soluble receptor ligand linked to an extracellular support region that tethers the ligand to the cell surface via a transmembrane domain, in turn linked to an intracellular receptor signaling domain. Examples of suitable soluble receptor ligands include autocrine and paracrine growth factors, chemokines, cytokines, hormones, and engineered artificial small molecule ligands that exhibit the required specificity. Natural ligand sequences can also be engineered to increase their specificity for a particular target cell. Selection of a soluble receptor ligand for use in a particular zetakine is governed by the nature of the target cell, and the qualities discussed above with regard to the IL-13(E13Y) molecule, a preferred ligand for use against glioma. Examples of suitable support regions include the constant (Fc) regions of immunoglobins, human CD8α, and artificial linkers that serve to move the targeting moiety away from the cell surface for improved access to receptor binding on target cells. A preferred support region is the Fc region of an IgG (such as IgG4). Examples of suitable transmembrane domains include the transmembrane domains of the leukocyte CD markers, preferably that of CD8. Examples of intracellular receptor signaling domains are those of the T cell antigen receptor complex, preferably the zeta chain of CD3 also Fcγ RIII costimulatory signaling domains, CD28, DAP10, CD2, alone or in a series with CD3zeta.

In the IL-13 zetakine embodiment, the human IL-13 cDNA having the E13Y amino acid substitution was synthesized by PCR splice overlap extension. A full length IL-13 zetakine construct was assembled by PCR splice overlap extension and consists of the human GM-CSF receptor alpha chain leader peptide, IL-13(E13Y)-Gly-Gly-Gly, human IgG4 Fc, human CD4TM, and human cytoplasmic zeta chain. This cDNA construct was ligated into the multiple cloning site of a modified pMG plasmid under the transcriptional control of the human Elongation Factor-1 alpha promoter (Invivogen, San Diego). This expression vector co-expresses the HyTK cDNA encoding the fusion protein HyTK that combines in a single molecule hygromycin phosphotransferase activity for in vitro selection of transfectants and HSV thymidine kinase activity for in vivo ablation of cells with ganciclovir from the CMV immediate/early promoter. Western blot of whole cell Jurkat lysates pre-incubated with tunicamycin, an inhibitor of glycosylation, with an anti-zeta antibody probe demonstrated that the expected intact 56-kDa chimeric receptor protein is expressed. This receptor is heavily glycosylated consistent with post-translational modification of the native IL-13 cytokine[108]. Flow cytometric analysis of IL-13 zetakine+ Jurkat cells with anti-human IL-13 and anti-human Fc specific antibodies confirmed the cell-surface expression of the IL-13 zetakine as a type I transmembrane protein.

Using established human T cell genetic modification methods developed at City of Hope[107], primary human T cell clones expressing the IL-13 zetakine chimeric immunoreceptor have been generated for pre-clinical functional characterization. IL-13 zetakine+ CD8+ CTL clones display robust proliferative activity in ex vivo expansion cultures. Expanded clones display re-directed cytolytic activity in 4-hr chromium release assays against human IL-13Rα2+ glioblastoma cell lines. The level of cytolytic activity correlates with levels of zetakine expression on T cells and IL-13Rα2 receptor density on glioma target cells. In addition to killing, IL-13 zetakine+ clones are activated for cytokine secretion (IFN-γ, TNF-α, GM-CSF). Activation was specifically mediated by the interaction of the IL-13 zetakine with the IL-13Rα2 receptor on glioma cells since CTL clones expressing an irrelevant chimeric immunoreceptor do not respond to glioma cells, and, since activation can be inhibited in a dose-dependent manner by the addition to culture of soluble IL-13 or blocking antibodies against IL-13 on T cell transfectants and IL-13Rα2 on glioma target cells. Lastly, IL-13 zetakine-expressing CD8+ CTL clones proliferate when stimulated by glioma cells in culture. IL-13 zetakine+ CTL clones having potent anti-glioma effector activity will have significant clinical activity against malignant gliomas with limited collateral damage to normal CNS.

An immunoreceptor according to the present invention can be produced by any means known in the art, though preferably it is produced using recombinant DNA techniques. A nucleic acid sequence encoding the several regions of the chimeric receptor can prepared and assembled into a complete coding sequence by standard techniques of molecular cloning (genomic library screening, PCR, primer-assisted ligation, site-directed mutagenesis, etc.). The resulting coding region is preferably inserted into an expression vector and used to transform a suitable expression host cell line, preferably a T lymphocyte cell line, and most preferably an autologous T lymphocyte cell line. A third party derived T cell line/clone, a transformed humor or xerogenic immunologic effector cell line, for expression of the immunoreceptor. NK cells, macrophages, neutrophils, LAK cells, LIK cells, and stem cells that differentiate into these cells, can also be used. In a preferred embodiment, lymphocytes are obtained from a patient by leukopharesis, and the autologous T cells are transduced to express the zetakine and administered back to the patient by any clinically acceptable means, to achieve anti-cancer therapy.

Suitable doses for a therapeutic effect would be between about $10^6$ and about $10^9$ cells per dose, preferably in a series of dosing cycles. A preferred dosing regimen consists of four one-week dosing cycles of escalating doses, starting at about $10^7$ cells on Day 0, increasing incrementally up to a target dose of about $10^8$ cells by Day 5. Suitable modes of administration include intravenous, subcutaneous, intracavitary (for example by reservoir-access device), intraperitoneal, and direct injection into a tumor mass.

The following examples are solely for the purpose of illustrating one embodiment of the invention.

Example 1

Construction of an Immunoreceptor Coding Sequence

Figure 8A:
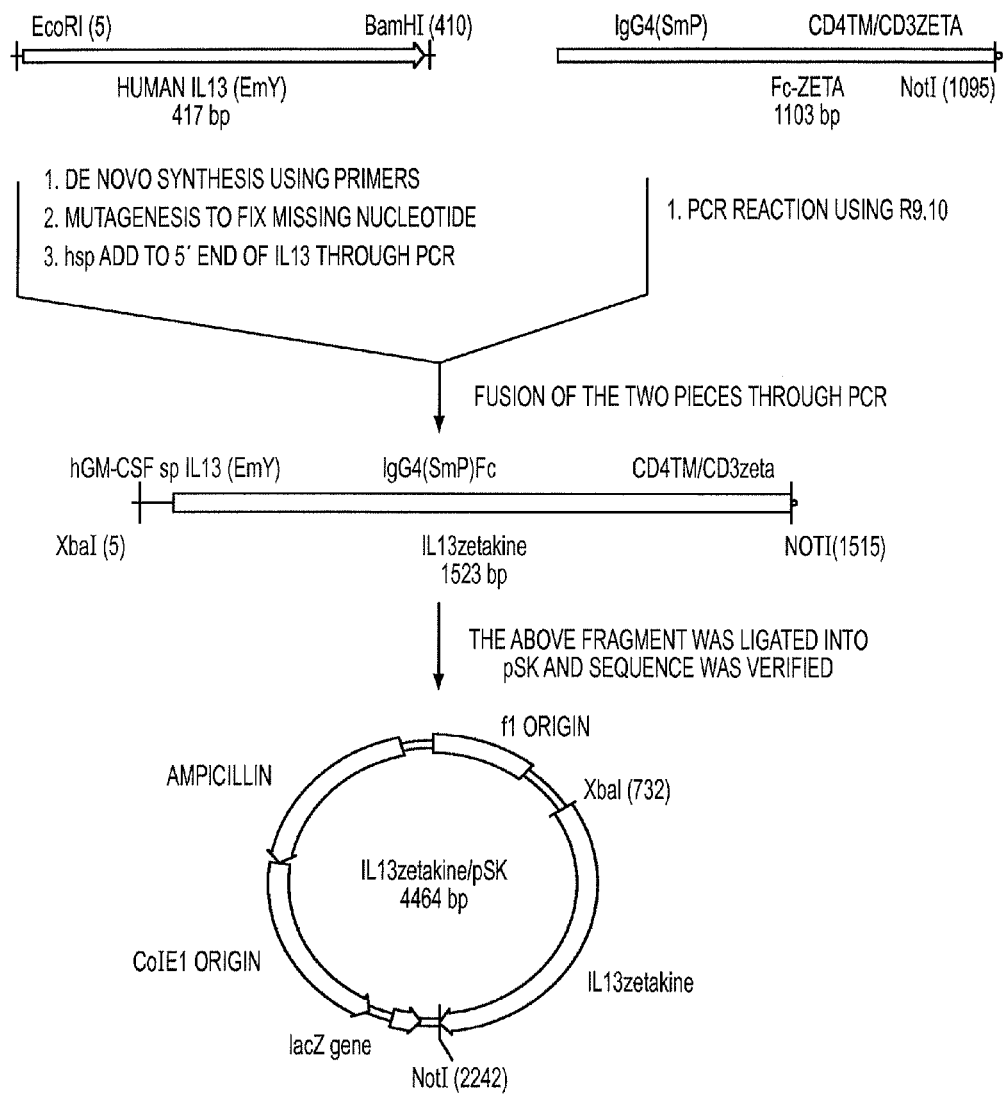
FIG. 8: Flow chart of the construction of IL13zetakine/HyTK-pMG (FIG. 8A, construction of hsp-IL13-IgG4 (SmP)-hinge-Fe-Zeta.
FIG. 8B, construction of IL13-Fc; ζ3pMBˆPac.
FIG. 8C, construction of Il13/HyTK-pMG).
Figure 8B:
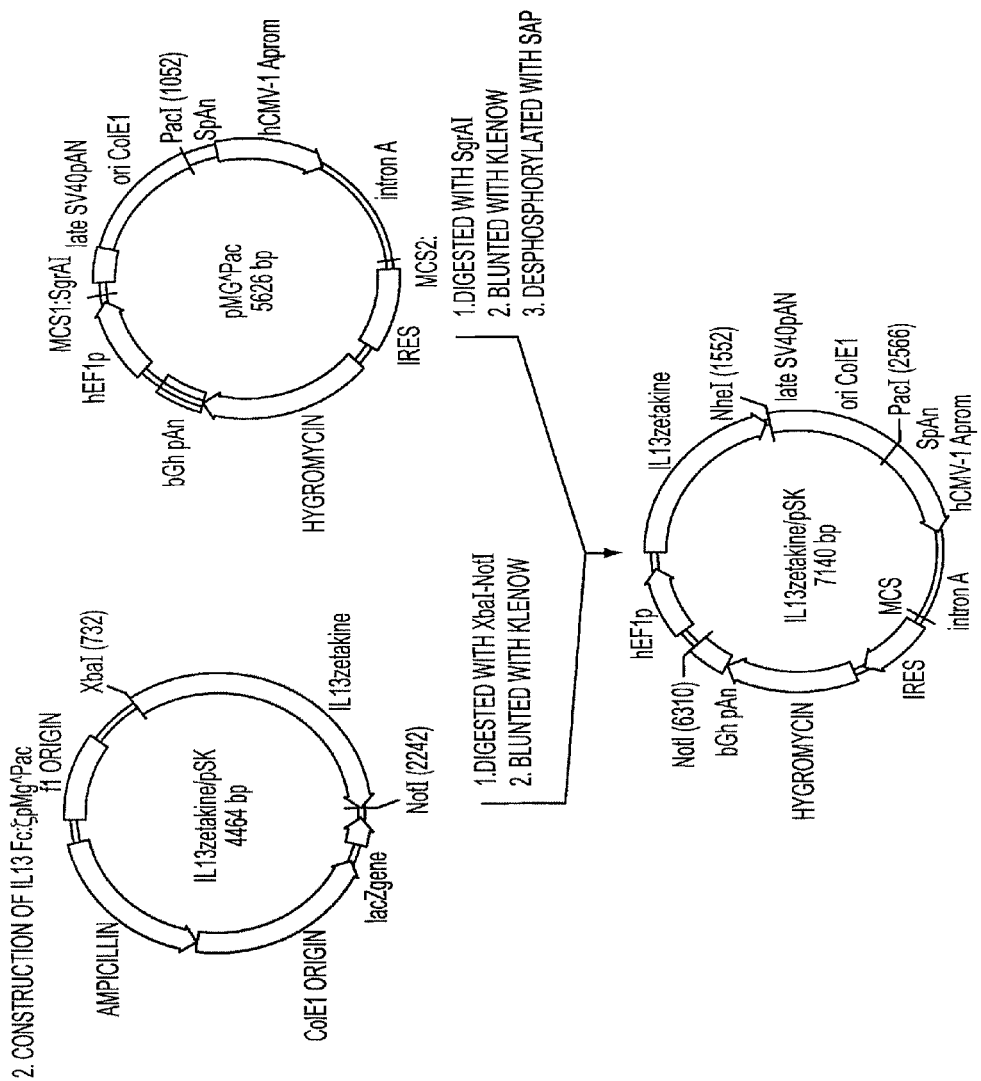
Figure 8C:
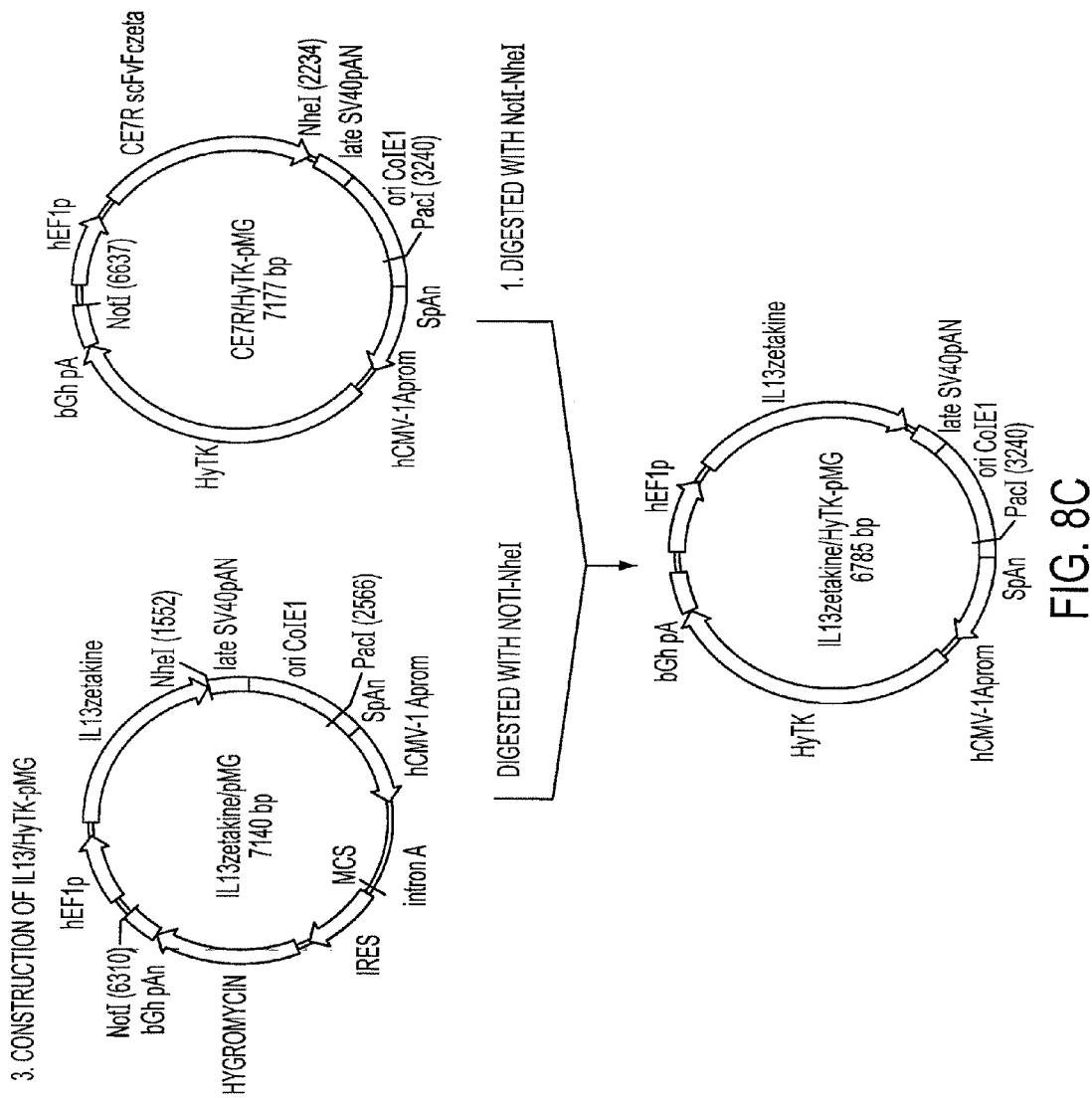

The coding sequence for an immunoreceptor according to the present invention was constructed by de novo synthesis of the IL13(E13Y) coding sequence using the following primers (see FIG. 8 for a flow chart showing the construction of the immunoreceptor coding sequence and expression vector):

IL13P1:
(SEQ ID NO. 1)
EcoRI
TATGAATTCATGGCGCTTTTGTTGACCACGGTCATTGCTCTCACTTGC
CTTGGCGGCTTTGCCTCCCCAGGCCCTGTGCCTCCCTCTACAGCCCTC
AGGTAC

IL13P2:
(SEQ ID NO. 2)
GTTGATGCTCCATACCATGCTGCCATTGCAGAGCGGAGCCTTCTGGTT
CTGGGTGATGTTGACCAGCTCCTCAATGAGGTACCTGAGGGCTGTAGA
GGGAG

IL13P3:
(SEQ ID NO. 3)
CTCTGGGTCTTCTCGATGGCACTGCAGCCTGACACGTTGATCAGGGAT
TCCAGGGCTGCACAGTACATGCCAGCTGTCAGGTTGATGCTCCATACC
ATGC

IL13P4:
(SEQ ID NO. 4)
CCTCGATTTTGGTGTCTCGGACATGCAAGCTGGAAAACTGCCCAGCTG
AGACCTTGTGCGGGCAGAATCCGCTCAGCATCCTCTGGGTCTTCTCGA
TGGC

IL13P5:
(SEQ ID NO. 5)
BamHI
TCGGATCCTCAGTTGAACCGTCCCTCGCGAAAAAGTTTCTTTAAATGT
AAGAGCAGGTCCTTTACAAACTGGGCCACCTCGATTTTGGTGTCTCGG

The final sequence (417 bp) was end-digested with EcoRI-BamHI, and ligated into the plasmid pSK (stratagene, LaJolla, Calif.) as ligation 312#3. Ligation 312#3 was mutagenized (stratagene kit, per manufacturer's instructions) to fix a deleted nucleotide using the primers 5': IL13 312#3 mut5-3 (CAACCTGACAGCTGGCATGTACTGTG-CAGCCCTGGAATC (SEQ ID NO. 6)) and 3':IL13 312#3 mut3-5 (GATTCCAGGGCTGCACAGTACATGC-CAGCTGTCAGGTTG (SEQ ID NO. 7)), and ligation 312#3 as a template, to form ligation 348#1 (IL13zetakine/pSK).

The coding Human GM-CSFR alpha chain Signal Peptide (hsp) coding sequence was fused to the 5' end of IL13(E13Y) by standard PCR splice overlap extension. The hsp sequence (101 bp) was obtained from the template ligation 301#10 (hsp/pSK) (human GCSF receptor α-chain leader sequence from human T cell cDNA), using the primers 5':19hsp5' (ATCTCTAGAGCCGCCACCATGCTTCTC-CTGGTGACAAGCCTTC (SEQ ID NO. 8)) (XbaI site highlighted in bold), and 3': hsp-IL13FR (GAGGGAGGCA-CAGGGCCTGGGATCAGGAGGAATG (SEQ ID NO. 9)). The IL-13 sequence (371 bp) was obtained using the primers 5': hsp-IL13FF (CATTCCTCCTGATCCCAGGCCCTGT-GCCTCCCTC (SEQ ID NO. 10)) and 3': IL13-IgG4FR (GG-GACCATATTTGGACTCGTTGAACCGTCCCTCGC (SEQ ID NO. 11)), and ligation 312#3 as template. Fusion was achieved using the 101 bp hsp sequence and 371 bp IL13 sequence thus obtained, and the primers 5': 19hsp5' and 3': IL13-IgG4FR, to yield a 438 bp fusion hsp-IL13 sequence.

A sequence encoding the IgG4 Fc region IgG4m:zeta was fused to the 3' end of the hsp-IL13fusion sequence using the same methods. The IgG4m:zeta sequence (1119bp) was obtained using the primers 5': IL13-IgG4FF (GCGAGG-GACGGTTCAACGAGTCCAAATATGGTCCC (SEQ ID NO. 12)) and 3': ZetaN3' (ATGCGGCCGCTCAGC-GAGGGGGCAGG (SEQ ID NO. 13)) (NotI site highlighted in bold), using the sequence R9.10 (IgG4mZeta/pSK) as template. The 1119 bp IgG4m:zeta sequence was fused to the hsp-IL13 fusion sequence using the respective sequences as templates, and the primers 5': 19hsp5' and 3': ZetaN3', to yeild a 1522 bp hsp-IL13-IgG4m:zeta fusion sequence. The ends were digested with XbaI-NotI, and ligated into pSK as ligation 351#7, to create the plasmid IL13zetakine/pSK (4464 bp).

Example 2

Construction of Expression Vector

Figure 9:
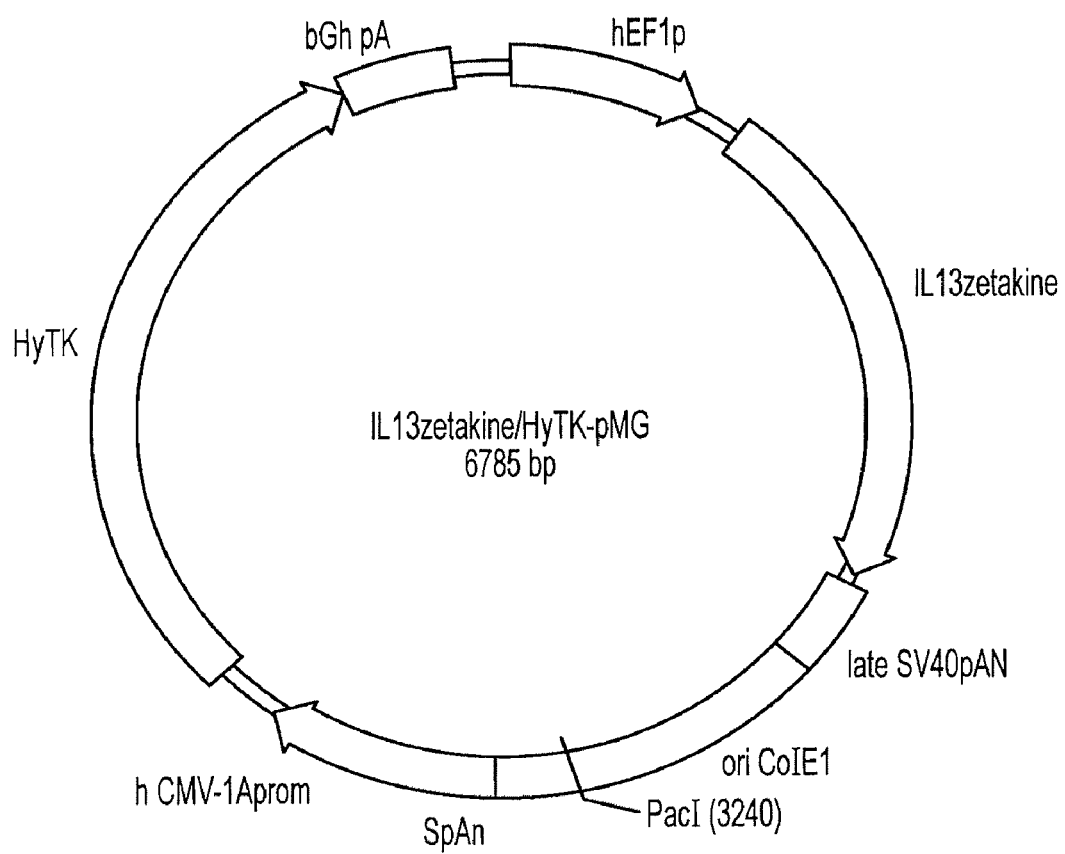
FIG. 9: Plasmid map of IL13zetakine/HyTK-pMG.
Figure 11:
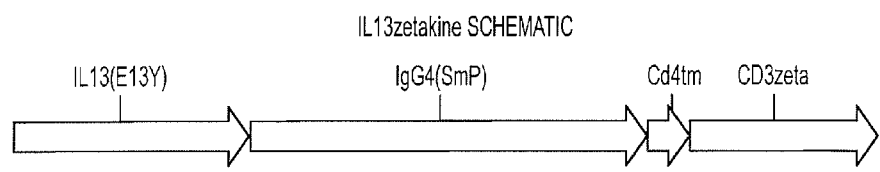
FIG. 11: Schematic diagram showing structure of IL13 zetakine insert.

An expression vector containing the IL13 zetakine coding sequence was created by digesting the IL13zetakine/pSK of Example 1 with XbaI-NotI, and creating blunt ends with Klenow, and ligating the resulting fragment into the plasmid pMG^Pac (Invirogen) (first prepared by opening with SgrAl, blunting with Klenow, and dephosphorylation with SAP), to yield the plasmid IL13zetakine/pMG. See FIG. 8. The hygromycin resistance region of IL13zetakine/pMG was removed by digestion with NotI-NheI, and replaced by the selection/suicide fusion HyTK, obtained from plasmid CE7R/HyTK-pMG (Jensen, City of Hope) by digestion with NotI-NheI, to create the expression vector IL13zetakine/HyTK-pMG (6785 bp). This plasmid comprises the Human Elongation Factor-1α promoter (hEF1p) at bases 6-549, the IL13zetakine coding sequence at bases 692-2185, the Simian Virus 40 Late polyadenylation signal (Late SV40pAN) at bases 2232-2500, a minimal *E. coli* origin of replication (Ori ColE1) at bases 2501-3247, a synthetic polyA and Pause site (SpAN) at bases 3248-3434, the Immediate early CMV enhancer/promoter (h CMV-1Aprom) at bases 3455-4077, the Hygromycin resistance-Thymidine kinase coding region fusion (HyTK) at bases 4259-6334, and the bovine growth hormone polyadenylation signal and a transcription pause (BGh pAn) at bases 6335-6633. The plasmid has a PacI linearization site at bases 3235-3242. The hEF1p and IL13zetakine elements derived from IL13zetakine/pMG, and the remaining elements derived from CE7R/HyTk-pMG (and with the exception of the HyTK element, ultimately from the parent plasmid pMG^Pac). In sum, IL13zetakine/HyTK-pMG is a modified pMG backbone, expressing the IL13zetakine gene from the hEF1 promoter, and the HyTK fusion from the h CMV-1A promoter. A map of the plasmid IL13zetakine/HyTK-pMG appears in FIG. 9. The full nucleic acid sequence of the plasmid is shown in FIG. 12. The sequence of an IL13zetakine insert is given as SEQ ID NO:15, below. See also FIG. 11.

```
                                            (SEQ ID NO: 15)
atgcttctcctggtgacaagccttctgctctgtgagttaccacaccca gcattcctcctgatcccaggccctgtgcctccctctacagccctcagg tacctcattgaggagctggtcaacatcacccagaaccagaaggctccg ctctgcaatggcagcatggtatggagcatcaacctgacagctggcatg tactgtcagccctggaatccctgatcaacgtgtcaggctgcagtgcc atcgagaagacccagaggatgctgagcggattctgcccgcacaaggtc tcagctgggcagttttccagcttgcatgtccgagacaccaaaatcgag gtggcccagtttgtaaaggacctgctcttacatttaaagaaactttt cgcgagggacggttcaacgagtccaaatatggtcccccatgcccacca tgcccagcacctgagttcctgggggaccatcagtcttcctgttcccc ccaaaacccaaggacactctcatgatctcccggaccctgaggtcacg tgcgtggtggtggacgtgagccaggaagacccgaggtccagttcaac tggtacgtggatggcgtggaggtgcataatgccaagacaaagccgcgg gaggagcagttcaacagcacgtaccgtgtggtcagcgtcctcaccgtc ctgcaccaggactggctgaacggcaaggagtacaagtgcaaggtctcc
```

-continued

```
aacaaaggcctcccgtcctccatcgagaaaaccatctccaaagccaaa gggcagccccgagagccacaggtgtacaccctgcccccatcccaggag gagatgaccaagaaccaggtcagcctgacctgcctggtcaaaggcttc taccccagcgacatcgccgtggagtgggagagcaatgggcagccggag aacaactacaagaccacgcctcccgtgctggactccgacggctccttc ttcctctacagcaggctaaccgtggacaagagcaggtggcaggaggg aatgtcttctcatgctccgtgatgcatgaggctctgcacaaccactac acacagaagagcctctccctgtccctaggtaaaatggccctgattgtg ctgggggggcgtcgccggcctcctgcttttcattgggctaggcatcttc ttcagagtgaagttcagcaggagcgcagacgcccccgcgtaccagcag ggccagaaccagctctataacgagctcaatctaggacgaagagaggag tacgatgttttggacaagagacgtggccgggaccctgagatgggggga aagccgagaaggaagaaccctcaggaaggcctgtacaatgaactgcag aaagataagatggcggaggcctacagtgagattgggatgaaaggcgag cgccggaggggcaaggggcacgatggcctttaccagggtctcagtaca gccaccaaggacacctacgacgcccttcacatgcaggccctgccccct cgc.
```

Example 3

Expression of the Immunoreceptor

Assessment of the integrity of the expressed construct was first delineated by Western blot probed with an anti-zeta antibody of whole cell lysates derived from Jurkat T cell stable transfectants[107] cocultured in the presence or absence of tunicamycin, an inhibitor of glycosylation. FIG. 1. Jurkat T cell stable transfectants (Jurkat-IL13-pMG bulk line) were obtained by electroporating Jurkat T cells with the IL13zetakine/HyTK-pMG expression vector, followed by selection and expansion of positive transfectants. 2×10⁶ cells from the Jurkat-IL13-pMG bulk line were plated per well in a 24-well plate with or without 5 µg/ml, 10 µg/ml, or 20 µg/ml Tunicamycin. The plate was incubated at 37° C. for 22hrs. Cells were harvested from each well, and each sample was washed with PBS and resuspended in 50 µRIPA buffer (PBS, 1% NP40, 0.5% sodium deoxycholate, 0.1% SDS) containing 1 tablet/10 ml Complete Protease Inhibitor Cocktail (Boehringer Mannheim, Indianapolis, IN). Samples were incubated on ice for 30 minutes then disrupted by aspiration with syringe with 21 gauge needle then incubated on ice for an additional 30 minutes before being centrifuged at 4° C. for 20 minutes at 14,000 rpm. Samples of centrifuged lysate supernatant were harvested and boiled in an equal volume of sample buffer under reducing conditions, then subjected to SDS-PAGE electrophoresis on a 12% acrylamide gel. Following transfer to nitrocellulose, membrane was allowed to dry O/N at 4° C. Next morning, membrane was blocked in a Blotto solution containing 0.04 gm/ml non-fat dried milk in T-TBS (0.02% Tween 20 in Tris buffered saline pH 8.0) for 1 hour. Membrane was then incubated with primary mouse anti-human CD3ζ monoclonal antibody (Pharmingen, San Diego, Calif.) at a concentration of 1 µg/ml for 2 hours, washed, and then incubated with a 1:3000 dilution (in Blotto solution) of goat anti-mouse IgG alkaline phosphatase conjugated secondary antibody (Bio-Rad ImmunoStar Kit, Hercules, Calif.) for 1 hour. Prior to developing, membrane was washed 4 additional times in T-TBS, and then incubated with 3 ml of phosphatase substrate solution (Biorad ImmunoStar Kit, Hercules, Calif.) for 5 minutes at room temperature. Membrane was then covered with plastic, and exposed to x-ray film. Consistant with the known glycosylation pattern of wild-type human IL-13, the electrophoretic mobility of expressed IL-13(E13Y) zetakine is demonstrative of a heavily glycosylated protein which, when expressed in the presence of tunicamycin, is reduced to an amino acid backbone of approximately 54 kDa.

The IL-13(E13Y) zetakine traffics to the cell surface as a homodimeric type I transmembrane protein, as evidenced by flow cytometric analysis of transfectants with a phycoerythrin (PE)-conjugated anti human-IL13 monoclonal antibody and a fluorescein isothiocyanate (FITC)-conjugated mouse anti-human Fc (gamma) fragment-specific F(ab')$_2$ antibody. FIG. 2. Jurkat IL13zetakine-pMG transfectants were stained with anti-human Fc(FITC) antibody (Jackson ImmunoResearch, West Grove, Pa.), recombinant human IL13Rα2/human IgG1 chimera (R&D Systems, Minneapolis, Minn.) followed by FITC-conjugated anti human-IgG1 monoclonal antibody (Sigma, St. Louis, Mo.), and an anti-IL13(PE) antibody (Becton Dickinson, San Jose, Calif.) for analysis of cell surface chimeric receptor expression. Healthy donor primary cells were also stained with FITC-conjugated anti-CD4, anti-CD8, anti-TCR, and isotype control monoclonal antibodies (Becton Dickinson, San Jose, Calif.) to assess cell surface phenotype. For each stain, $10^6$ cells were washed and resuspended in 100 µl of PBS containing 2% FCS, 0.2 mg/ml NaN$_3$, and 5 µl of stock antibody. Following a 30 minute incubation at 4° C., cells were washed twice and either stained with a secondary antibody, or resuspended in PBS containing 1% paraformaldehyde and analyzed on a FACSCaliber cytometer.

Example 4

Binding of IL13(E13Y) zetakine to IL13Rα2 receptor

Figure 3C:
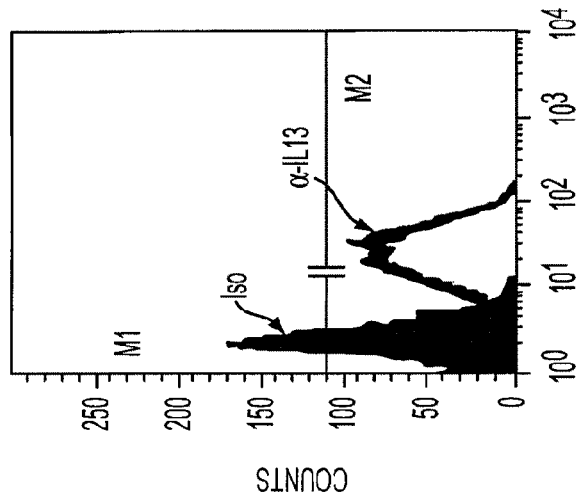
FIG. 3C: αIL13).
Figure 3B:
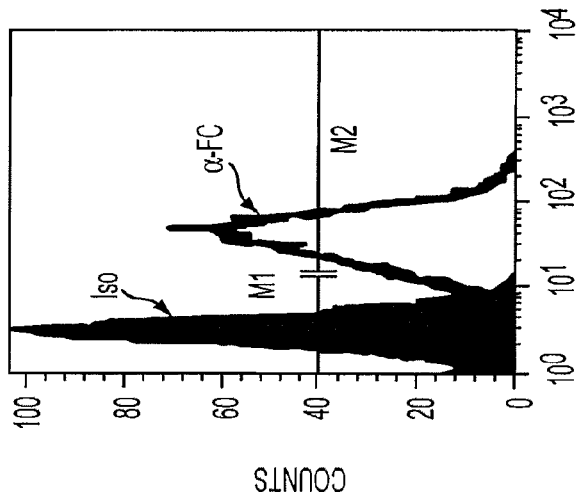
FIG. 3B: αFC.
Figure 3A:
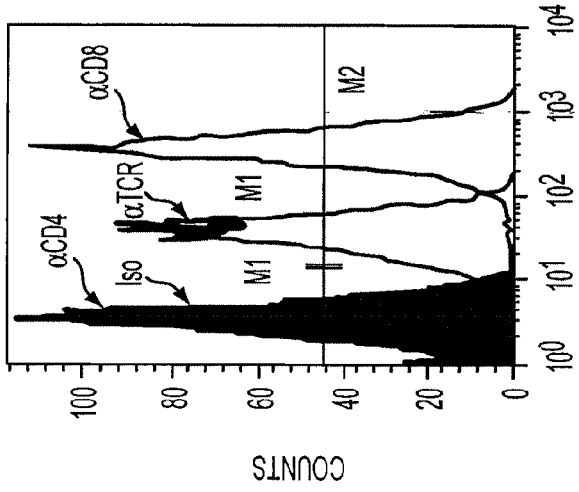
FIG. 3: Results of flow cytometric analysis showing the cell surface phenotype of a representative primary human IL13zetakine+ CTL clone (FIG. 3A: αCD4, αCDB, αTCR.
Figure 4C:
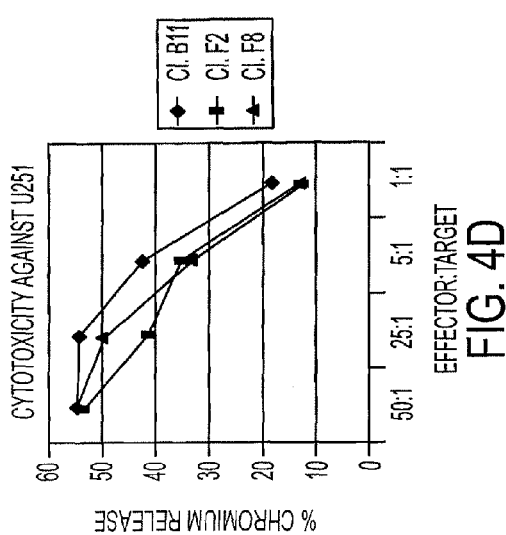
FIGS. 4C, 4D, 4E and 4F show the profile of anti-glioma cytolytic activity by primary human IL13zetakine+ CD8+ CTL clones was observed in glioma cells generally.
Figure 4D:
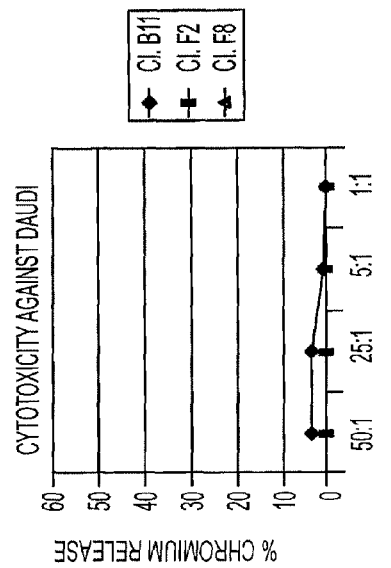
Figure 4E:
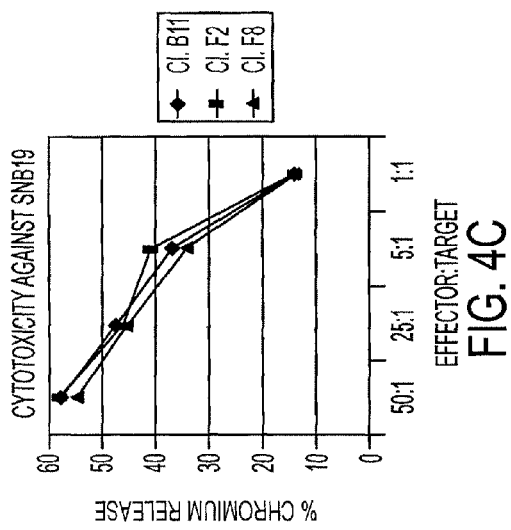
Figure 4F:
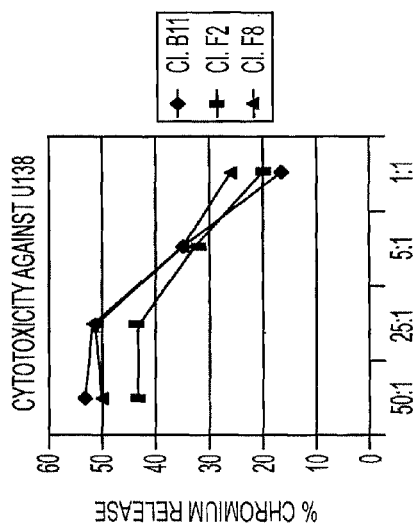

IL-13(E13Y), tethered to the cell membrane by human IgG4 Fc (i.e., IL13(E13Y) zetakine), is capable of binding to its target IL13Rα2 receptor as assessed by flow cytometric analysis using soluble IL13Rα2-Fc fusion protein. FIG. 3. Cloned human PBMC IL13zetakine-pMG transfectants were obtained by electroporating PBMC with the IL13zetakine/HyTK-pMG expression vector, followed by selection and expansion of positive transfectants[107]. IL13zetakine+ CTL clonal cells were stained with a fluorescein isothiocyanate (FITC)-conjugated mouse anti-human Fc (gamma) fragment-specific F(ab')$_2$ (Jackson ImmunoResearch, West Grove, Pa.), recombinant human IL13Rα2/human IgG1 chimera (R&D Systems, Minneapolis, Minn.) followed by FITC-conjugated anti human-IgG1 monoclonal antibody (Sigma, St. Louis, Mo.), and a phycoerythrin (PE)-conjugated anti human-IL13 monoclonal antibody (Becton Dickinson, San Jose, Calif.) for analysis of cell surface chimeric receptor expression. Healthy donor primary cells were also stained with FITC-conjugated anti-CD4, anti-CD8, anti-TCR, and isotype control monoclonal antibodies (Becton Dickinson, San Jose, Calif.) to assess cell surface phenotype. For each stain, $10^6$ cells were washed and resuspended in 100 µl of PBS containing 2% FCS, 0.2 mg/ml NaN$_3$, and 5 µl of antibody. Following a 30 minute incubation at 4° C., cells were washed twice and either stained with a secondary antibody, or resuspended in PBS containing 1% paraformaldehyde and analyzed on a FACSCaliber cytometer.

Next, the immunobiology of the IL-13(E13Y) zetakine as a surrogate antigen receptor for primary human T cells was evaluated. Primary human T cells were electroporated with the plasmid expression vector. Positive transformants were selected with hygromycin, cloned in limiting dilution, then expanded by recursive stimulation cycles with OKT3, IL-2 and irradiated feeder cells. Clones demonstrating IL 13zetakine expression by Western blot and FACS were then subjected to functional evaluation in 4-hr chromium release assays against a variety of IL-13α2+/CD20− glioma cell lines (U251, SN-B19, U138), and the IL-13α−/CD20+ B cell lymphocyte line Daudi). These tests showed that IL13zetakine conferred cytolytic activity that was specific for glioma cells (FIGS. 4A and 4B), and that this specific cytolytic activity is present for glioma cells as a class (FIGS. 4C, 4D, 4E and 4F). The cytolytic activity of MJ-IL13-pMG clones was assayed by employing $^{51}$Cr-labeled SN-B19, U251, and U138 glioma cell lines (IL13α2+/CD20−) and Daudi (CD20+/IL13α2−) as targets. MJ-IL13 effectors were assayed 8-12 days following stimulation. Effectors were harvested, washed, and resuspended in assay media: $2.5 \times 10^5$, $1.25 \times 10^5$, $2.5 \times 10^4$, and $5 \times 10^3$ effectors were cultured in triplicate at 37° C. for 4 hours with $5 \times 10^3$ target cells in 96-well V-bottom microtiter plates. After incubation, 100 µl aliquots of cell-free supernatant were harvested and $^{51}$Cr in the supernatants was assayed with a γ-counter. Percent specific cytolysis was calculated as follows:

$$\frac{\text{(Experimental }^{51}\text{Cr release)} - \text{(control }^{51}\text{Cr release)}}{\text{(Maximum }^{51}\text{Cr release)} - \text{(control }^{51}\text{Cr release)}} \times 100$$

Control wells contained target cells incubated in the presence of target cells alone. Maximum $^{51}$Cr release was determined by measuring the $^{51}$Cr released by labeled target cells in the presence of 2% SDS. Bulk lines of stabley transfected human T cells consisting of approximately 40% IL-13(E13Y) zetakine+TCRα/β+ lymphocytes displayed re-directed cytolysis specific for 13Rα2+ glioma targets in 4-hr chromium release assays (>50% specific lysis at E:T ratios of 25:1), with negligible activity against IL-13Rα2− targets (<8% specific lysis at E:T ratios of 25:1). IL-13(E13Y) zetakine+CD8+TCRα/β+ CTL clones selected on the basis of high-level binding to anti-IL-13 antibody also display redirected IL13Rα2-specific glioma cell killing. FIGS. 4C, 4D, 4E and 4F.

Figure 5A:
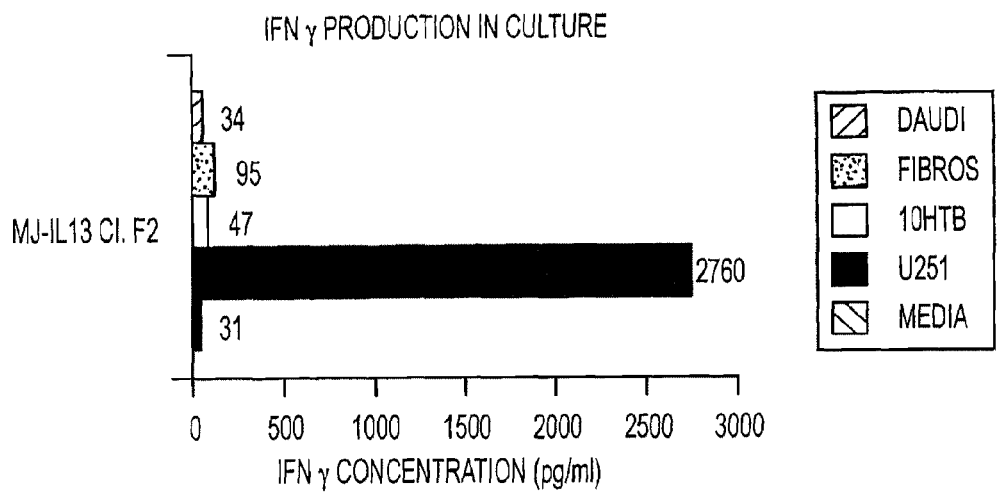
FIG. 5: Results of in vitro stimulation of cytokine production, showing that IL13zetakine+ CTL clones are activated for cytokine production by glioma stimulator cells (FIG. 5A: IFNγ concentration.
FIG. 5B: GM-CSF concentration.
FIG. 5C: TNFα concentration).
Figure 5B:
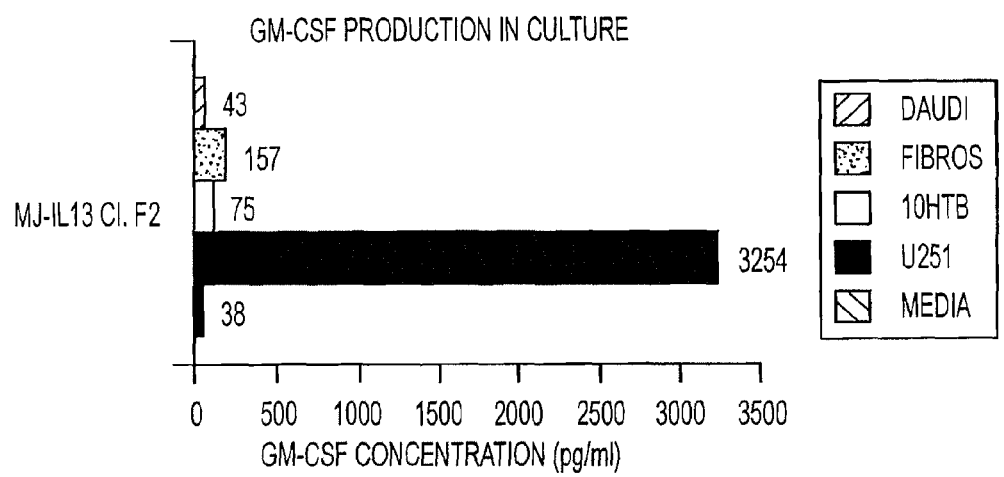
Figure 5C:
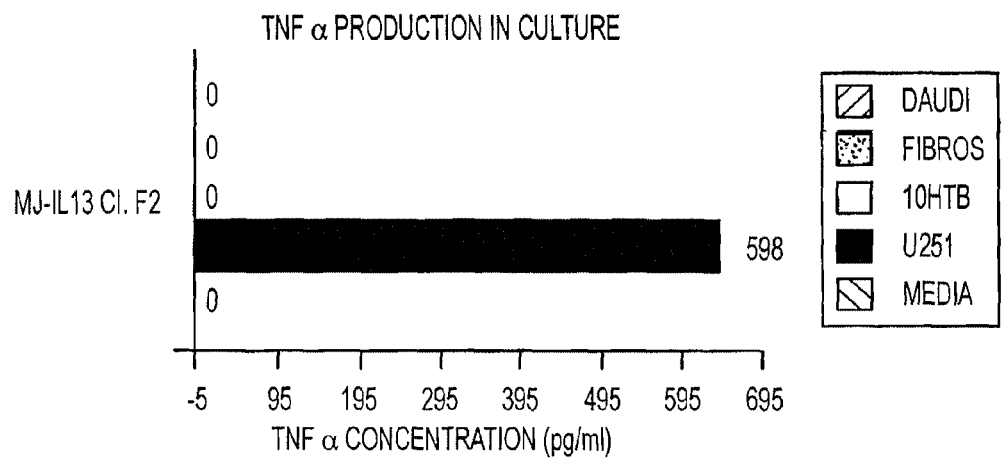
Figure 6A:
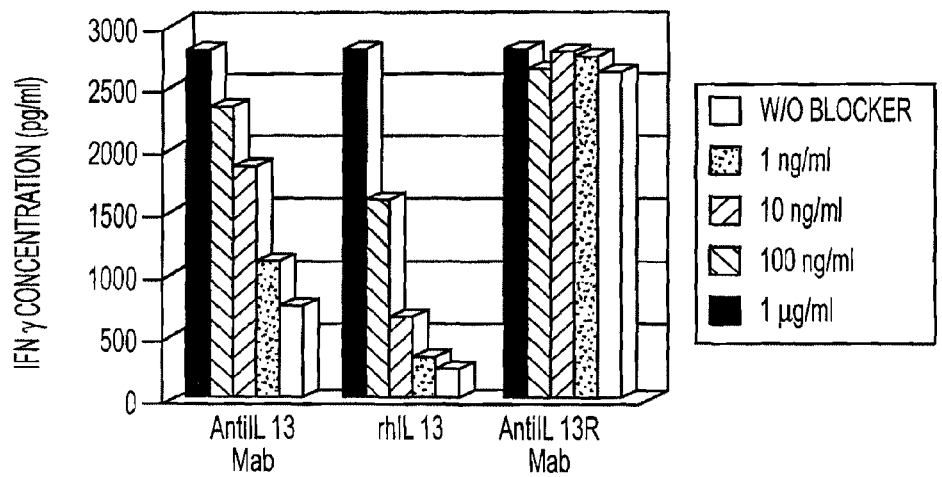
FIG. 6: Results of in vitro stimulation of cytokine production (FIG. 6A, IFNγ.
FIG. 6B, TNFα.
FIG. 6C, GM-CSF), showing the specific inhibition of IL13zetakine+ CTL activation for cytokine production by anti-IL13R Mab and rhIL13.
Figure 6B:
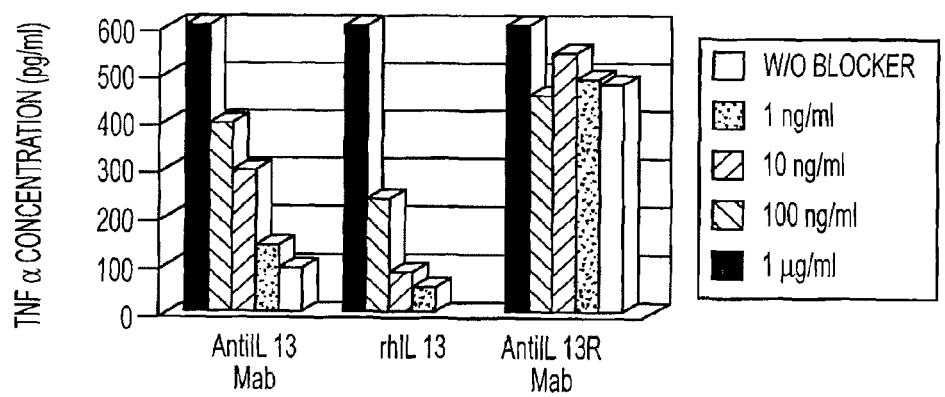
Figure 6C:
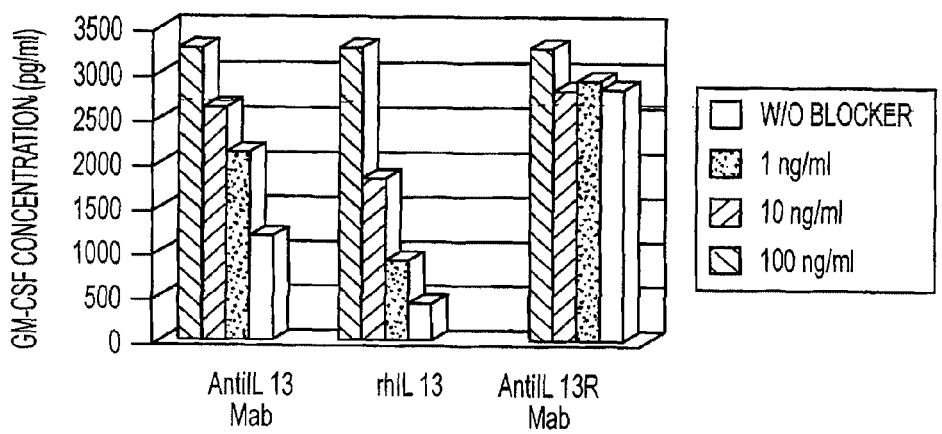
Figure 7A:
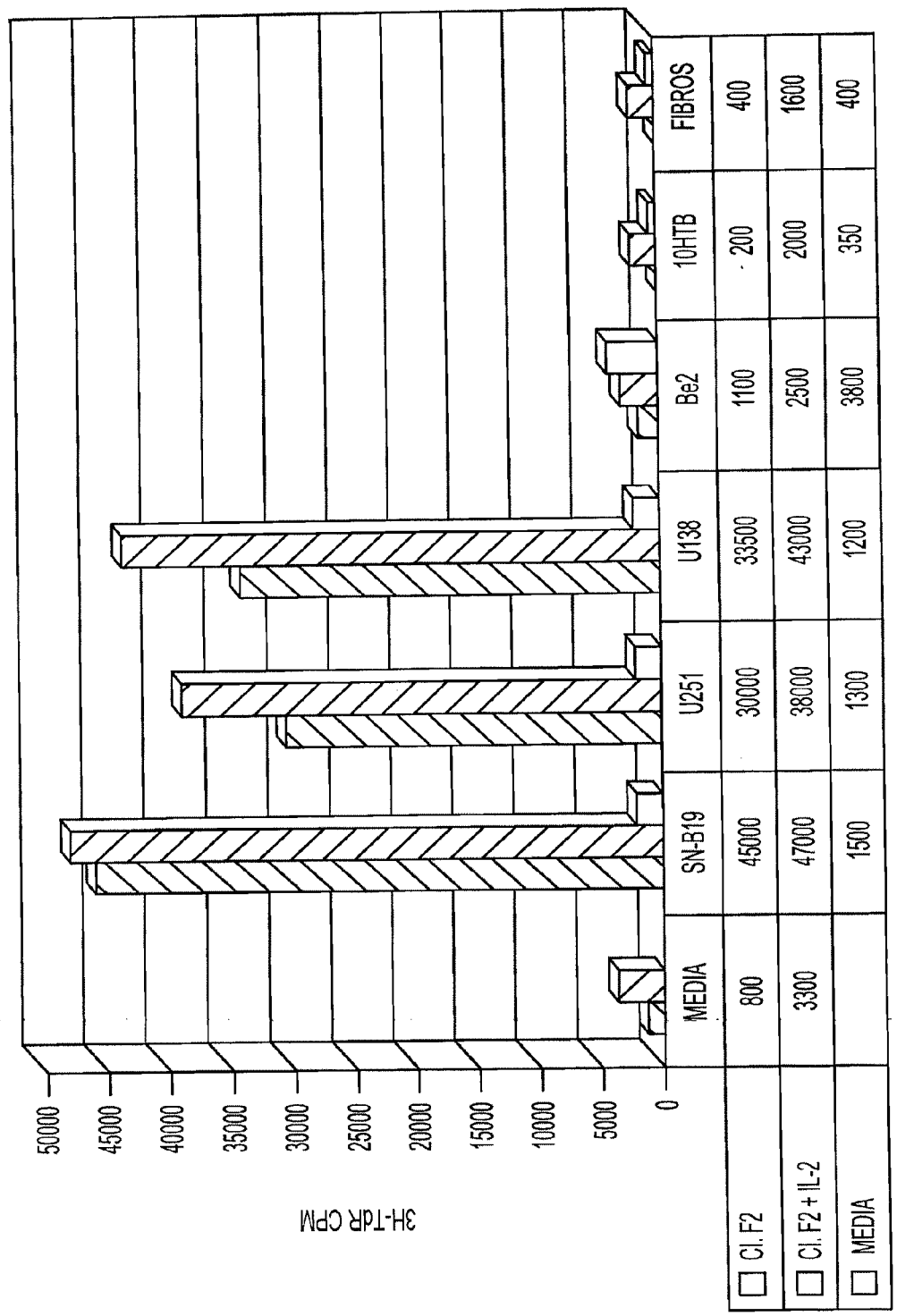
FIG. 7A shows that IL13zetakine+ CD8+ CTL cells proliferate upon co-culture with glioma stimulators.
Figure 7B:
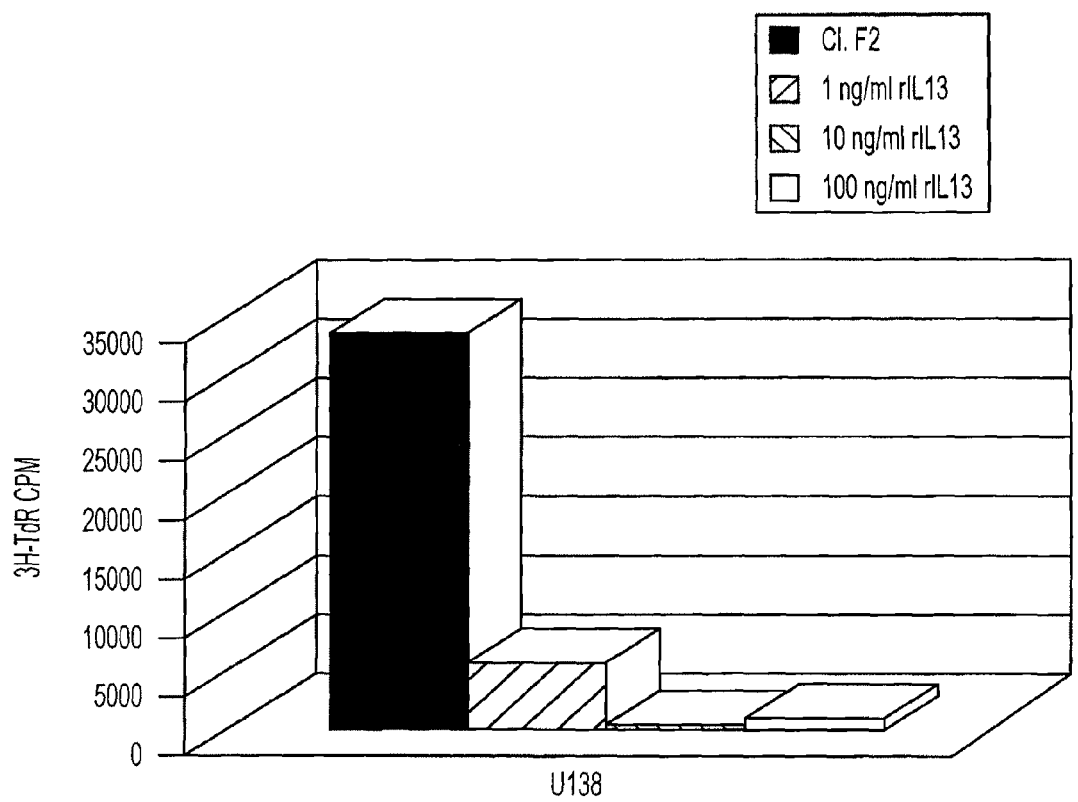
FIG. 7B shows the inhibition of glioma-stimulated proliferation of IL13zetakine+ CD8+ CTL cells by rhIL-13.

IL-13 zetakine-expressing CD8+ CTL clones are activated and proliferate when stimulated by glioma cells in culture. FIGS. 5-7. MJ-IL13-pMG Cl. F2 responder cells expressing the IL13 zetakine were evaluated for receptor-mediated triggering of IFNγ, GM-CSF, and TNFα production in vitro. $2 \times 10^6$ responder cells were co-cultured in 24-well tissue culture plates with $2 \times 10^5$ irradiated stimulator cells (Daudi, Fibroblasts, Neuroblastoma 10HTB, and glioblastoma 0251) in 2 ml total. Blocking rat anti-human-IL13 monoclonal antibody (Pharmingen, San Diego, Calif.), recombinant human IL13 (R&D Systems, Minneapolis, Minn.), and IL13Rα2-specific goat IgG (R&D Systems, Minneapolis, Minn.) were added to aliquots of 0251 stimulator cells ($2 \times 10^5$/ml) at concentrations of 1 ng/ml, 10 ng/ml, 100 ng/ml, and 1 µg/ml, 30 minutes prior to the addition of responder cells. Plates were incubated for 72 hours at 37° C., after which time culture supernatants were harvested, aliquoted, and stored at −70° C. ELISA assays for IFNγ, GM-CSF, and TNFα were carried out using the R&D Systems (Minneapolis, Minn.) kit per manufacturer's instructions. Samples were tested in duplicate wells undiluted or diluted at 1:5 or 1:10. The developed ELISA plate was evaluated on a microplate reader and cytokine concentrations determined by extrapolation from a standard curve. Results are reported as picograms/ml, and show strong activation for cytokine production by glioma stimulator cells. FIG. 5, FIG. 6.

Lastly, IL-2 independent proliferation of IL13zetakine$^+$ CD8$^+$ CTL was observed upon co-cultivation with glioma stimulators (FIG. 7A), but not with IL13 R$\alpha$2 stimulators. Proliferation was inhibited by the addition of rhIL-13 antibody (FIG. 7B), showing that the observed proliferation was dependant on binding of zetakine to the IL-13R$\alpha$2 glioma cell-sepcific receptor.

Example 5

Preparation of IL-13 Zetakine$^+$ T Cells Suitable for Therapeutic Use

The mononuclear cells are separated from heparinized whole blood by centrifugation over clinical grade Ficoll (Pharmacia, Uppsula, Sweden). PBMC are washed twice in sterile phosphate buffered saline (Irvine Scientific) and suspended in culture media consisting of RPMI 1640 HEPES, 10% heat inactivated FCS, and 4 mM L-glutamine. T cells present in patient PBMC are polyclonally activated by addition to culture of Orthoclone OKT3 (30 ng/ml). Cell cultures are then incubated in vented T75 tissue culture flasks in the study subject's designated incubator. Twenty-four hours after initiation of culture rhIL-2 is added at 25 U/ml.

Three days after the initiation of culture PBMC are harvested, centrifuged, and resuspended in hypotonic electroporation buffer (Eppendorf) at $20\times10^6$ cells/ml. 25 µg of the plasmid IL13zetakine/HyTK-pMG of Example 3, together with 400 µl of cell suspension, are added to a sterile 0.2 cm electroporation cuvette. Each cuvette is subjected to a single electrical pulse of 250V/40 µs and again incubated for ten minutes at RT. Surviving cells are harvested from cuvettes, pooled, and resuspended in culture media containing 25 U/ml rhIL-2. Flasks are placed in the patient's designated tissue culture incubator. Three days following electroporation hygromycin is added to cells at a final concentration of 0.2 mg/ml. Electroporated PBMC are cultured for a total of 14 days with media and IL-2 supplementation every 48-hours.

The cloning of hygromycin-resistant CD8+ CTL from electroporated OKT3-activated patient PBMC is initiated on day 14 of culture. Briefly, viable patient PBMC are added to a mixture of $100\times10^6$ cyropreserved irradiated feeder PBMC and $20\times10^6$ irradiated TM-LCL in a volume of 200 ml of culture media containing 30 ng/ml OKT3 and 50 U/ml rhIL-2. This mastermix is plated into ten 96-well cloning plates with each well receiving 0.2 ml. Plates are wrapped in aluminum foil to decrease evaporative loss and placed in the patient's designated tissue culture incubator. On day 19 of culture each well receives hygromycin for a final concentration of 0.2 mg/ml. Wells are inspected for cellular outgrowth by visualization on an inverted microscope at Day 30 and positive wells are marked for restimulation.

The contents of each cloning well with cell growth are individually transferred to T25 flasks containing $50\times10^6$ irradiated PBMC, $10\times10^6$ irradiated LCL, and 30 ng/ml OKT3 in 25 mls of tissue culture media. On days 1, 3, 5, 7, 9, 11, and 13 after restimulation flasks receive 50 U/ml rhIL-2 and 15 mls of fresh media. On day 5 of the stimulation cycle flasks are also supplemented with hygromycin 0.2 mg/ml. Fourteen days after seeding cells are harvested, counted, and restimulated in T75 flasks containing $150\times10^6$ irradiated PBMC, $30\times10^6$ irradiated TM-LCL and 30 ng/ml OKT3 in 50 mls of tissue culture media. Flasks receive additions to culture of rhIL-2 and hygromycin as outlined above.

CTL selected for expansion for possible use in therapy are analyzed by immunofluorescence on a FACSCalibur housed in CRB-3006 using FITC-conjugated monoclonal antibodies WT/31 ($\alpha\beta$TCR), Leu 2a (CD8), and OKT4 (CD4) to confirm the requisite phenotype of clones ($\alpha\beta$TCR+, CD4−, CD8+, and IL13+). Criteria for selection of clones for clinical use include uniform TCR $\alpha\beta$+, CD4−, CD8+ and IL13+ as compared to isotype control FITC/PE-conjugated antibody. A single site of plasmid vector chromosomal integration is confirmed by Southern blot analysis. DNA from genetically modified T cell clones will be screened with a DNA probe specific for the plasmid vector. Probe DNA specific for the HyTK in the plasmid vector is synthesized by random priming with florescein-conjugated dUTP per the manufacture's instructions (Amersham, Arlington Hts, Ill.). T cell genomic DNA is isolated per standard technique. Ten micrograms of genomic DNA from T cell clones is digested overnight at 37° C. then electrophoretically separated on a 0.85% agarose gel. DNA is then transferred to nylon filters (BioRad, Hercules, Calif.) using an alkaline capillary transfer method. Filters are hybridized overnight with probe in 0.5 M Na$_2$PO$_4$, pH 7.2, 7% SDS, containing 10 µg/ml salmon sperm DNA (Sigma) at 65° C. Filters are then washed four times in 40 mM Na$_2$PO$_4$, pH 7.2, 1% SDS at 65° C. and then visualized using a chemiluminescence AP-conjugated anti-florescein antibody (Amersham, Arlington Hts, Ill.). Criteria for clone selection is a single band unique vector band.

Expression of the IL-13 zetakine is determined by Western blot procedure in which chimeric receptor protein is detected with an anti-zeta antibody. Whole cell lysates of transfected T cell clones are generated by lysis of $2\times10^7$ washed cells in 1 ml of RIPA buffer (PBS, 1% NP40, 0.5% sodium deoxycholate, 0.1% SDS) containing 1 tablet/10 ml Complete Protease Inhibitor Cocktail (Boehringer Mannheim). After an eighty minute incubation on ice, aliquots of centrifuged whole cell lysate supernatant are harvested and boiled in an equal volume of loading buffer under reducing conditions then subjected to SDS-PAGE electrophoresis on a precast 12% acrylamide gel (BioRad). Following transfer to nitrocellulose, membranes are blocked in blotto solution containing 0.07 gm/ml non-fat dried milk for 2 hours. Membranes are washed in T-TBS (0.05% Tween 20 in Tris buffered saline pH 8.0) then incubated with primary mouse anti-human CD3$\zeta$ monoclonal antibody 8D3 (Pharmingen, San Diego, Calif.) at a concentration of 1 µg/ml for 2 hours. Following an additional four washes in T-TBS, membranes are incubated with a 1:500 dilution of goat anti-mouse IgG alkaline phosphatase-conjugated secondary antibody for 1 hour. Prior to developing, membranes are rinsed in T-TBS then developed with 30 ml of "AKP" solution (Promega, Madison, Wis.) per the manufacturer's instructions. Criteria for clone selection is the presence of a chimeric zeta band.

CD8+ cytotoxic T cell clones expressing the IL-13 zetakine chimeric immunoreceptor recognize and lyse human glioblastoma target cells following interaction of the chimeric receptor with the cell surface target epitope in a HLA-unrestricted fashion. The requirements for target IL-13R$\alpha$2 epitope expression and class I MHC independent recognition will be confirmed by assaying each $\alpha\beta$TCR+, CD8+, CD4−, IL-13 zetakine+ CTL clones against IL-13R$\alpha$2+ Daudi cell transfectants and IL-13R$\alpha$2− Daudi cells. T cell effectors are assayed 12-14 days following stimulation with OKT3. Effectors are harvested, washed, and resuspended in assay media;

and Daudi cell transfectants expressing IL-13Rα2. $2.5\times10^5$, $1.25\times10^5$, $0.25\times10^5$, and $0.05\times10^5$ effectors are plated in triplicate at 37° C. for 4 hours with $5\times10^3$ target cells in V-bottom microtiter plates (Costar, Cambridge, Mass.). After centrifugation and incubation, 100 µL aliquots of cell-free supernatant is harvested and counted. Percent specific cytolysis is calculated as:

$$\frac{(\text{Experimental }^{51}\text{Cr release}) - (\text{control }^{51}\text{Cr release})}{(\text{Maximum }^{51}\text{Cr release}) - (\text{control }^{51}\text{Cr release})} \times 100$$

Control wells contain target cells incubated in assay media. Maximum $^{51}$Cr release is determined by measuring the $^{51}$Cr content of target cells lysed with 2% SDS. Criteria for clone selection is >25% specific lysis of IL-13Rα2+Daudi transfectants at an E:T ratio of 5:1 and a <10% lysis of parental Daudi at the same E:T ratio.

Example 6

Treatment of Human Glioma Using IL-13 Zetakine-Expressing T Cells

T cell clones genetically modified according to Example 5 to express the IL-13R zetakine chimeric immunoreceptor and HyTK are selected for:

a. TCRα/β+, CD4−, CD8+, IL-13+ cell surface phenotype as determined by flow cytometry.
b. Presence of a single copy of chromosomally integrated plasmid vector DNA as evidenced by Southern blot.
c. Expression of the IL-13 zetakine protein as detected by Western blot.
d. Specific lysis of human IL-13Rα2+ targets in 4-hr chromium release assays.
e. Dependence on exogenous IL-2 for in vitro growth.
f. *Mycoplasma*, fungal, bacterial sterility and endotoxin levels <5 EU/ml.
g. In vitro sensitivity of clones to ganciclovir.

Peripheral blood mononuclear cells are obtained from the patient by leukapheresis, preferably following recovery from initial resection surgery and at a time at least three weeks from tapering off steroids and/or their most recent systemic chemotherapy. The target leukapheresis mononuclear cell yield is $5\times10^9$ and the target number of hygromycin-resistant cytolytic T cell clones is 25 with the expectation that at least five clones will be identified that meet all quality control parameters for ex-vivo expansion. Clones are cryopreserved and patients monitored by serial radiographic and clinical examinations. When recurrence of progression of disease is documented, patients undergo a re-resection and/or placement of a reservoir-access device (Omaya reservoir) for delivering T cells to the tumor resection cavity. Following recovery from surgery and tapering of steroids, if applicable, the patient commences with T cell therapy.

The patient receives a target of at least four one-week cycles of therapy. During the first cycle, cell dose escalation proceeds from an initial dose on Day 0 of $10^7$ cells, followed by $5\times10^7$ cells on Day 3 to the target dose of $10^8$ cells on Day 5. Cycle 2 commences as early as one week from commencement of cycle 1. Those patients demonstrating tumor regression with residual disease on MRI may have additional courses of therapy beginning no earlier than Week 7 consisting of repetition of Cycles 3 and 4 followed by one week of rest/restaging provided these treatments are well tolerated (max. toxicities<grade 3) until such time that disease progression or a CR is achieved based on radiographic evaluation.

Cell doses are at least a log less than doses given in studies employing intracavitary LAK cells (individual cell doses of up to $10^9$ and cumulative cell numbers as high as $2.75\times10^{10}$ have been safety administered), ex vivo expanded TILs (up to $10^9$ cells/dose reported with minimal toxicity) and allo-reactive lymphocyte (starting cell dose $10^8$ with cumulative cell doses up to $51.5\times10^8$) delivered to a similar patient population[75-85]. The rationale for the lower cell doses as proposed in this protocol is based on the increased in vitro reactivity/anti-tumor potency of IL-13 zetakine+ CTL clones compared to the modest reactivity profile of previously utilized effector cell populations. Low-dose repetitive dosing is favored to avoid potentially dangerous inflammatory responses that might occur with single large cell number instillations. Each infusion will consist of a single T cell clone. The same clone will be administered throughout a patient's treatment course. On the days of T cell administration, expanded clones are aseptically processed by washing twice in 50 cc of PBS then resuspended in pharmaceutical preservative-free normal saline in a volume that results in the cell dose for patient delivery in 2 mls. T cells are instilled over 5-10 minutes. A 2 ml PFNS flush will be administered over 5 minutes following T cells. Response to therapy is assessed by brain MRI+/− gandolinium, with spectroscopy.

Expected side-effects of administration of T cells into glioma resection cavities typically consist of self-limited nausea and vomiting, fever, and transient worsening of existing neurological deficits. These toxicities can be attributed to both the local inflammation/edema in the tumor bed mediated by T cells in combination with the action of secreted cytokines. These side-effects typically are transient and less than grade II in severity. Should patients experience more severe toxicities it is expected that decadron alone or in combination with ganciclovir will attenuate the inflammatory process and ablate the infused cells. The inadvertent infusion of a cell product that is contaminated with bacteria or fungus has the potential of mediating serious or life-threatening toxicities. Extensive pre-infusion culturing of the cell product is conducted to identify contaminated tissue culture flasks and minimize this possibility. On the day of re-infusion, gram stains of culture fluids, as well as, endotoxin levels are performed.

Extensive molecular analysis for expression of IL-13Rα2 has demonstrated that this molecule is tumor-specific in the context of the CNS[44; 46; 48; 54]. Furthermore, the only human tissue with demonstrable IL-13Rα2 expression appears to be the testis[42]. This tumor-testis restrictive pattern of expression is reminiscent of the growing number of tumor antigens (i.e. MAGE, BAGE, GAGE) expressed by a variety of human cancers, most notably melanoma and renal cell carcinoma[109-111]. Clinical experience with vaccine and adoptive T cell therapy has demonstrated that this class of antigens can be exploited for systemic tumor immunotherapy without concurrent autoimmune attack of the testis[112-114]. Presumably this selectively reflects the effect of an intact blood-testis barrier and an immunologically privileged environment within the testis. Despite the exquisite specificity of the mutant IL-13 targeting moiety, toxicities are theoretically possible if cells egress into the systemic circulation in sufficient numbers and recognize tissues expressing the IL-13Rα1/IL-4β receptor. In light of this remote risk, as well as the possibility that instilled T cells in some patients may mediate an overly exuberant inflammatory response in the tumor bed, clones are equipped with the HyTK gene which renders T cells susceptible to in vivo ablation with ganciclovir[115-118]. Ganciclovir-suicide, in combination with an intra-patient T cell dose escalation strategy, helps minimize the potential risk to research participants.

Side effects associated with therapy (headache, fever, chills, nausea, etc.) are managed using established treatments appropriate for the condition. The patient receives ganciclovir if any new grade 3 or any grade 4 treatment-related toxicity is observed that, in the opinion of the treating physician, puts that patient at significant medical danger. Parentally administered ganciclovir is dosed at 10 mg/kg/day divided every 12 hours. A 14-day course will be prescribed but may be extended should symptomatic resolution not be achieved in that time interval. Treatment with ganciclovir leads to the ablation of IL-13 zetakine+ HyTK+ CD8+ CTL clones. Patients should be hospitalized for the first 72 hours of ganciclovir therapy for monitoring purposes. If symptoms do not respond to ganciclovir within 48 hours additional immunosuppressive agents including but not limited to corticosteroids and cyclosporin may be added at the discretion of the treating physician. If toxicities are severe, decadron and/or other immunosuppressive drugs along with ganciclovir are used earlier at the discretion of the treating physician.

Example 7

Additional Preferred DNA Vectors

Figure 10:
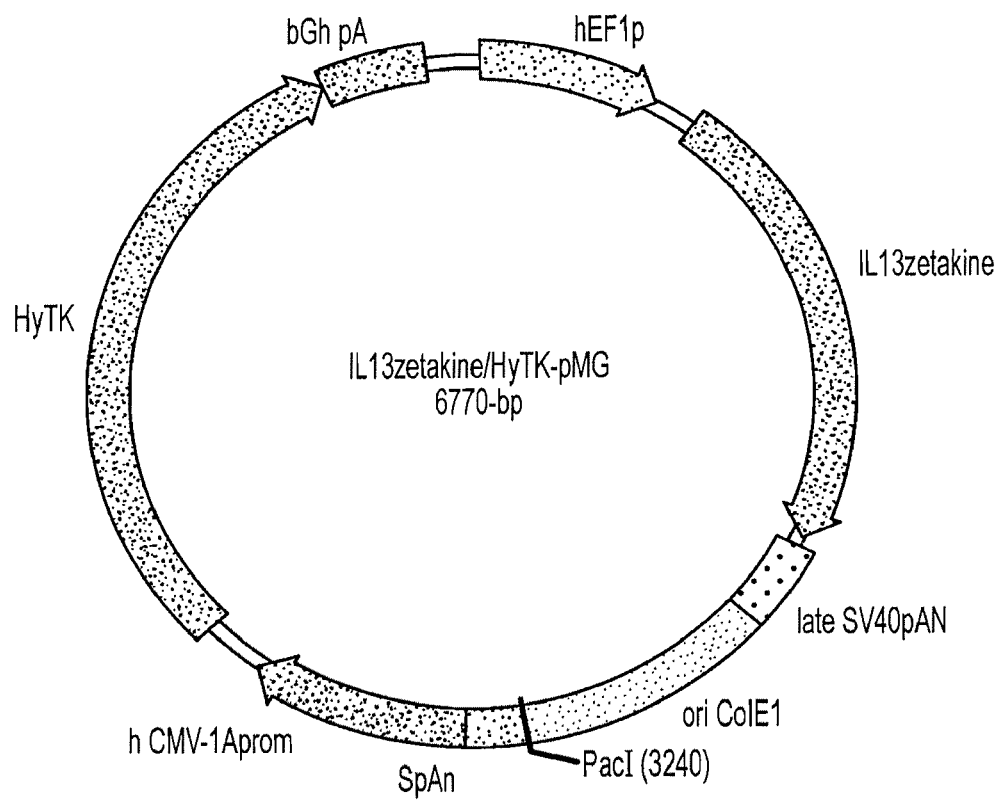
FIG. 10: Plasmid map of alternative IL13zetakine/HyTK-pMG.

Additional DNA vectors are shown in FIGS. 12-14. Table I, below contains further information concerning the sequence of FIG. 13. See FIG. 10 for a map of this vector.

TABLE I

Plasmid DNA Vector Sequence Contents for SEQ ID NO: 19.

| Plasmid Element | Description | Location (bases) |
| --- | --- | --- |
| hEF1p | Human Elongation Factor-1α Promoter | 6-549 |
| IL13zetakine | IL13 cytokine fused to Fc: ζ | 690-2183 |
| Late SV40pAn | Simian Virus 40 Late polyadenylation signal | 2230-2498 |
| Orin ColE1 | A minimal *E. coli* origin of replication | 2499-3245 |
| SpAn | A synthetic poly A and Pause site | 3246-3432 |
| hCMV-1Aprom | Immediate-early CMV enhancer/promoter | 3433-4075 |
| HyTK | Genetic fusion of the Hygromycin Resistance and Thymidine Kinase coding regions | 4244-6319 |
| BGh pAn | Bovine growth hormone polyadenylation signal and a transcriptional pause | 6320-6618 |

REFERENCES

1. Davis F G, McCarthy B J. Epidemiology of brain tumors. Curr Opin Neurol. 2000; 13:635-640.
2. Davis F G, Malinski N, Haenszel W, et al. Primary brain tumor incidence rates in four United States regions, 1985-1989: a pilot study. Neuroepidemiology. 1996; 15:103-112.
3. Smith M A, Freidlin B, Ries L A, Simon R. Increased incidence rates but no space-time clustering of childhood astrocytoma in Sweden, 1973-1992: a population-based study of pediatric brain tumors. Cancer. 2000; 88:1492-1493.
4. Ahsan H, Neugut A I, Bruce J N. Trends in incidence of primary malignant brain tumors in USA, 1981-1990. Int J. Epidemiol. 1995; 24:1078-1085.
5. Ashby L S, Obbens E A, Shapiro W R. Brain tumors. Cancer Chemother Biol Response Modif. 1999; 18:498-549.
6. Davis F G, Freels S, Grutsch J, Barlas S, Brem S. Survival rates in patients with primary malignant brain tumors stratified by patient age and tumor histological type: an analysis based on Surveillance, Epidemiology, and End Results (SEER) data, 1973-1991. J. Neurosurg. 1998; 88:1-10.
7. Duffner P K, Cohen M E, Myers M H, Heise H W. Survival of children with brain tumors: SEER Program, 1973-1980. Neurology. 1986; 36:597-601.
8. Davis F G, Freels S, Grutsch J, Barlas S, Brem S. Survival rates in patients with primary malignant brain tumors stratified by patient age and tumor histological type: an analysis based on Surveillance, Epidemiology, and End Results (SEER) data, 1973-1991. J Neurosurg. 1998; 88:1-10.
9. Kolles H, Niedermayer I, Feiden W. Grading of astrocytomas and oligodendrogliomas. Pathologe. 1998; 19:259-268.
10. Huncharek M, Muscat J. Treatment of recurrent high grade astrocytoma; results of a systematic review of 1,415 patients. Anticancer Res. 1998; 18:1303-1311.
11. Loiseau H, Kantor G. The role of surgery in the treatment of glial tumors. Cancer Radiother. 2000; 4 Suppl 1:48s-52s.
12. Palma L. Trends in surgical management of astrocytomas and other brain gliomas. Forum (Genova). 1998; 8:272-281.
13. Azizi S A, Miyamoto C. Principles of treatment of malignant gliomas in adults: an overview. J. Neurovirol. 1998; 4:204-216.
14. Shapiro W R, Shapiro J R. Biology and treatment of malignant glioma. Oncology (Huntingt). 1998; 12:233-240.
15. Chamberlain M C, Kormanik P A. Practical guidelines for the treatment of malignant gliomas. West J Med. 1998; 168:114-120.
16. Ushio Y. Treatment of gliomas in adults. Curr Opin Oncol. 1991; 3:467-475.
17. Scott J N, Rewcastle N B, Brasher P M, et al. Long-term glioblastoma multiforme survivors: a population-based study. Can J Neurol Sci. 1998; 25:197-201.
18. Finlay J L, Wisoff J H. The impact of extent of resection in the management of malignant gliomas of childhood. Childs Nery Syst. 1999; 15:786-788.
19. Hess K R. Extent of resection as a prognostic variable in the treatment of gliomas. J Neurooncol. 1999; 42:227-231.
20. van den Bent M J. Chemotherapy in adult malignant glioma. Front Radiat Ther Oncol. 1999; 33:174-191.
21. DeAngelis L M, Burger P C, Green S B, Cairncross J G. Malignant glioma: who benefits from adjuvant chemotherapy? Ann Neurol. 1998; 44:691-695.
22. Armstrong T S, Gilbert M R. Chemotherapy of astrocytomas: an overview. Semin Oncol Nurs. 1998; 14:18-25.
23. Prados M D, Russo C. Chemotherapy of brain tumors. Semin Surg Oncol. 1998; 14:88-95.
24. Prados M D, Scott C, Curran W J, Nelson D F, Leibel S, Kramer S. Procarbazine, lomustine, and vincristine (PCV) chemotherapy for anaplastic astrocytoma: A retrospective review of radiation therapy oncology group protocols comparing survival with carmustine or PCV adjuvant chemotherapy. J Clin Oncol. 1999; 17:3389-3395.
25. Fine H A, Dear K B, Loeffler J S, Black P M, Canellos G P. Meta-analysis of radiation therapy with and without 26. Mahaley M S, Gillespie G Y. New therapeutic approaches to treatment of malignant gliomas: chemotherapy and immunotherapy. Clin Neurosurg. 1983; 31:456-469.
27. Millot F, Delval O, Giraud C, et al. High-dose chemotherapy with hematopoietic stem cell transplantation in adults with bone marrow relapse of medulloblastoma: report of two cases. Bone Marrow Transplant. 1999; 24:1347-1349.
28. Kalifa C, Valteau D, Pizer B, Vassal G, Grill J, Hartmann O. High-dose chemotherapy in childhood brain tumours. Childs Nery Syst. 1999; 15:498-505.
29. Finlay J L. The role of high-dose chemotherapy and stem cell rescue in the treatment of malignant brain tumors. Bone Marrow Transplant. 1996; 18 Suppl 3:S1-S5.
30. Brandes A A, Vastola F, Monfardini S. Reoperation in recurrent high-grade gliomas: literature review of prognostic factors and outcome. Am J Clin Oncol. 1999; 22:387-390.
31. Miyagi K, Ingram M, Techy G B, Jacques D B, Freshwater D B, Sheldon H. Immunohistochemical detection and correlation between MHC antigen and cell-mediated immune system in recurrent glioma by APAAP method. Neurol Med Chir (Tokyo). 1990; 30:649-655.
32. Bauman G S, Sneed P K, Wara W M, et al. Reirradiation of primary CNS tumors. Int Radiat Oncol Biol Phys. 1996; 36:433-441.
33. Fine H A. Novel biologic therapies for malignant gliomas. Antiangiogenesis, immunotherapy, and gene therapy. Neurol Clin. 1995; 13:827-846.
34. Brandes A A, Pasetto L M. New therapeutic agents in the treatment of recurrent high-grade gliomas. Forum (Genova). 2000; 10:121-131.
35. Pollack I F, Okada H, Chambers W H. Exploitation of immune mechanisms in the treatment of central nervous system cancer. Semin Pediatr Neurol. 2000; 7:131-143.
36. Black K L, Pikul B K. Gliomas—past, present, and future. Clin Neurosurg. 1999; 45:160-163.
37. Riva P, Franceschi G, Arista A, et al. Local application of radiolabeled monoclonal antibodies in the treatment of high grade malignant gliomas: a six-year clinical experience. Cancer. 1997; 802733-2742.
38. Liang B C, Weil M. Locoregional approaches to therapy with gliomas as the paradigm. Curr Opin Oncol. 1998; 10:201-206.
39. Yu J S, Wei M X, Chiocca E A, Martuza R L, Tepper R I. Treatment of glioma by engineered interleukin 4-secreting cells. Cancer Res. 1993; 53:3125-3128.
40. Alavi J B, Eck S L. Gene therapy for malignant gliomas. Hematol Oncol Clin North Am. 1998; 12:617-629.
41. Debinski W. Recombinant cytotoxins specific for cancer cells. Ann NY Acad. Sci. 1999; 886:297-299.
42. Debinski W, Gibo D M. Molecular expression analysis of restrictive receptor for interleukin 13, a brain tumor-associated cancer/testis antigen. Mol Med. 2000; 6:440-449.
43. Mintz A, Debinski W. Cancer genetics/epigenetics and the X chromosome: possible new links for malignant glioma pathogenesis and immune-based therapies. Crit Rev Oncog. 2000; 11:77-95.
44. Joshi B H, Plautz G E, Puri R K. Interleukin-13 receptor alpha chain: a novel tumor-associated transmembrane protein in primary explants of human malignant gliomas. Cancer Res. 2000; 60:1168-1172.
45. Debinski W, Obiri N I, Powers S K, Pastan I, Puri R K. Human glioma cells overexpress receptors for interleukin 13 and are extremely sensitive to a novel chimeric protein composed of interleukin 13 and pseudomonas exotoxin. Clin Cancer Res. 1995; 1:1253-1258.
46. Debinski W, Gibo D M, Hulet S W, Connor J R, Gillespie G Y. Receptor for interleukin 13 is a marker and therapeutic target for human high-grade gliomas. Clin Cancer Res. 1999; 5:985-990.
47. Debinski W. An immune regulatory cytokine receptor and glioblastoma multiforme: an unexpected link. Crit Rev Oncog. 1998; 9:255-268.
48. Debinski W, Slagle B, Gibo D M, Powers S K, Gillespie G Y. Expression of a restrictive receptor for interleukin 13 is associated with glial transformation. J Neurooncol. 2000; 48:103-111.
49. Debinski W, Miner R, Leland P, Obiri N I, Puri R K. Receptor for interleukin (IL) 13 does not interact with IL4 but receptor for IL4 interacts with IL13 on human glioma cells. Biol. Chem. 1996; 271:22428-22433.
50. Murata T, Obiri N I, Debinski W, Puri R K. Structure of IL-13 receptor: analysis of subunit composition in cancer and immune cells. Biochem Biophys Res Commun. 1997; 238:90-94.
51. Opal S M, DePalo V A. Anti-inflammatory cytokines. Chest. 2000; 117:1162-1172.
52. Romagnani S. T-cell subsets (Th1 versus Th2). Ann Allergy Asthma Immunol. 2000; 85:9-18.
53. Spellberg B, Edwards J E, Jr. Type 1/Type 2 immunity in infectious diseases. Clin Infect Dis. 2001; 32:76-102.
54. Liu H, Jacobs B S, Liu J, et al. Interleukin-13 sensitivity and receptor phenotypes of human glial cell lines: non-neoplastic glia and low-grade astrocytoma differ from malignant glioma. Cancer Immunol Immunother. 2000; 49:319-324.
55. Debinski W, Gibo D M, Obiri N I, Kealiher A, Puri R K. Novel anti-brain tumor cytotoxins specific for cancer cells. Nat Biotechnol. 1998; 16:449-453.
56. Debinski W, Gibo D M, Puri R K. Novel way to increase targeting specificity to a human glioblastoma-associated receptor for interleukin 13. Int J Cancer. 1998; 76:547-551.
57. Debinski W, Thompson J P. Retargeting interleukin 13 for radioimmunodetection and radioimmunotherapy of human high-grade gliomas. Clin Cancer Res. 1999; 5:3143s-3147s.
58. Thompson J P, Debinski W. Mutants of interleukin 13 with altered reactivity toward interleukin 13 receptors. J Biol Chem. 1999; 274:29944-29950.
59. Brooks W H, Netsky M G, Levine J E. Immunity and tumors of the nervous system. Surg Neurol. 1975; 3:184-186.
60. Bullard D E, Gillespie G Y, Mahaley M S, Bigner D D. Immunobiology of human gliomas. Semin Oncol. 1986; 13:94-109.
61. Coakham H B. Immunology of human brain tumors. Eur J Cancer Clin Oncol. 1984; 20:145-149.
62. Holladay F P, Heitz T, Wood G W. Antitumor activity against established intracerebral gliomas exhibited by cytotoxic T lymphocytes, but not by lymphokine-activated killer cells. J Neurosurg. 1992; 77:757-762.
63. Holladay F P, Heitz T, Chen Y L, Chiga M, Wood G W. Successful treatment of a malignant rat glioma with cytotoxic T lymphocytes. Neurosurgery. 1992; 31:528-533.
64. Kruse C A, Lillehei K O, Mitchell D H, Kleinschmidt-DeMasters B, Bellgrau D. Analysis of interleukin 2 and various effector cell populations in adoptive immunotherapy of 9L rat gliosarcoma: allogeneic cytotoxic T lymphocytes prevent tumor take. Proc Natl Acad Sci USA. 1990; 87:9577-9581.

65. Miyatake S, Nishihara K, Kikuchi H, et al. Efficient tumor suppression by glioma-specific murine cytotoxic T lymphocytes transfected with interferon-gamma gene. J Natl Cancer Inst. 1990; 82:217-220.
66. Plautz G E, Touhalisky J E, Shu S. Treatment of murine gliomas by adoptive transfer of ex vivo activated tumor-draining lymph node cells. Cell Immunol. 1997; 178:101-107.
67. Saris S C, Spiess P, Lieberman D M, Lin S, Walbridge S, Oldfield E H. Treatment of murine primary brain tumors with systemic interleukin-2 and tumor-infiltrating lymphocytes. J Neurosurg. 1992; 76:513-519.
68. Tzeng J J, Barth R F, Clendenon N R, Gordon W A. Adoptive immunotherapy of a rat glioma using lymphokine-activated killer cells and interleukin 2. Cancer Res. 1990; 50:4338-4343.
69. Yamasaki T, Kikuchi H. An experimental approach to specific adoptive immunotherapy for malignant brain tumors. Nippon Geka Hokan. 1989; 58:485-492.
70. Yamasaki T, Handa H, Yamashita J, Watanabe Y, Namba Y, Hanaoka M. Specific adoptive immunotherapy with tumor-specific cytotoxic T-lymphocyte clone for murine malignant gliomas. Cancer Res. 1984; 44:1776-1783.
71. Yamasaki T, Handa H, Yamashita J, Watanabe Y, Namba Y, Hanaoka M. Specific adoptive immunotherapy of malignant glioma with long-term cytotoxic T lymphocyte line expanded in T-cell growth factor. Experimental study and future prospects. Neurosurg Rev. 1984; 7:37-54.
72. Kikuchi K, Neuwelt E A. Presence of immunosuppressive factors in brain-tumor cyst fluid. J Neurosurg. 1983; 59:790-799.
73. Yamanaka R, Tanaka R, Yoshida S, Saitoh T, Fujita K, Naganuma H. Suppression of TGF-beta1 in human gliomas by retroviral gene transfection enhances susceptibility to LAK cells. J Neurooncol. 1999; 43:27-34.
74. Kuppner M C, Hamou M F, Bodmer S, Fontana A, de Tribolet N. The glioblastoma-derived T-cell suppressor factor/transforming growth factor beta 2 inhibits the generation of lymphokine-activated killer (LAK) cells. Int J Cancer. 1988; 42:562-567.
75. Hayes R L. The cellular immunotherapy of primary brain tumors. Rev Neurol (Paris). 1992; 148:454-466.
76. Ingram M, Buckwalter J G, Jacques D B, et al. Immunotherapy for recurrent malignant glioma: an interim report on survival. Neurol Res. 1990; 12:265-273.
77. Jaeckle K A. Immunotherapy of malignant gliomas. Semin Oncol. 1994; 21:249-259.
78. Kruse C A, Cepeda L, Owens B, Johnson S D, Stears J, Lillehei K O. Treatment of recurrent glioma with intracavitary alloreactive cytotoxic T lymphocytes and interleukin-2. Cancer Immunol Immunother. 1997; 45:77-87.
79. Merchant R E, Baldwin N G, Rice C D, Bear H D. Adoptive immunotherapy of malignant glioma using tumor-sensitized T lymphocytes. Neurol Res. 1997; 19:145-152.
80. Nakagawa K, Kamezaki T, Shibata Y, Tsunoda T, Meguro K, Nose T. Effect of lymphokine-activated killer cells with or without radiation therapy against malignant brain tumors. Neurol Med Chir (Tokyo). 1995; 35:22-27.
81. Plautz G E, Barnett G H, Miller D W, et al. Systemic T cell adoptive immunotherapy of malignant gliomas. J Neurosurg. 1998; 89:42-51.
82. Sankhla S K, Nadkarni J S, Bhagwati S N. Adoptive immunotherapy using lymphokine-activated killer (LAK) cells and interleukin-2 for recurrent malignant primary brain tumors. J Neurooncol. 1996; 27:133-140.
83. Sawamura Y, de Tribolet N. Immunotherapy of brain tumors. J Neurosurg Sci. 1990; 34:265-278.
84. Thomas C, Schober R, Lenard H G, Lumenta C B, Jacques D B, Wechsler W. Immunotherapy with stimulated autologous lymphocytes in a case of a juvenile anaplastic glioma. Neuropediatrics. 1992; 23:123-125.
85. Tsurushima H, Liu S Q, Tuboi K, et al. Reduction of end-stage malignant glioma by injection with autologous cytotoxic T lymphocytes. Jpn J Cancer Res. 1999; 90:536-545.
86. Barba D, Saris S C, Holder C, Rosenberg S A, Oldfield E H. Intratumoral LAK cell and interleukin-2 therapy of human gliomas. J Neurosurg. 1989; 70:175-182.
87. Hayes R L, Koslow M, Hiesiger E M, et al. Improved long term survival after intracavitary interleukin-2 and lymphokine-activated killer cells for adults with recurrent malignant glioma. Cancer. 1995; 76:840-852.
88. Ingram M, Jacques S, Freshwater D B, Techy G B, Shelden C H, Helsper J T. Salvage immunotherapy of malignant glioma. Arch Surg. 1987; 122:1483-1486.
89. Jacobs S K, Wilson D J, Kornblith P L, Grimm E A. Interleukin-2 or autologous lymphokine-activated killer cell treatment of malignant glioma: phase I trial. Cancer Res. 1986; 46:2101-2104.
90. Jeffes E W, III, Beamer Y B, Jacques S, et al. Therapy of recurrent high-grade gliomas with surgery, autologous mitogen-activated IL-2-stimulated (MAK) killer lymphocytes, and rIL-2: II. Correlation of survival with MAK cell tumor necrosis factor production in vitro. Lymphokine Cytokine Res. 1991; 10:89-94.
91. Merchant R E, McVicar D W, Merchant L H, Young H F. Treatment of recurrent malignant glioma by repeated intracerebral injections of human recombinant interleukin-2 alone or in combination with systemic interferon-alpha. Results of a phase I clinical trial. J Neurooncol. 1992; 12:75-83.
92. Yoshida S, Takai N, Saito T, Tanaka R. Adoptive immunotherapy in patients with malignant glioma. Gan To Kagaku Ryoho. 1987; 14:1930-1932.
93. Davico B L, De Monte L B, Spagnoli G C, et al. Bispecific monoclonal antibody anti-CD3 x anti-tenascin: an immunotherapeutic agent for human glioma. Int J Cancer. 1995; 61:509-515.
94. Jung G, Brandi M, Eisner W, et al. Local immunotherapy of glioma patients with a combination of 2 bispecific antibody fragments and resting autologous lymphocytes: evidence for in situ t-cell activation and therapeutic efficacy. Int J Cancer. 2001; 91:225-230.
95. Pfosser A, Brandt M, Salih H, Grosse-Hovest L, Jung G. Role of target antigen in bispecific-antibody-mediated killing of human glioblastoma cells: a pre-clinical study. Int J Cancer. 1999; 80:612-616.
96. Yoshida J, Takaoka T, Mizuno M, Momota H, Okada H. Cytolysis of malignant glioma cells by lymphokine-activated killer cells combined with anti-CD3/antiglioma bifunctional antibody and tumor necrosis factor-alpha. J Surg Oncol. 1996; 62:177-182.
97. Imaizumi T, Kuramoto T, Matsunaga K, et al. Expression of the tumor-rejection antigen SART1 in brain tumors. Int J Cancer. 1999; 83:760-764.
98. Eshhar Z, Waks T, Gross G, Schindler D G. Specific activation and targeting of cytotoxic lymphocytes through chimeric single chains consisting of antibody-binding domains and the gamma or zeta subunits of the immunoglobulin and T-cell receptors. Proc Natl Acad Sci USA. 1993; 90:720-724.

99. Haynes N M, Snook M B, Trapani J A, et al. Redirecting mouse CTL against colon carcinoma: superior signaling efficacy of single-chain variable domain chimeras containing TCR-zeta vs Fc epsilon RI-gamma. J Immunol. 2001; 166:182-187.

100. Hombach A, Heuser C, Sircar R, et al. An anti-CD30 chimeric receptor that mediates CD3-zeta-independent T-cell activation against Hodgkin's lymphoma cells in the presence of soluble CD30. Cancer Res. 1998; 58:1116-1119.

101. Hombach A, Schneider C, Sent D, et al. An entirely humanized CD3 zeta-chain signaling receptor that directs peripheral blood t cells to specific lysis of carcinoembryonic antigen-positive tumor cells. Int J Cancer. 2000; 88:115-120.

102. Hombach A, Sircar R, Heuser C, et al. Chimeric anti-TAG72 receptors with immunoglobulin constant Fc domains and gamma or zeta signalling chains. Int J Mol Med. 1998; 2:99-103.

103. Moritz D, Wels W, Mattern J, Groner B. Cytotoxic T lymphocytes with a grafted recognition specificity for ERBB2-expressing tumor cells. Proc Natl Acad Sci USA. 1994; 91:4318-4322.

104. Weijtens M E, Willemsen R A, Valerio D, Stam K, Bolhuis R L. Single chain Ig/gamma gene-redirected human T lymphocytes produce cytokines, specifically lyse tumor cells, and recycle lytic capacity. J Immunol. 1996; 157:836-843.

105. Altenschmidt U, Klundt E, Groner B. Adoptive transfer of in vitro-targeted, activated T lymphocytes results in total tumor regression. J Immunol. 1997; 159:5509-5515.

106. Jensen M, Tan G, Forman S, Wu A M, Raubitschek A. CD20 is a molecular target for scFvFc:zeta receptor redirected T cells: implications for cellular immunotherapy of CD20+ malignancy. Biol Blood Marrow Transplant. 1998; 4:75-83.

107. Jensen M C, Clarke P, Tan G, et al. Human T lymphocyte genetic modification with naked DNA. Mol Ther. 2000; 1:49-55.

108. Minty A, Chalon P, Derocq J M, et al. Interleukin-13 is a new human lymphokine regulating inflammatory and immune responses. Nature. 1993; 362:248-250.

109. Boon T, Cerottini J C, Van den EB, van der BP, Van Pel A. Tumor antigens recognized by T lymphocytes. Annu Rev Immunol. 1994; 12:337-365.

110. Castelli C, Rivoltini L, Andreola G, Carrabba M, Renkvist N, Parmiani G. T-cell recognition of melanoma-associated antigens. J Cell Physiol. 2000; 182:323-331.

111. Chi D D, Merchant R E, Rand R, et al. Molecular detection of tumor-associated antigens shared by human cutaneous melanomas and gliomas. Am J Pathol. 1997; 150:2143-2152.

112. Boon T, Coulie P, Marchand M, Weynants P, Wolfel T, Brichard V. Genes coding for tumor rejection antigens: perspectives for specific immunotherapy. Important Adv Oncol. 1994; 53-69.

113. Cebon J, MacGregor D, Scott A, DeBoer R. Immunotherapy of melanoma: targeting defined antigens. Australas J Dermatol. 1997; 38 Suppl 1:S66-S72.

114. Greenberg P D, Riddell S R. Tumor-specific T-cell immunity: ready for prime time? Natl Cancer Inst. 1992; 84:1059-1061.

115. Cohen J L, Saron M F, Boyer O, et al. Preservation of graft-versus-infection effects after suicide gene therapy for prevention of graft-versus-host disease. Hum Gene Ther. 2000; 11:2473-2481.

116. Drobyski W R, Morse H C, III, Burns W H, Casper J T, Sandford G. Protection from lethal murine graft-versus-host disease without compromise of alloengraftment using transgenic donor T cells expressing a thymidine kinase suicide gene. Blood. 2001; 97:2506-2513.

117. Link C J, Jr., Traynor A, Seregina T, Burt R K. Adoptive immunotherapy for leukemia: donor lymphocytes transduced with the herpes simplex thymidine kinase gene. Cancer Treat Res. 1999; 101:369-375.

118. Spencer D M. Developments in suicide genes for preclinical and clinical applications. Curr Opin Mol Ther. 2000; 2:433-440.

---

The invention claimed is:

1. A chimeric immunoreceptor comprising SEQ ID NO:22.
2. A chimeric immunoreceptor encoded by a nucleic acid sequence comprising SEQ D NO:19.
3. A method for treating human cancer, comprising administering to a human suffering from a glioma that overexpresses IL13α2 receptor a plurality of T lymphocyte cells expressing an immunoreceptor of claim 1.
4. A method for treating human cancer, comprising administering to a human suffering from a glioma that overexpresses IL13α2 receptor a plurality of T lymphocyte cells expressing an immunoreceptor of claim 2.
5. A vector which consists essentially of SEQ ID NO:19.

* * * * *